United States Patent
Kim et al.

(10) Patent No.: US 10,066,207 B2
(45) Date of Patent: Sep. 4, 2018

(54) NATURAL KILLER CELLS WITH ENHANCED IMMUNE RESPONSE

(71) Applicant: Board of Trustees of Michigan State University, East Lansing, MI (US)

(72) Inventors: Sungjin Kim, Okemos, MI (US); Jeannine Scott, Charlotte, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 964 days.

(21) Appl. No.: 13/865,762

(22) Filed: Apr. 18, 2013

(65) Prior Publication Data
US 2013/0295044 A1 Nov. 7, 2013

Related U.S. Application Data

(60) Provisional application No. 61/625,725, filed on Apr. 18, 2012.

(51) Int. Cl.
*A61K 35/17* (2015.01)
*A61K 38/20* (2006.01)
*C12N 5/0783* (2010.01)

(52) U.S. Cl.
CPC ............ *C12N 5/0646* (2013.01); *A61K 35/17* (2013.01); *Y02A 50/473* (2018.01); *Y02A 50/475* (2018.01)

(58) Field of Classification Search
None
See application file for complete search history.

(56) References Cited

PUBLICATIONS

Burns et al (Bone Marrow Transpl. 2003, 32: 177-186).*
Parkhurst et al (Clin. Canc. Res. 2011, 17(19): 6287-6297).*
Pernick, N (Handbook of Practical Immunohistochemistry, 2nd Ed., Springer, 2015, Table of Contents, 2 pages).*
Alici et al. "Anti-myeloma activity of endogenous and adoptively transferred activated natural killer cells in experimental multiple myeloma model," Exp Hematol, 35(12): 1839-1846 (2007).
Bachanova et al., "NK cells in therapy of cancer," Crit Rev Oncog, 19(1-2): 133-141 (2014).
Balasa et al., "Elotuzumab enhances natural killer cell activation and myeloma cell killing through interleukin2 and TNFα pathways," Cancer Immunol Immunother, 64: 61-73 (2015).
Benson et al.,"IPH2101, a novel anti-inhibitory KIR antibody, and lenalidomide combine to enhance the natural killer cell versus multiple myeloma effect," Blood, 118(24): 6387-6391 (2011).
Burns et al., "IL-2-based immunotherapy after autologous transplantation for lymphoma and breast cancer induces immune activation and cytokine release: a phase I/II trial," Bone Marrow Transplant, 32(2): 177-186 (2003).
Castagna et al., "Re-discovering NK cell allo-reactivity in the; therapy of solid tumors," J Immunotherapy Cancer 4: 54 (2016).

Chan et al., "Antibody-dependent cell-mediated cytotoxicity overcomes NK cell-resistance in MLL-rearranged leukemia expressing inhibitory KIR ligands but not activating ligands," Clin Cancer Res, 18(22): 6296-6305 (2012).
Chen et al., "Cetuximab intensifies the ADCC activity of adoptive NK cells in a nude mouse colorectal cancer xenograft model," Oncol Lett, 12(3): 1868-1876 (2016).
Chiesa et al., "Features of Memory-Like and PD-1+ Human nK Cell Subsets," Front Immunol, 7: 351 (2016).
Chouaib et al., "Improving the outcome of leukemia by natural killer cell-based immunotherapeutic strategies," Front Immunol, 5: 95 (2014).
Chu et al., "Targeting CD20+ Aggressive B-cell Non-Hodgkin Lymphoma by Anti-CD20 CAR mRNA-Modified Expanded Natural Killer Cells In Vitro and in NSG Mice," Cancer Immunol Res, 3(4): 333-344 (2015).
Dahlberg et al., "Natural killer cell-based therapies targeting cancer: possible strategies to gain and sustain anti-tumor activity," Front Immunol, 6: 605 (2015).
Fernandez et al., "Activated and expanded natural killer cells target osteosarcoma tumor initiating cells in an NKG2D-NKG2DL dependent manner," Cancer Lett, 368(1): 54-63 (2015).
Garg et al., "Highly activated and expanded natural killer cells for multiple myeloma immunotherapy," Haematologica, 97(9): 1348-1356 (2012).
Genßler et al., "Dual targeting of glioblastoma with chimeric antigen receptor-engineered natural killer cells overcomes heterogeneity of target antigen expression and enhances antitumor activity and survival," Oncoimmunology, 5(4): e1119354 (2016).
Gong et al., "miR-30c-1* promotes natural killer cell cytotoxicity; against human hepatoma cells by targeting the transcription factor HMBOX1," Cancer Sci, 103(4): 645-652 (2012).
Granzin et al., "Fully automated expansion and activation of clinical-grade natural killer cells for adoptive immunotherapy," 17(5): 621-632 (2015).
Han et al. "CAR-Engineered NK Cells Targeting Wild-Type EGFR and EGFRvIII Enhance Killing of Glioblastoma and Patient-Derived Glioblastoma Stem Cells," Sci. Rep. 5:11483 (2015).
Huang et al., "The PD-1/B7-H1 pathway modulates the natural killer cells versus mouse glioma stem cells," PLoS One, 10(8): e0134715 (2015).
Hwang et al., "Identification of human NK cells that are deficient for signaling adaptor FcRγ and specialized for antibody-dependent immune functions," Int Immunol, 24(12): 793-802 (2012).
Kohrt et al., "Anti-KIR antibody enhancement of anti-lymphoma activity of natural killer cells as monotherapy and in combination with anti-CD20 antibodies," Blood, 123(5): 678-686 (2014).
Kohrt et al., "Stimulation of natural killer cells with a CD137-specific antibody enhances trastuzumab efficacy in xenotransplant models of breast cancer," J Clin Invest, 122(3): 1066-1075 (2012).
Lanier et al., "Up on the tightrope: natural killer cell activation and inhibition," Nat Immunol, 9(5): 495-502 (2008).

(Continued)

*Primary Examiner* — Michael Szperka
*Assistant Examiner* — Marianne DiBrino
(74) *Attorney, Agent, or Firm* — Foley Hoag LLP; DeAnn F. Smith; Allison Gilder

(57) ABSTRACT

The invention relates to a specialized subpopulation of natural killer cells that have enhanced effector functions and the potential to kill malignant tumor cells or infected cells when the natural killer cells are exposed to an antibody bound to the tumor cells or the infected cells.

12 Claims, 37 Drawing Sheets
Specification includes a Sequence Listing.

(56) References Cited

PUBLICATIONS

Lee et al., "Epigenetic modification and antibody-dependent expansion of memory-like NK cells in human cytomegalovirus-infected individuals," Immunity, 42(3): 431-432 (2015).

Lim et al., "GMP-compliant, large-scale expanded allogeneic natural killer cells have potent cytolytic activity against cancer cells in vitro and in vivo," PLoS One, 8(1): e53611 (2013).

Lim et al., "Present and future of allogeneic natural killer cell therapy," Front Immunol, 6: 286 (2015).

Lonial et al., "Daratumumab monotherapy in patients with treatment-refractory multiple myeloma (SIRIUS): an open-label, randomised, phase 2 trial," Lancet, 387(10027): 1551-1560 (2016).

Luedke et al., "Cetuximab therapy in head and neck cancer: Immune modulation with interleukin-12 and other natural killer cell-activating cytokines," 152(3): 431-440 (2012).

Masuyama et al., "Ex vivo expansion of natural killer cells from human peripheral blood mononuclear cells co-stimulated with anti-CD3 and anti-CD52 monoclonal antibodies," Cytotherapy, 18(1): 80-90 (2016).

Parkhurst et al., "Adoptive transfer of autologous natural killer cells leads to high levels of circulating natural killer cells but does not mediate tumor regression," Clin Cancer Res, 17(19): 6287-6297 (2011).

Perez-Martinez et al., "Arabinoxylan rice bran (MGN-3/Biobran) enhances natural killer cell-mediated cytotoxicity against neuroblastoma in vitro and in vivo," Cytotherapy, 17(5): 601-612 (2015).

Poli et al., "Targeting glioblastoma with NK cells and mAb against NG2/CSPG4 prolongs animal survival," Oncotarget, 4(9): 1527-1546 (2013).

Rezvani et al., "The application of natural killer cell immunotherapy for the treatment of cancer," Front Immunol, 6: 578 (2015).

Schönfeld et al., "Selective inhibition of tumor growth by clonal NK cells expressing an ErbB2/HER2-specific chimeric antigen receptor," Mol Ther, 23(2): 330-338 (2015).

Shimasaki et al., "A clinically adaptable method to enhance the cytotoxicity of natural killer cells against B-cell malignancies," Cytotherapy, 14(7): 830-840 (2012).

Shiokawa et al., "In vivo assay of human NK-dependent ADCC using NOD/SCID/gammac(null) (NOG) mice," Biochem Biophys Res Commun, 399(4): 733-737 (2010).

Srivastava et al., "Effects of interleukin-18 on natural killer cells: costimulation of activation through Fc receptors for immunoglobulin," Cancer Immunol Immunother, 62(6): 1073-1082 (2013).

Stevens et al., "'Trained immunity': consequences for lymphoid malignancies," Haematologica, 101(12): 1460-1468 (2016).

Suck et al., "NK-92: an 'off-the-shelf therapeutic' for adoptive natural killer cell-based cancer immunotherapy," Cancer Immunol Immunother, 65(4): 485-492 (2016). (Abstract).

Tran et al., "TGFβR1 blockade with galunisertib (LY2157299) enhances anti-neuroblastoma activity of the anti-GD2 antibody dinutuximab (ch14.18) with natural killer cells," Clin Cancer Res, 23(3): 804-813 (2017). (Abstract).

Tschan-Plessl et al., "Human cytomegalovirus infection enhances NK cell activity in vitro," Transplant Direct, 2(7): e89 (2016).

Veuillen et al., "Primary B-CLL resistance to NK cell cytotoxicity can be overcome in vitro and in vivo by priming NK cells and monoclonal antibody therapy," J Clin Immunol, 32(2): 632-646 (2012).

Wang et al., "NK cell-mediated antibody-dependent cellular cytotoxicity in cancer immunotherapy," Front Immunol, 6: 368 (2015).

Xing et al., "Cord blood natural killer cells exhibit impaired lytic immunological synapse formation that is reversed with IL-2 ex vivo expansion," J Immunother, 33(7): 684-696 (2010).

Zhang et al., "Antibody-dependent memory-like NK cells distinguished by FcRγ-deficiency1," J Immunol, 190(4): 1402-1406 (2013).

Zhu et al., "An IL-12/Shh-C domain fusion protein-based IL-12 autocrine loop for sustained natural killer cell activation," Int J Oncol, 41(2): 661-669 (2012).

* cited by examiner

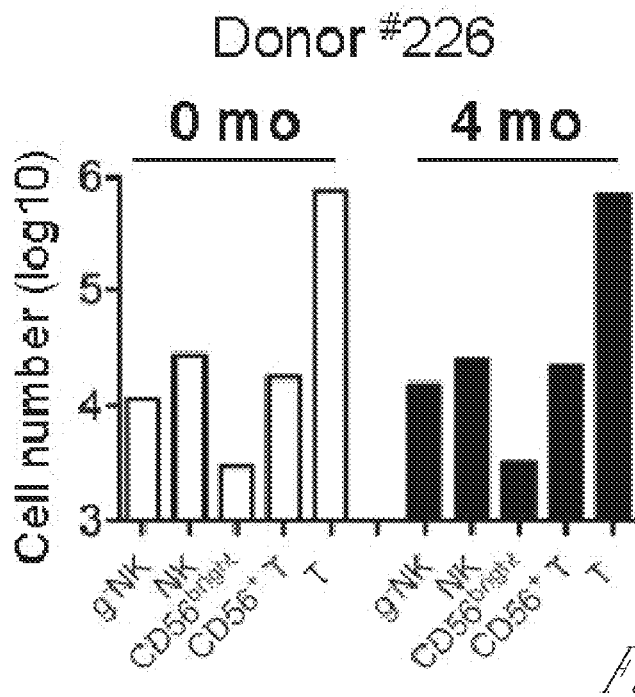
Fig.5D1
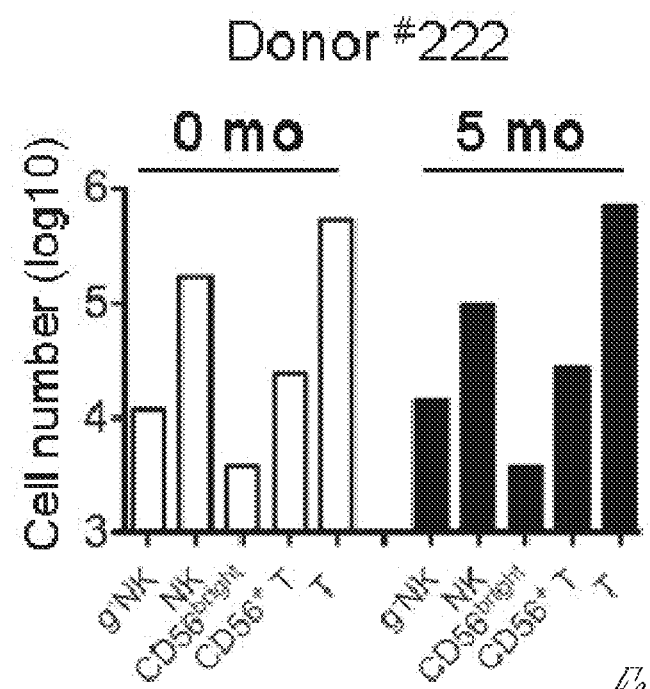
Fig.5D2

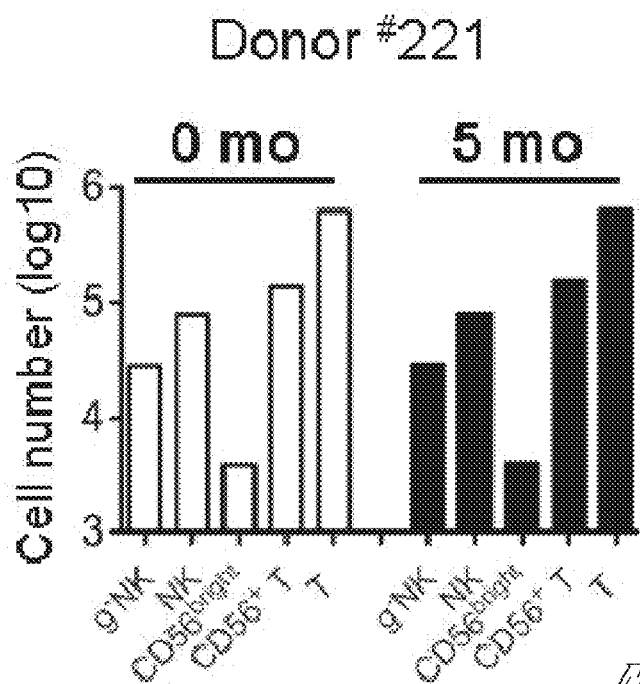
Fig. 5D3
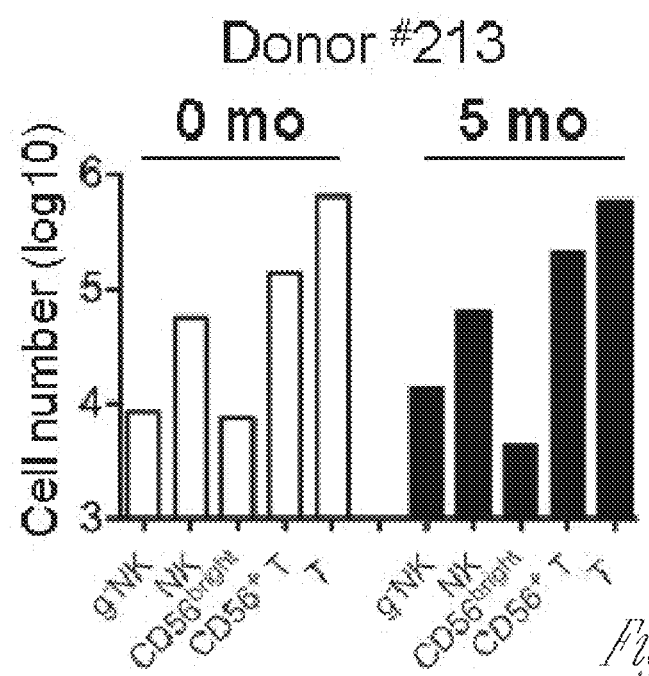
Fig. 5D4

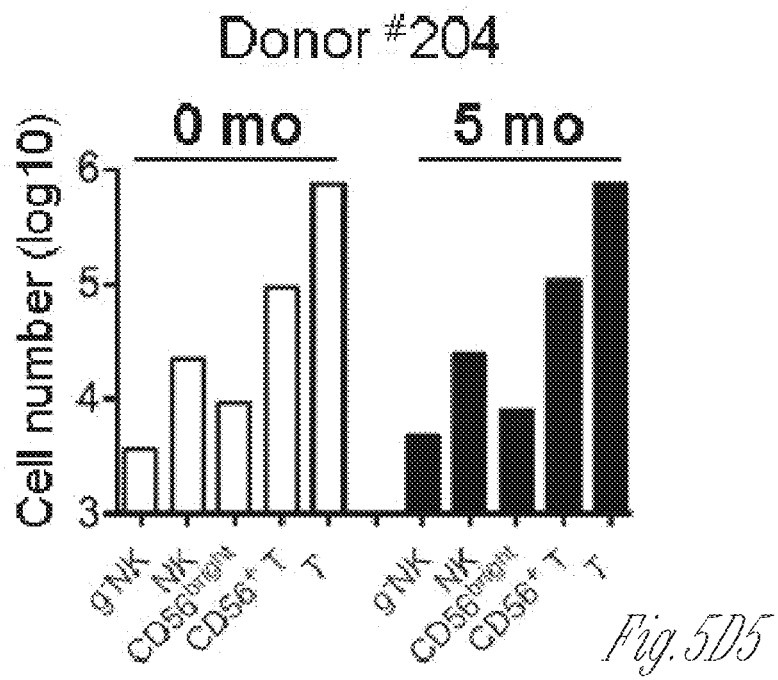
Fig.5D5
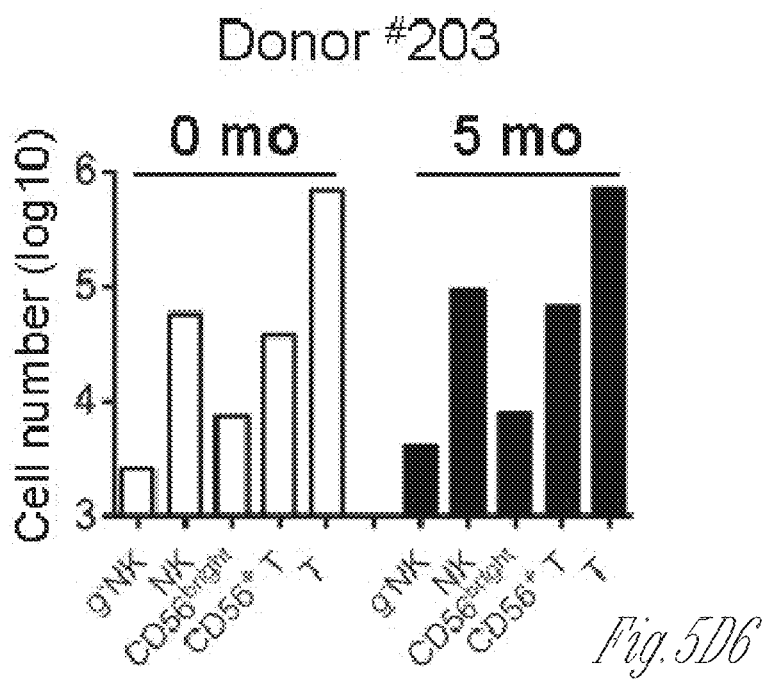
Fig.5D6

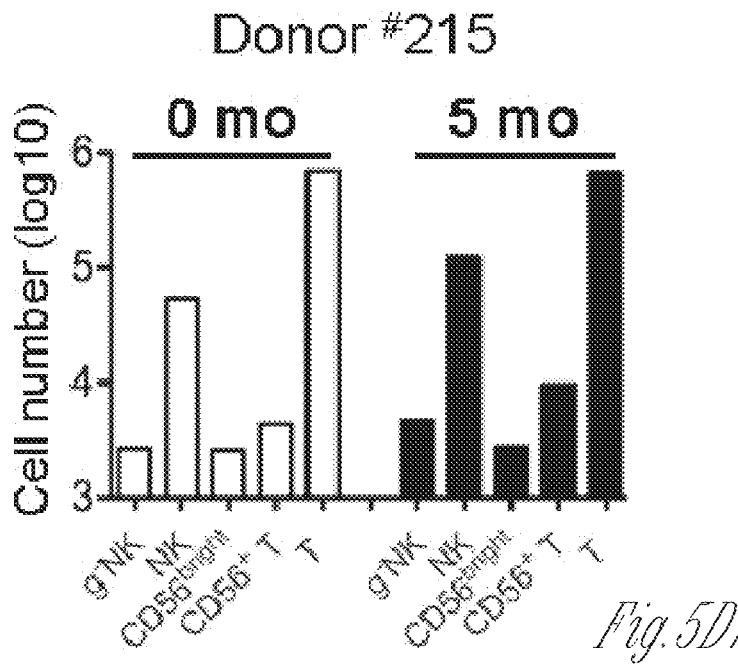
Fig.5D7
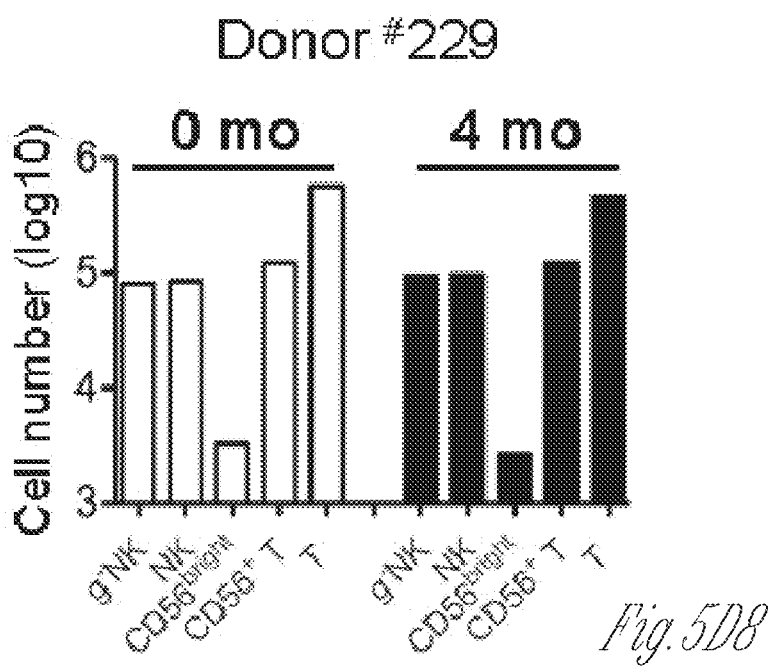
Fig.5D8

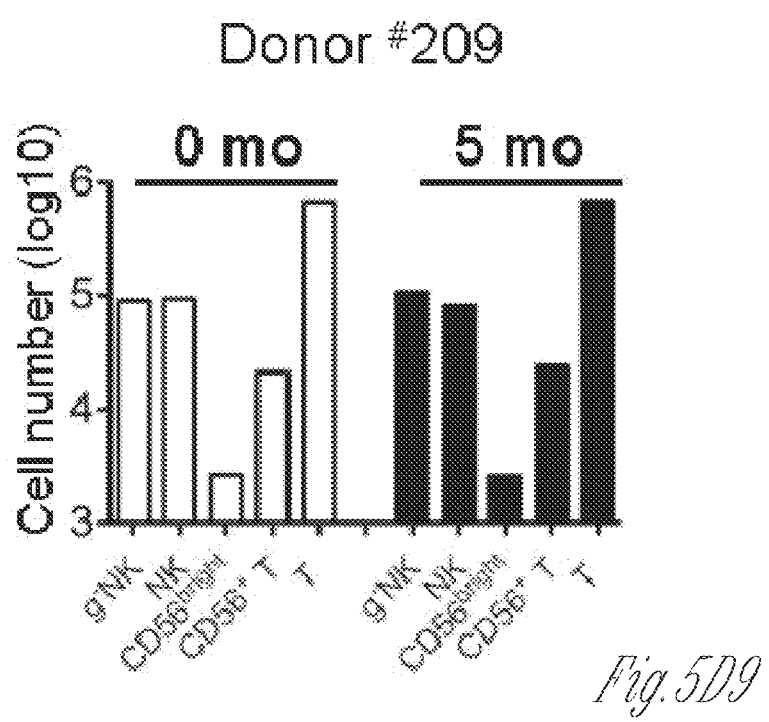
Fig. 5D9

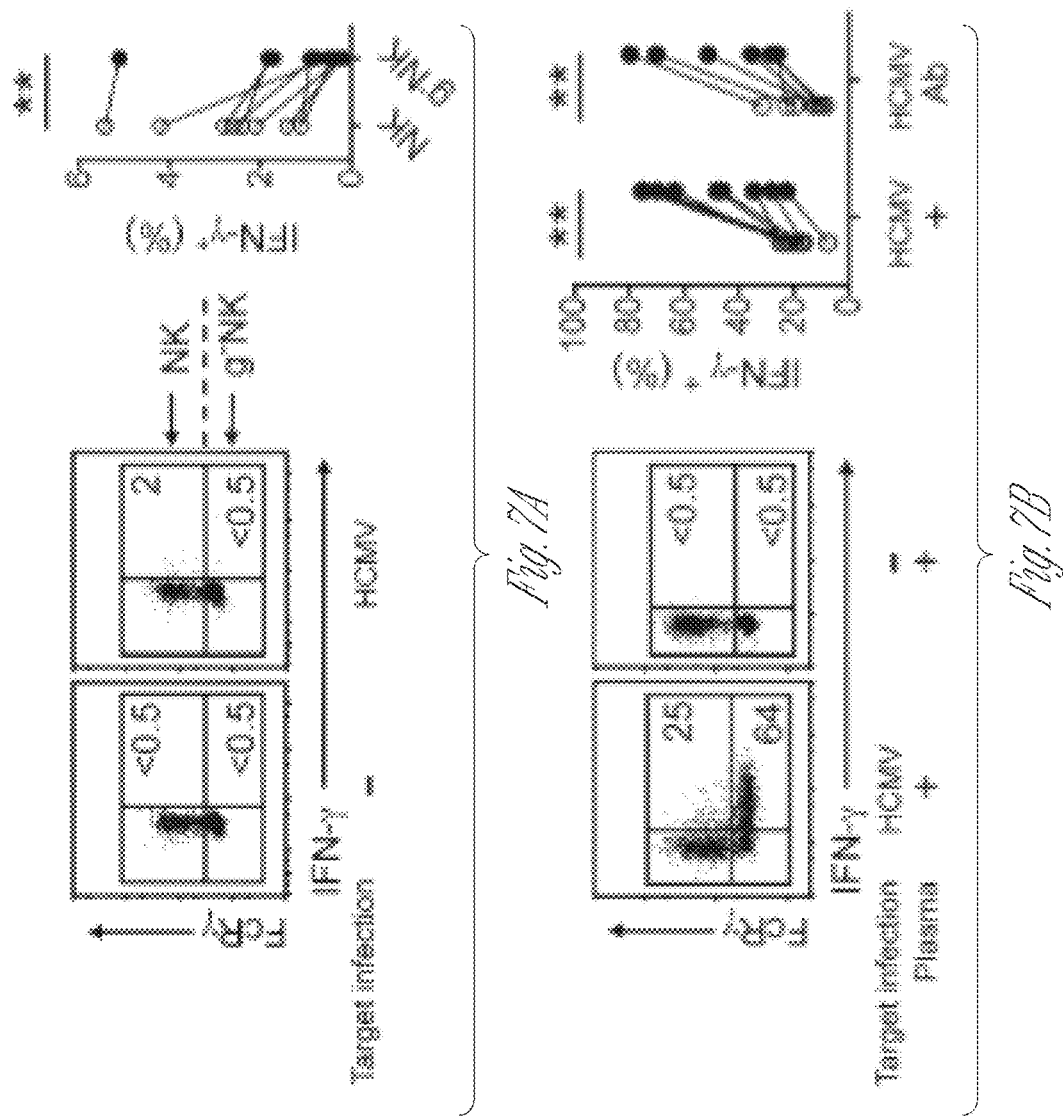

ns, the invention relates to novel methods for treating cancer, microbial infection and/or viral infection in a subject.

SEQUENCE LISTING

```
<160> NUMBER OF SEQ ID NOS: 8

<210> SEQ ID NO 1
<211> LENGTH: 86
<212> TYPE: PRT
<213> ORGANISM: Homo sapiens

<400> SEQUENCE: 1

Met Ile Pro Ala Val Val Leu Leu Leu Leu Leu Val Glu Gln Ala
 1               5                  10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85
```

<210> SEQ ID NO 2
<211> LENGTH: 82
<212> TYPE: PRT
<213> ORGANISM: Homo sapiens

<400> SEQUENCE: 2

```
Ala Ile Leu Gln Ala Gln Leu Pro Ile Thr Glu Ala Gln Ser Phe Gly
 1               5                  10                  15

Leu Leu Asp Pro Lys Leu Cys Tyr Leu Leu Asp Gly Ile Leu Phe Ile
             20                  25                  30

Tyr Gly Val Ile Leu Thr Ala Leu Phe Leu Arg Val Lys Phe Ser Arg
         35                  40                  45

Ser Ala Asp Ala Pro Ala Tyr Gln Gln Gly Gln Asn Gln Leu Tyr Asn
50                  55                  60

Glu Leu Asn Leu Gly Arg Arg Glu Glu Tyr Asp Val Leu Asp Lys Arg
65                  70                  75                  80

Arg Gly
```

<210> SEQ ID NO 3
<211> LENGTH: 444
<212> TYPE: PRT
<213> ORGANISM: Homo sapiens

<400> SEQUENCE: 3

```
Met Ser Leu Met Val Val Ser Met Ala Cys Val Gly Leu Phe Leu Val
 1               5                  10                  15

Gln Arg Ala Gly Pro His Met Gly Gly Gln Asp Lys Pro Phe Leu Ser
             20                  25                  30

Ala Trp Pro Ser Ala Val Val Pro Arg Gly Gly His Val Thr Leu Arg
         35                  40                  45

Cys His Tyr Arg His Arg Phe Asn Asn Phe Met Leu Tyr Lys Glu Asp
    50                  55                  60

Arg Ile His Ile Pro Ile Phe His Gly Arg Ile Phe Gln Glu Ser Phe
65                  70                  75                  80

Asn Met Ser Pro Val Thr Thr Ala His Ala Gly Asn Tyr Thr Cys Arg
                85                  90                  95

Gly Ser His Pro His Ser Pro Thr Gly Trp Ser Ala Pro Ser Asn Pro
            100                 105                 110

Val Val Ile Met Val Thr Gly Asn His Arg Lys Pro Ser Leu Leu Ala
        115                 120                 125

His Pro Gly Pro Leu Val Lys Ser Gly Glu Arg Val Ile Leu Gln Cys
    130                 135                 140

Trp Ser Asp Ile Met Phe Glu His Phe Phe Leu His Lys Glu Gly Ile
145                 150                 155                 160

Ser Lys Asp Pro Ser Arg Leu Val Gly Gln Ile His Asp Gly Val Ser
                165                 170                 175

Lys Ala Asn Phe Ser Ile Gly Pro Met Met Leu Ala Leu Ala Gly Thr
            180                 185                 190

Tyr Arg Cys Tyr Gly Ser Val Thr His Thr Pro Tyr Gln Leu Ser Ala
        195                 200                 205

Pro Ser Asp Pro Leu Asp Ile Val Val Thr Gly Pro Tyr Glu Lys Pro
    210                 215                 220

Ser Leu Ser Ala Gln Pro Gly Pro Lys Val Gln Ala Gly Glu Ser Val
225                 230                 235                 240

Thr Leu Ser Cys Ser Ser Arg Ser Ser Tyr Asp Met Tyr His Leu Ser
                245                 250                 255
```

-continued

Arg Glu Gly Gly Ala His Glu Arg Leu Pro Ala Val Arg Lys Val
            260                 265                 270

Asn Arg Thr Phe Gln Ala Asp Phe Pro Leu Gly Pro Ala Thr His Gly
        275                 280                 285

Gly Thr Tyr Arg Cys Phe Gly Ser Phe Arg His Ser Pro Tyr Glu Trp
    290                 295                 300

Ser Asp Pro Ser Asp Pro Leu Leu Val Ser Val Thr Gly Asn Pro Ser
305                 310                 315                 320

Ser Ser Trp Pro Ser Pro Thr Glu Pro Ser Ser Lys Ser Gly Asn Pro
            325                 330                 335

Arg His Leu His Ile Leu Ile Gly Thr Ser Val Val Ile Ile Leu Phe
        340                 345                 350

Ile Leu Leu Leu Phe Phe Leu Leu His Leu Trp Cys Ser Asn Lys Lys
    355                 360                 365

Asn Ala Ala Val Met Asp Gln Glu Pro Ala Gly Asn Arg Thr Ala Asn
370                 375                 380

Ser Glu Asp Ser Asp Glu Gln Asp Pro Glu Glu Val Thr Tyr Ala Gln
385                 390                 395                 400

Leu Asp His Cys Val Phe Thr Gln Arg Lys Ile Thr Arg Pro Ser Gln
                405                 410                 415

Arg Pro Lys Thr Pro Pro Thr Asp Thr Ile Leu Tyr Thr Glu Leu Pro
            420                 425                 430

Asn Ala Lys Pro Arg Ser Lys Val Val Ser Cys Pro
            435                 440

<210> SEQ ID NO 4
<211> LENGTH: 276
<212> TYPE: PRT
<213> ORGANISM: Homo sapiens

<400> SEQUENCE: 4

Met Ala Trp Arg Ala Leu His Pro Leu Leu Leu Leu Leu Leu Leu Phe
1               5                   10                  15

Pro Gly Ser Gln Ala Gln Ser Lys Ala Gln Val Leu Gln Ser Val Ala
            20                  25                  30

Gly Gln Thr Leu Thr Val Arg Cys Gln Tyr Pro Pro Thr Gly Ser Leu
        35                  40                  45

Tyr Glu Lys Lys Gly Trp Cys Lys Glu Ala Ser Ala Leu Val Cys Ile
    50                  55                  60

Arg Leu Val Thr Ser Ser Lys Pro Arg Thr Met Ala Trp Thr Ser Arg
65                  70                  75                  80

Phe Thr Ile Trp Asp Asp Pro Asp Ala Gly Phe Phe Thr Val Thr Met
                85                  90                  95

Thr Asp Leu Arg Glu Glu Asp Ser Gly His Tyr Trp Cys Arg Ile Tyr
            100                 105                 110

Arg Pro Ser Asp Asn Ser Val Ser Lys Ser Val Arg Phe Tyr Leu Val
        115                 120                 125

Val Ser Pro Ala Ser Ala Ser Thr Gln Thr Ser Trp Thr Pro Arg Asp
    130                 135                 140

Leu Val Ser Ser Gln Thr Gln Thr Gln Ser Cys Val Pro Pro Thr Ala
145                 150                 155                 160

Gly Ala Arg Gln Ala Pro Glu Ser Pro Ser Thr Ile Pro Val Pro Ser
                165                 170                 175

Gln Pro Gln Asn Ser Thr Leu Arg Pro Gly Pro Ala Ala Pro Ile Ala

```
                180                 185                 190
Leu Val Pro Val Phe Cys Gly Leu Leu Val Ala Lys Ser Leu Val Leu
            195                 200                 205

Ser Ala Leu Leu Val Trp Trp Gly Asp Ile Trp Trp Lys Thr Met Met
            210                 215                 220

Glu Leu Arg Ser Leu Asp Thr Gln Lys Ala Thr Cys His Leu Gln Gln
225                 230                 235                 240

Val Thr Asp Leu Pro Trp Thr Ser Val Ser Ser Pro Val Glu Arg Glu
                245                 250                 255

Ile Leu Tyr His Thr Val Ala Arg Thr Lys Ile Ser Asp Asp Asp Asp
                260                 265                 270

Glu His Thr Leu
        275

<210> SEQ ID NO 5
<211> LENGTH: 21
<212> TYPE: DNA
<213> ORGANISM: Artificial Sequence
<220> FEATURE:
<223> OTHER INFORMATION: A synthetic primer

<400> SEQUENCE: 5
cggccgatct ccagcccaag a                                        21

<210> SEQ ID NO 6
<211> LENGTH: 22
<212> TYPE: DNA
<213> ORGANISM: Artificial Sequence
<220> FEATURE:
<223> OTHER INFORMATION: A synthetic primer

<400> SEQUENCE: 6
gcatgcaggc atatgtgatg cc                                       22

<210> SEQ ID NO 7
<211> LENGTH: 16
<212> TYPE: DNA
<213> ORGANISM: Artificial Sequence
<220> FEATURE:
<223> OTHER INFORMATION: A synthetic primer

<400> SEQUENCE: 7
ggaaggtgaa ggtcgg                                              16

<210> SEQ ID NO 8
<211> LENGTH: 20
<212> TYPE: DNA
<213> ORGANISM: Artificial Sequence
<220> FEATURE:
<223> OTHER INFORMATION: A synthetic primer

<400> SEQUENCE: 8
gaagatggtg atgggatttc                                          20
```

NATURAL KILLER CELLS WITH ENHANCED IMMUNE RESPONSE

CROSS-REFERENCE TO RELATED APPLICATIONS

This application claims priority from U.S. Provisional Application No. 61/625,725, filed Apr. 18, 2012, the entire disclosure of which is herein incorporated by reference.

STATEMENT OF GOVERNMENT RIGHTS

This invention was made with government support under Grant No. CA149476 by the National Institutes of Health. The government has certain rights in the invention.

BACKGROUND

Cancer treatment often involves surgery, radiation therapy and chemotherapy, in varying combinations. However, these treatments all too frequently are just temporary solutions to a progressively life-threatening disease. Cancer cells can escape surgical intervention, be unresponsive to radiation or develop resistance to chemotherapeutic agents. In addition, these treatments typically have significant adverse physiological side effects. Research is currently underway to develop methods for stimulating a patient's own immune system, but development of such methods is still in its infancy.

In the recent years, antibody-based therapy has become more frequently used for an increasing number of human cancers. There are more than 20 monoclonal antibody drugs treatments in use today for a variety of malignancies, including trastuzumab (Herceptin) for breast cancer, rituximab (Rituxan) for lymphoma, and cetuximab (Erbitux) for head and neck squamous cell carcinoma. However, the clinical efficacy of such antibody treatments has been highly variable. The reason underlying the differential response to antibody therapy is poorly understood. The ability to predict which patients would benefit from the treatment would not only help tailor an individual's treatment plan, but it would also help avoid potentially serious adverse events, such as anaphylaxis and serum sickness, and lead to more responsible utilization of resources (given that the cost of this therapy is typically very high, often in the range of $10,000 per month). Thus, a strategy to select patients who would benefit from monoclonal antibody immunotherapy is needed.

The use of biomarkers to help guide this type of therapy has been limited to the measurement of the targeted tumor antigen itself, e.g. Her2/neu expression on breast cancer cells for trastuzumab, or CD20 expression on B-cell lymphomas for rituximab. Similarly, the expression of EGFR and the status of its downstream signaling protein, KRAS, have been predictive of potential benefits from treatment with anti-EGFR (cetuximab) in combination with chemotherapy. However, these antibody targets do not vary sufficiently to explain the heterogeneity that is seen in the clinical responses. Thus, additional ways to identify which patients may benefit from which therapy is needed. New methods for modulating an immune response against cancer cells would also be beneficial.

SUMMARY

The invention relates to FcRγ-deficient natural killer cells that exhibit enhanced immune responses. In other embodiments, the invention relates to novel methods for treating cancer, microbial infection and/or viral infection in a subject.

One embodiment provides a method of detecting whether a sample from a subject comprises g⁻NK (g⁻NK) cells, comprising detecting whether the sample comprises natural killer cells that do not express detectable amounts of FcRγ (g⁻NK cells), to thereby detect whether a sample from a subject comprises g⁻NK cells. Another embodiment provides administering an antibody to the subject if the sample comprises g⁻NK cells. In one embodiment, unnecessary treatment of the subject is avoided if the sample does not comprise g⁻NK cells by not administering an antibody to the subject. In one embodiment, the antibody can bind to an antigen on or in a microbe, virus, or cancer cell.

One embodiment provides a composition comprising natural killer cells that do not express substantial FcRγ (g⁻NK cells). In one embodiment, the composition comprises more than 50% g⁻NK cells. In another embodiment, the composition comprises more than 70% g⁻NK cells. In another embodiment, the composition comprises more than 80% g⁻NK cells. In one embodiment, the composition comprises about 5-99% g⁻NK cells, or any percentage of g⁻NK cells between 5 and 99% inclusive. In one embodiment, the g⁻NK cells express no detectable FcRγ. In another embodiment, the g⁻NK cells express no immunologically detectable FcRγ. In one embodiment, the g⁻NK cells express no detectable FcRγ mRNA. In another embodiment, the g⁻NK cells express KIR2DL2/3, CD16, NKp30, NKp46 or a combination thereof. In one embodiment, the g⁻NK cells produce significantly greater amounts of a cytokine than natural killer cells that do express FcRγ. In another embodiment, the cytokine is interferon-gamma (IFN-γ), tumor necrosis factor-α (TNF-α), or a combination thereof. In one embodiment, the g⁻NK cells produce significantly greater amounts of a chemokine. In one embodiment, the chemokine is MIP-1α, MIP-1β or a combination thereof. In another embodiment, the g⁻NK cells produce the cytokine or the chemokine upon stimulation through the Fc receptor CD16. In another embodiment, the g⁻NK cells kill tumor cells, kill microbially-infected cells, kill microbes, kill virally-infected cells and/or kill viruses. In another embodiment, the composition comprises a physiologically acceptable carrier. In another embodiment, the composition comprises a pharmaceutically effective amount of the g⁻NK cells. In one embodiment, the g⁻NK cells are human autologous or allogeneic g⁻NK cells.

One embodiment provides a method of treating a subject (e.g., in need thereof) suspected of having cancer, comprising administering (e.g., an effective amount) a composition disclosed herein to the subject to thereby treat the subject. One embodiment provides a method of treating a subject (e.g., in need thereof) suspected of having a microbial infection, comprising administering a composition (e.g., an effective amount) disclosed herein to the subject to thereby treat the subject. Another embodiment provides a method of treating a subject (e.g., in need thereof) suspected of having a viral infection, comprising administering a composition (e.g., an effective amount) disclosed herein to the subject to thereby treat the subject. One embodiment further provides isolating g⁻NK cells from the subject. Another embodiment further comprises isolating g⁻NK cells and culturing the g⁻NK cells in a cell culture medium. One embodiment provides for isolating g⁻NK cells, culturing the g⁻NK cells in a cell culture medium, and preparing the composition comprising natural killer cells that do not express substantial FcRγ (g⁻NK cells). In one embodiment, IL-12, IL-15, IL-18, IL-2, and/or CCL5 is administered to a subject prior to isolating the g⁻NK cells. Another embodiment, the g⁻NK cells are isolated from lymphocytes comprising a population of natural killer cells containing a percentage of the g⁻NK cells. In one embodiment, the percentage of g⁻NK cells in the composition is more than 5% g⁻NK cells. In another embodiment, the percentage of g⁻NK cells in the composition is more than 10% g⁻NK cells. In another embodiment, the percentage of g⁻NK cells in the composition is more than 5% to 99% g⁻NK cells. In another embodiment, the percentage of g⁻NK cells is more than 10% to 80% g⁻NK cells. In one embodiment, a cell receptor is activated in the g⁻NK cells upon contact with an antibody. In one embodiment, the antibody is on a cell in the subject. In another embodiment, the antibody is on a cancer cell or on an infected cell. One embodiment provides further administering a composition of one or more therapeutic antibody. In one embodiment, the antibody can bind to an antigen on a microbe, virus, and/or cancer cell. In one embodiment, the antibody can bind a cancer marker. In another embodiment, the antibody can bind to an antigen or epitope produced by adenocarcinoma cells, carcinoma cells, breast cancer cells, cervical cancer cells, colon cancer cells, chondrosarcoma cells, dysplasia cells, fibrosarcoma cells, glioma cells, hepatoma cells, hyperplasia cells, leukemia cells, lymphoma cells, lung cancer cells, melanoma cells, myeloblastic cells, neuroblastoma cells, pancreatic cancer cells, prostate cancer cells, ovarian cancer cells, renal cell carcinoma cells, retinoblastoma cells, sarcoma cells, testicular cancer cells, uterine cancer cells, or a combination thereof. In another embodiment, the antibody can bind a antigen or epitope produced by adenocarcinoma cells, angiosarcoma cells, astrocytoma cells, basal cell carcinoma cells, bladder carcinoma cells, breast cancer cells, cervical cancer cells, colon carcinoma cells, chondrosarcoma cells, chronic lymphocytic leukemia cells, chronic myelocytic (granulocytic) leukemia cells, endotheliosarcoma cells, epithelial carcinoma cells, dysplasia cells, erythroleukemia cells, Ewing's tumor cells, fibrosarcoma cells, glioma cells, hepatoma cells, Hodgkin's lymphoma cells, hyperplasia cells, liposarcoma cells, leukemia cells, lymphoma cells, lung carcinoma cells, monocytic cells, melanoma cells, myeloblastic cells, myelomonocytic cells, myxosarcoma cells, neuroblastoma cells, non-Hodgkin's lymphoma cells, oligodendroglioma cells, pancreatic cancer cells, promyelocytic cells, prostate cancer cells, osteogenic sarcoma cells, ovarian cancer cells, renal cell carcinoma cells, retinoblastoma cells, small cell lung carcinoma cells, squamous cell carcinoma cells, testicular tumor cells, uterine cancer cells, Wilms' tumor cells, or a combination thereof. In a further embodiment, the antibody can bind a antigen or epitope produced by retroviruses, herpes viruses, arenaviruses, paramyxoviruses, adenoviruses, bunyaviruses, cornaviruses, filoviruses, flaviviruses, hepadnaviruses, orthomyoviruses, papovaviruses, picornaviruses, poxviruses, reoviruses, togaviruses, rhabdoviruses or a combination thereof. In another embodiment, the antibody can bind a antigen or epitope produced by human T-cell lymphotrophic viruses (HTLV) type I, human T-cell lymphotrophic viruses (HTLV) type II, human immunodeficiency virus (HIV)), herpes simplex viruses (HSV) type I, herpes simplex viruses (HSV) type II, Epstein-Barr viruses, cytomegaloviruses, lassa fever viruses, morbillivirus viruses, human respiratory syncytial viruses, pneumoviruses, hantaviruses, cornaviruses, Ebola viruses, hepatitis C viruses (HCV), yellow fever viruses, Japanese encephalitis viruses, hepatitis B viruses (HBV)), Sendai viruses, influenza virus A, influenza virus B, influenza virus C, papillomaviruses, rhinoviruses, enteroviruses, hepatitis A viruses, poxviruses, rotaviruses, rubella viruses, rabies viruses, or a combination thereof. In one embodiment, the antibody can bind a antigen or epitope produced by *Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholera, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella aborts, Brucella suis, Brucella melitensis, Mycoplasma* spp., *Rickettsia prowazeki, Rickettsia tsutsugumushi, Chlamydia* spp., *Helicobacter pylori* or combinations thereof. In one embodiment, the composition is administered in a therapeutically effective amount. In another embodiment, the administered composition alleviates one or more symptoms associated with a cancer or infection. In one embodiment, the administered compositions inhibits, reduces or suppresses cancer cell or viral replication. In one embodiment the administered composition releases cytokines and/or chemokines when contacted with an antibody that can bind a microbe, cancer cell or virus. In another embodiment, the administered composition kills a microbe, cancer cell or virus.

One embodiment provides a method of identifying g⁻NK cells comprising: identifying a subset of natural killer cells in a population of lymphocytes that do not express substantial FcRγ to thereby identify g⁻NK cells. In one embodiment, lymphocytes are obtained from a subject. In another embodiment, cells that do not express substantial FcRγ but do express at least one marker for natural killer cells are identified. In one embodiment, a subset of natural killer cells in a population of lymphocytes is identified comprising contacting a sample of lymphocytes with an antibody that binds to a natural killer cell-specific antigen. In one embodiment, the marker for natural killer cells is KIR, KIR2DL2/3, CD16, NKp30, NKp46 or a combination thereof. Another embodiment provides isolating the g⁻NK cells. In one embodiment, the cells are isolated by contacting the lymphocytes with a solid surface to which anti-NCR antibodies are bound. In another embodiment, the cells are isolated by contacting the lymphocytes with a solid surface to which anti-NCR antibodies are bound and removing the unbound cells. In one embodiment, the isolating comprises applying the lymphocytes to column comprising a substrate to which anti-NCR antibodies are bound. In one embodiment, the isolating comprises applying the lymphocytes to column comprising a substrate to which anti-NCR antibodies are bound and collecting the eluent. In another embodiment, the lymphocytes comprise or consist essentially of natural killer cells. In one embodiment, the lymphocytes are a population of natural killer cells containing a percentage of the g⁻NK cells. In another embodiment, the percentage of g⁻NK cells is more than 5% g⁻NK cells. In one embodiment, the percentage of g⁻NK cells is more than 10% g⁻NK cells. In another embodiment, the percentage of g⁻NK cells is 5% to 99% g⁻NK cells, or any numerical value between 5% and 99%. One embodiment comprises identifying whether a lymphocyte sample from a subject comprises g⁻NK cells. In one embodiment, a sample of lymphocytes is obtained from a subject for identifying whether the sample comprises g⁻NK cells. One embodiment comprises administering a therapeutic antibody to a subject when g⁻NK cells are identified in a sample from a subject. In another embodiment, unnecessary treatment of a subject is avoided when g⁻NK cells are not identified in a sample from a subject.

BRIEF DESCRIPTION OF THE FIGURES

FIG. 1E illustrates expression of FcRγ and CD3ζ in NK cells in different donor samples. Dot plots show NK cell ($CD56^+CD3^-CD14^-CD19^-$) expression of FcRγ (upper panels) and CD3ζ (lower panels) from 4 representative donor samples obtained from leukocyte reduction filters.

FIGS. 2A-F illustrate results from analysis of enriched FcRγ-deficient NK cells indicating that FcRγ-deficiency is regulated at the transcriptional level. (A) Dot plots show expression of indicated KIRs by $CD56^{dim}$ $CD3^-CD14^-CD19^-NK$ cells with respect to FcRγ expression from 3 donors. Numbers indicate the percentage of cells in each quadrant. (B) Immunoblot analysis of total cell lysates prepared from NK clones derived from enriched conventional NK (lane 1) or FcRγ-deficient NK cells (g⁻NK: lanes 2 and 3). FIG. 2C shows the relative quantities of FcRγ and CD3ζ mRNA from donor NK cells as determined by RT-qPCR, where FcRγ and CD3ζ mRNA expression levels have been normalized to GAPDH expression and expressed relative to total NK cells. FIG. 2D shows the relative expression level of FcRγ mRNA from enriched NK cell clones as determined by RT-qPCR, where the FcRγ expression level is normalized to GAPDH expression and expressed relative to NK clone #2. Samples included RNA from total NK, enriched conventional NK and enriched g⁻NK cells as indicated. Data are representative of at least 2 independent experiments. FIG. 2E shows that NKG2A is less frequently expressed on FcRγ-deficient NK cells than on conventional NK cells. Dot plots show expression of NKG2A by $CD56^{dim}$ $CD3^-CD14^-CD19^-NK$ cells with respect to FcRγ expression from 3 donors. Numbers indicate the percentage of cells in each quadrant. FIG. 2F illustrates that human NK cell clones show homogeneity with respect to FcRγ and KIR expression. Dot plots show FcRγ and KIR2DL2/3 expression in several representative $CD56^+CD3^-$ NK cell clones generated from enriched g⁻NK cell cultured under limiting dilution conditions.

FIG. 3A illustrates flow cytometric analysis of surface expression of NKp46 and NKp30 on conventional NK (NK: dotted line) and g⁻NK cells (solid line) from four representative donor samples. Upper and lower numbers indicate median fluorescence intensities of conventional and g⁻NK cells, respectively. FIG. 3B illustrates flow cytometric analysis of surface expression of CD16 on conventional NK (NK: dotted line) and g⁻NK cells (solid line) from four representative donor samples. Upper and lower numbers indicate median fluorescence intensities of conventional and g⁻NK cells, respectively. Shaded peaks are from control staining. FIG. 3C provides histograms showing patterns of NKG2C expression in conventional NK (NK: dotted line) and g⁻NK cells (solid line) from four representative donors. Upper and lower percentages indicate the frequency of $NKG2C^+$ NK cells within conventional or g⁻NK cell populations, respectively. FIG. 3D provides histograms showing representative samples for the expression of indicated surface markers on conventional NK (NK: dotted line) and g⁻NK cells (solid line) FIG. 3E provides histograms showing representative samples for the expression of cytolytic effector molecules on conventional NK (NK: dotted line) and g⁻NK cells (solid line). Upper and lower numbers indicate median fluorescence intensities of conventional and g⁻NK cells, respectively. FIG. 3F shows that KIR2DL4 is not expressed on g⁻NK cells after 7 days in culture. PBMCs (2.5×10⁶ cells/mL) were cultured for 7 days in the presence of 100 U/mL of IL-2 in 96-well round bottom wells. Dot plots show expression of KIR2DL4 by $CD56^+$ NK cells with respect to FcRγ expression from 2 donors at day 0 (D0) and day 7 (D7) culture. Numbers indicate the percentage of cells in each quadrant. FIG. 3G illustrates that g⁻NK and conventional NK cells display similar expression profiles of several cell surface receptors. Histograms show representative samples for the expression of indicated surface markers on g⁻NK (solid line) and conventional NK cells (NK: dotted line). Upper and lower numbers indicate median fluorescence intensities of conventional and g⁻NK cells, respectively.

FIG. 4A shows dot plots from a representative sample depicting relative percentages (inserted numbers) of conventional or g⁻NK cells that produced IFN-γ in response to crosslinking by immobilized anti-CD 16. Graphs show percentages of cytokine production by conventional (NK) and g⁻NK cells from different donors (IFN-γ, n=17; TNF-α, n=14). Dots connected by a line represent data obtained from the same donor sample. FIG. 4B shows dot plots from a representative sample depicting relative percentages (inserted numbers) of conventional or g⁻NK cells that produced TNF-α in response to crosslinking by immobilized anti-CD16. Graphs show percentages of cytokine production by conventional (NK) and g⁻NK cells from different donors (IFN-γ, n=17; TNF-α, n=14). Dots connected by a line represent data obtained from the same donor sample. FIG. 4C graphically illustrates the percentages of conventional or g⁻NK cells that produced the indicated cytokines following stimulation with antibody-coated SCC4 cells (IFN-γ, n=10; TNF-α, n=10). FIG. 4D graphically illustrates the percentages of conventional and g⁻NK cells that displayed the degranulation marker CD107a following CD16 crosslinking (left) (n=10) or incubation with antibody-coated SCC4 cells (right) (n=10). FIG. 4E graphically illustrates the percentages of conventional or g⁻NK cells that expressed IFN-γ (n=14) or CD107a (n=11) following incubation with K562 tumor cells. *, P<0.01; , P<0.001; *, P<0.0001; ns: not significant. FIG. 4F graphically illustrates the percentages of conventional or g⁻NK cells that expressed IFN-γ (n=14) or CD107a (n=11) following incubation with 721.221 tumor cells. *, P<0.01; , P<0.001; *, P<0.0001; ns: not significant. FIG. 4G shows that g⁻NK cells produce cytokines abundantly in response to antibody-coated P815 tumor cells. Line graphs show percentages of conventional or g⁻NK cells that produced indicated cytokines following stimulation with antibody-coated P815 cells (IFN-γ, n=13; TNF-α, n=13). Dots connected by a line represent data obtained from the same donor sample. , P<0.001; *, P<0.0001. FIG. 4H shows that IFNγ is not produced by human NK cells in response to SCC4 tumor cells in the absence of antibody pre-coating as illustrated by dot plots from one representative sample depicting relative percentages (inserted numbers) of conventional or g⁻NK cells that produced IFN-γ following stimulation by SCC4 cells with or without antibody pre-coating. FIG. 4I shows that IFNγ is not produced by human NK cells in response to SCC4 tumor cells in the absence of antibody pre-coating as illustrated by the percentages of conventional or g⁻NK cells that produced indicated cytokines following stimulation with SCC4 cells without antibody pre-coating (IFN-γ, n=10; TNF-α, n=10).

FIGS. 5A-E show that g⁻NK cells exist long-term at nearly constant levels. FIG. 5A is a bar graph that shows absolute numbers of cells for indicated subsets within $1 \times 10^6$ lymphocytes from a representative individual determined by flow cytometry. Follow-up samples were collected at 5 months (black bars) after initial sample collection (white bars). FIG. 5B graphically illustrates the percentages of g⁻NK cells among $CD56^{dim}$ NK cells in donor samples collected at the initial time point and 4 or 5 months later from healthy donors (n=17). Dots connected by a line designate samples collected from the same individual. FIG. 5C provides dot plots showing the expression of KIR2DL1 and KIR2DL2/3 on conventional NK or g⁻NK cells collected at indicated time points for two representative individuals. Numbers indicate the percentage of cells in each quadrant. FIGS. 5D1-9 show that the absolute number of g⁻NK cells is maintained over a 5-month period. Bar graphs show absolute numbers of cells for indicated subsets within $1 \times 10^6$ lymphocytes from 9 donors determined by flow cytometry. Follow-up samples were collected at 4 or 5 months as indicated (black bars) after initial sample collection (white bars). FIG. 5E illustrates that the expression of activation receptors on g⁻NK cells does not change over a 5-month period. Dot plots show expression of indicated markers by $CD56^{dim}$ $CD3^-CD14^-CD19^-$NK cells with respect to FcRγ expression from donor #211.

FIGS. 7A-D show that g⁻NK cells display enhanced effector functions in response to HCMV-infected cells in the presence of HCMV-specific Abs. PBMCs were cultured with mock- or HCMV-infected MRC-5 cells as indicated. (A and B) Flow cytometric analysis of IFN-γ production by conventional NK and g⁻NK cells from a representative donor following 3 days of incubation. Numbers represent the relative percentage of IFN-γ⁺ NK cells (left panels). Line graphs show the percentages of conventional NK (○) or g⁻NK (●) cells that produced IFN-γ from several donors in the absence (A) or presence (B) of autologous plasma or purified IgG (Ab) as indicated. Circles connected by a line designate the same donor sample. (C) Production of TNF-α by conventional NK or g⁻NK cells in the presence or absence of autologous plasma or purified IgG from several donors. (D) Expression of CD107a in the presence or absence of autologous plasma or purified IgG following 2 days of incubation. *p<0.05, **p<0.01.

DETAILED DESCRIPTION

Figure 1A:
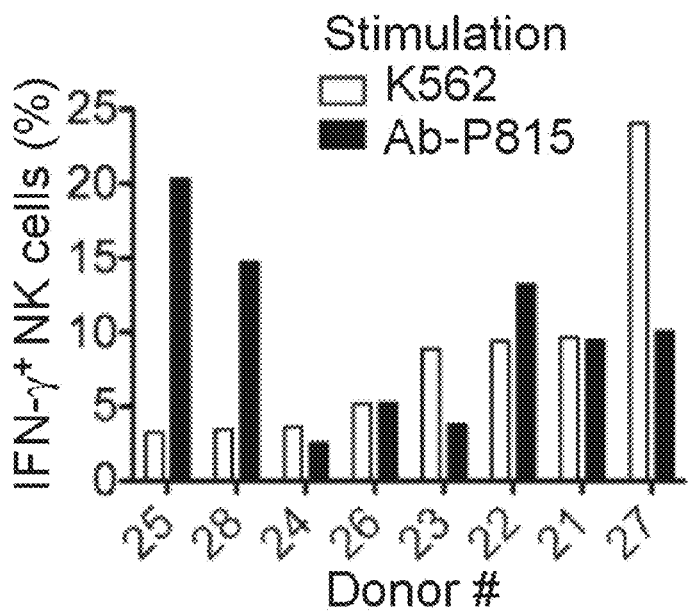
FIGS. 1A-E illustrate identification of Fc receptor γ-chain deficient human NK cells in healthy individuals. (A) Donor PBMCs were stimulated with K562 tumor cells or antibody-coated P815 cells. (B) Donor PBMCs were not stimulated or were stimulated with anti-CD16 monoclonal antibodies. Bar graphs show percentages of NK cells ($CD56^{dim}$ $CD3^-$) that produced IFN-γ following indicated stimulation from 8 representative donor samples from leukocyte reduction filters, arranged according to K562 responsiveness. (C) Dot plots show NK cell ($CD56^+CD3^-CD14^-CD19^-$) expression of FcRγ (upper panels) and CD3ζ (lower panels) from 2 representative donors. (D) Donor samples from healthy subjects and leukocyte reduction filters were categorized according to percentages of FcRγ-deficient NK cells among the $CD56^{dim}CD3^-CD14^-CD19^-NK$ cell population (n=122).

As described herein, the invention relates to a previously unknown population of NK cells that are deficient for the signaling adaptor γ-chain, yet display enhanced Fc receptor-dependent activity. Compared to conventional NK cells that express the γ-chain, γ-deficient NK cells (herein termed ᵞ⁻NK cells or g-NK cells) produce significantly greater amounts of cytokines (IFN-γ and TNF-α) and chemokines (MIP-1α and MIP-1β) upon stimulation through the Fc receptor CD16. Analyses of healthy donor samples indicate that g⁻NK cells can mediate enhanced anti-cancer activity upon encountering antibody-coated tumor cells in patients receiving therapeutic anti-tumor mAb. Interestingly, g⁻NK cells have been found in only one third of the healthy human donors analyzed.

Natural Killer Cells

Natural killer (NK) cells are innate lymphocytes important for mediating anti-viral and anti-cancer immunity through cytokine and chemokine secretion, and through the release of cytotoxic granules (Vivier et al. Science 331 (6013):44-49 (2011); Caligiuri, Blood 112(3):461-469 (2008); Roda et al., Cancer Res. 66(1):517-526 (2006)).

While significant advances have been made in cancer treatment by use of antibodies directed against cancer antigens, the responsiveness of patients to such antibodies varies. Investigation of such variable responses has typically focused on the direct inhibitory effects of these antibodies on the tumor cells (e.g. inhibition of growth factor receptors and the subsequent induction of apoptosis) and the in vivo effects of these antibodies may be more complex and may involve the host immune system. For example, the mechanism of action of such anti-cancer antibodies may include one or more of the following: antibody-dependent cellular cytotoxicity (ADCC), antibody-dependent cytokine/chemokine production, and complement-dependent cytotoxicity (CMC).

Antibody-dependent cellular cytotoxicity and antibody-dependent cytokine/chemokine production are primarily mediated by the specialized subset of lymphocytes, natural killer (NK) cells. NK cells are effector cells that comprise the third largest population of lymphocytes and are important for host immuno-surveillance against tumor and pathogen-infected cells.

Upon activation, NK cells produce cytokines and chemokines abundantly and at the same time exhibit potent cytolytic activity. Activation of NK cells can occur through the direct binding of NK cell receptors to ligands on the target cell, as seen with direct tumor cell killing, or through the crosslinking of the Fc receptor (CD 16; FcγRIII) by binding to the Fc portion of antibodies bound to an antigen-bearing cell. This CD16 engagement (CD16 crosslinking) initiates NK cell responses via intracellular signals that are generated through one, or both, of the CD16-associated adaptor chains, FcRγ or CD3ζ. Triggering of CD16 leads to phosphorylation of the γ or ζ chain, which in turn recruits tyrosine kinases, syk and ZAP-70, initiating a cascade of signal transduction leading to rapid and potent effector functions. The most well-known effector function is the release of cytoplasmic granules carrying toxic proteins to kill nearby target cells through the process of antibody-dependent cellular cytotoxicity. CD16 crosslinking also results in the production of cytokines and chemokines that, in turn, activate and orchestrate a series of immune responses.

This release of cytokines and chemokines can play a role in the anti-cancer activity of NK cells in vivo. NK cells also have small granules in their cytoplasm containing perforin and proteases (granzymes). Upon release from the NK cell, perforin forms pores in the cell membrane of targeted cells through which the granzymes and associated molecules can enter, inducing apoptosis. The fact that NK cells induce apoptosis rather than necrosis of target cells is significant—necrosis of a virus-infected cell would release the virions, whereas apoptosis leads to destruction of the virus inside the cells.

However, unlike T and B lymphocytes, NK cells are thought to have only a limited capacity for target recognition using germline-encoded activation receptors (Bottino et al., Curr Top Microbiol Immunol. 298:175-182 (2006); Stewart et al., Curr Top Microbiol Immunol. 298:1-21 (2006)). NK cells express the activating Fc receptor CD 16, which recognizes IgG-coated target cells, thereby broadening target recognition (Ravetch & Bolland, Annu Rev Immunol. 19:275-290 (2001); Lanier Nat. Immunol. 9(5):495-502 (2008); Bryceson & Long, Curr Opin Immunol. 20(3):344-352 (2008)).

The expression and signal transduction activity of several NK cell activation receptors requires physically associated adaptors, which transduce signals through immunoreceptor tyrosine-based activation motifs (ITAMs). Among these adaptors, FcRγ and CD3ζ chains can associate with CD16 and natural cytotoxicity receptors (NCRs) as either disulfide-linked homo-dimers or hetero-dimers, and these chains have been thought to be expressed by all mature NK cells.

As described herein, a novel subset of human NK cells has been identified that is deficient for the FcRγ-chain, and displays specialized immune functions. These novel NK cells are referred to herein as g⁻NK cells. The g⁻NK cells express the signaling adaptor ζ-chain abundantly, but are deficient in the expression of the signaling adaptor γ-chain. Compared to conventional NK cells, these γ-deficient g⁻NK cells exhibit dramatically enhanced activity when activated by antibodies. For example, the g⁻NK cells can be activated by antibody-mediated crosslinking of CD16 or by antibody-coated tumor cells.

The g⁻NK cells described herein not only produce significantly greater amounts of cytokines (IFN-γ and TNF-α) and chemokines (MIP-1α, MIP-1β and RANTES), but also display higher degranulation responses. The g⁻NK cells provide high expression of Granzyme B, a component of natural killer cell cytotoxic machinery. Moreover, the g⁻NK cells have a prolonged lifespan, compared to conventional NK cells, and their presence is maintained long-term. They are functionally and phenotypically stable.

The g⁻NK cell subset of natural killer cells is found only in about one-third of the population, and among the individuals with this subset, the percentage of g⁻NK cells within the NK cell compartment is variable. Thus, the degree to which an individual has such a subset of NK cells identifies patients that will be, or are, responsive to antibody-based therapy.

One aspect of the invention is therefore a method of identifying a subject responsive to cancer therapy that involves detecting whether a percentage of the patient's natural killer cells fail to express FcRγ. Such failure to express FcRγ identifies a subject who will be responsive to antibody-based cancer therapy. In some embodiments, the method also includes detecting whether the patient's natural killer cells that fail to express FcRγ do express CD3ζ.

Sequences for various FcRγ and CD3ζ proteins and nucleic acids are available from the National Center for Biotechnology Information (NCBI) database (see, e.g., the website at ncbi.nlm.nih.gov). For example, an amino acid sequence for FcRγ (Homo sapiens, also called the High affinity immunoglobulin gamma Fc receptor I) is available in the NCBI database as accession number NP_004097.1 (GI:4758344), and is reproduced below as SEQ ID NO:1.

```
 1  MIPAVVLLLL LLVEQAAALG EPQLCYILDA ILFLYGIVLT
41  LLYCRLKIQV RKAAITSYEK SDGVYTGLST RNQETYETLK
61  HEKPPQ
```

An amino acid sequence for the human CD3ζ (*Homo sapiens*) is available in the NCBI database as accession number ABQ28690.1 (GI:146399947), and is reproduced below as SEQ ID NO:2.

```
  1  AILQAQLPIT EAQSFGLLDP KLCYLLDGIL FIYGVILTAL

41  FLRVKFSRSA DAPAYQQGQN QLYNELNLGR REEYDVLDKR

81  RG
```

As described herein, reduced or absence of expression of FcRγ is a surprisingly effective marker for the g⁻NK cell subset of natural killer cells that produce significantly greater amounts of cytokines (IFN-γ and TNF-α) and chemokines (MIP-1α, MIP-1β and RANTES), higher degranulation responses and have a prolonged lifespan. The g⁻NK cell subset of natural killer cells express CD3ζ abundantly. Thus, the g⁻NK cell subset of natural killer cells can be identified by detecting natural killer cells that express CD3ζ but exhibit substantially low or no expression of FcRγ.

Detecting, Identifying and/or Isolating g-Natural Killers Cells

Natural killer can be identified by any convenient procedure, for example, by their expression patterns. For example, mature NK cells express known substances or markers that can be detected by procedures available in the art. A typical human marker profile includes, for example, NKG2A, NKG2D, NKp30, NKp44, NKp46, CD56, CD161, 2B4, NTB-A, CRACC, DNAM-1, CD69, CD25 and/or NKp44. Other markers for natural killer cells include KIRs. A typical mouse marker profile includes, for example, NK1.1, CD122, LY49 Family (Ly49A, Ly49C, Ly49D, Ly49E, Ly49F, Ly49G, Ly49H, and Ly49I), and/or NKG2A/C/E. NK cells do not express T-cell antigen receptors (TCR), CD3ζ or surface immunoglobulins (Ig) B cell receptor, but generally express the surface marker CD56 in humans.

The g⁻NK cell subset of natural killer cells can be detected by observing whether FcRγ is expressed by a subpopulation of natural killer cells. The natural killer cells that do not express FcRγ are g⁻NK cells. In some embodiments it may be useful to detect expression of any of the above-mentioned other natural killer cell markers as a positive identifier that the cell is a natural killer cell while also confirming that the cell does not express FcRγ. Expression of a natural killer cell surface marker that correlates with the expression of FcRγ (or lack thereof) can be detected by any available procedure that does not injure the cells. For example, the g⁻NK cells can be detected, identified and/or isolated by flow cytometry by use of such a cell surface marker that correlates with FcRγ expression.

The CD3ζ and/or FcRγ proteins are intracellular proteins that are not easily detected unless the cells are treated to allow intracellular proteins to be detected, for example, by fixation and permeabilization. While such treatment can be used to confirm the identity of a substantially pure population of cells, in many cases it is preferable to use cell-surface markers that can be detected without injuring the cells when identifying and isolating g⁻NK cells. For example, surface markers such as KIR (Killer cell immunoglobulin-like receptors) can be used to identify and isolate mature NK cells, and Natural cytotoxicity receptors (NCR) which are normally expressed on NK cells, but are not expressed on g⁻NK cells can be used to identify and isolate g⁻NK cells.

Antibodies and other binding entities can be used to detect expression levels of marker proteins (e.g., KIR and/or NCR), and isolate the g⁻NK cells. For example, in some embodiments, antibodies specific for FcRγ-expressing cells (e.g., antibodies specific for a cell surface marker such as NCR that correlates with FcRγ expression) can be bound to a solid substrate, natural killer cells can be contacted with the antibody-substrate, and cells that do not bind to the antibodies are collected. Other methods available to those of skill in the art can also be employed.

Such antibodies and binding entities can be prepared by available methods. For example, KIR and/or NCR, amino acid sequences, including those illustrated herein, can be used to make KIR and/or NCR antibodies and binding entities.

An amino acid sequence for a human KIR polypeptide (*Homo sapiens*) is available in the NCBI database as accession number NP_037421.2 (GI:134268644), and is reproduced below as SEQ ID NO:3.

```
  1  MSLMVVSMAC VGLFLVQRAG PHMGGQDKPF LSAWPSAVVP

41  RGGHVTLRCH YRHRFNNFML YKEDRIHIPI FHGRIFQESF

81  NMSPVTTAHA GNYTCRGSHP HSPTGWSAPS NPVVIMVTGN

121  HRKPSLLAHP GPLVKSGERV ILQCWSDIMF EHFFLHKEGI

161  SKDPSRLVGQ IHDGVSKANF SIGPMMLALA GTYRCYGSVT

181  HTPYQLSAPS DPLDIVVTGP YEKPSLSAQP GPKVQAGESV

241  TLSCSSRSSY DMYHLSREGG AHERRLPAVR KVNRTFQADF

281  PLGPATHGGT YRCFGSFRHS PYEWSDPSDP LLVSVTGNPS

301  SSWPSPTEPS SKSGNPRHLH ILIGTSVVII LFILLLFFLL

361  HLWCSNKKNA AVMDQEPAGN RTANSEDSDE QDPEEVTYAQ

401  LDHCVFTQRK ITRPSQRPKT PPTDTILYTE LPNAKPRSKV

421  VSCP
```

When making antibodies, the extracellular portion of the KIR polypeptide can be employed. Thus, in some embodiments, a KIR antigen may not include the signal peptide (amino acids 1-21) and/or the transmembrane region (amino acids 341-360).

Other human KIR polypeptide sequences are available, for example, in the NCBI database with any of the following accession numbers: NP_703144.2 (GI:46488946), NP_001229796.1 (GI:338968852), NP_001229796.1 (GI:338968852), NP_006728.2 (GI:134268642), NP_065396.1 (GI: 11968154), NP_001018091.1 (GI:66267727), NP_001077008.1 (GI:134133244), NP_036444.1 (GI:6912472), NP_055327.1 (GI:7657277), NP_056952.2 (GI:71143139), NP_036446.3 (GI:116517309), NP_001074239.1 (GI:124107610), NP_002246.5 (GI:124107606), NP_001074241.1 (GI: 124107604), NP_036445.1 (GI:6912474) or a combination thereof. Any such KIR polypeptides can be used as antigens to make antibodies. The antigens employed can include an extracellular region of the KIR protein, and can exclude other portions of the KIR protein (e.g., the signal peptide, an intracellular domain, and/or a transmembrane domain).

An amino acid sequence for a human NCR polypeptide (*Homo sapiens*) is available in the NCBI database as accession number NP_004819.2 (GI:153945782), and is reproduced below as SEQ ID NO:4.

```
  1  MAWRALHPLL LLLLLFPGSQ AQSKAQVLQS VAGQTLTVRC

41  QYPPTGSLYE KKGWCKEASA LVCIRLVTSS KPRTMAWTSR
```

```
 61  FTIWDDPDAG FFTVTMTDLR EEDSGHYWCR IYRPSDNSVS

121  KSVRFYLVVS PASASTQTSW TPRDLVSSQT QTQSCVPPTA

161  GARQAPESPS TIPVPSQPQN STLRPGPAAP IALVPVFCGL

201  LVAKSLVLSA LLVWWGDIWW KTMMELRSLD TQKATCHLQQ

241  VTDLPWTSVS SPVEREILYH TVARTKISDD DDEHTL
```

As indicated above for KIR, when making antibodies, the extracellular portion of the NCR polypeptide can be employed. Thus, in some embodiments, a NCR antigen may not include the signal peptide (amino acids 1-21) and/or the transmembrane region (amino acids 193-213).

Other NCR polypeptide sequences are available and can be used to make antibodies. For example, the NCBI database provides a number human NCR polypeptide sequences with the following accession numbers: O14931.1 (GI:47605770), O95944.2 (GI:251757303), O76036.1 (GI:47605775), NP_001138939.1 (GI:224586865), and/or NP_001138938.1 (GI:224586860). Any such NCR polypeptides can be used as antigens to make antibodies. The antigens employed can include an extracellular region of the NCR protein, and can exclude other portions of the NCR protein (e.g., the signal peptide, an intracellular domain, and/or a transmembrane domain).

Suitable antibodies may include polyclonal, monoclonal, fragments (such as Fab fragments), single chain antibodies and other forms of specific binding molecules.

Briefly, methods for detecting, identifying and/or isolating g⁻NK cells can include contacting a cell population, or cell sample, with an antibody specific to NCR, and removing any cells that form a complex with the anti-NCR antibodies. In other embodiments, methods for detecting, identifying and/or isolating g⁻NK cells can include contacting a cell population, or a cell sample, with an antibody to a natural killer cell specific marker, such as KIR, and an antibody specific for NCR; identifying, detecting and/or isolating cells that form a complex with the natural killer-specific antibody, to thereby identify, detect or isolate natural killer cells in the population or sample; and identifying, detecting and/or isolating the natural killer cells that do not form substantially any complex with the anti-NCR antibodies. Anti-FcRγ antibodies can be used on an aliquot of a population of natural kills cells treated (e.g. fixed) to permit antibody detection of intracellular proteins to confirm that a population of cells does not express FcRγ.

In some embodiments, a signal from the complex between the natural killer cells and the antibody to a natural killer cell specific marker is detected (e.g., KIR). However, when the natural killer cells are g⁻NK cells substantially no signal from an NCR protein-antibody complex (or FcRγ protein-antibody complex) is detected because substantially no NCR protein-antibody complex (or FcRγ protein-antibody complex) forms.

In some embodiments, natural killer cells are first isolated and then sorted using available procedures—those cells that express substantially no NCR are collected.

For example, a population of lymphocytes or peripheral blood mononuclear cells (PBMCs) can be obtained. Natural killer cells expressing one or more natural killer cell-specific markers are isolated from the cell population. For example, the natural killer cells may be identified as those expressing typical human natural killer cell markers such as KIR, NKG2A, NKG2D, NKp30, NKp44, NKp46, CD56, and CD161. For studies involving mice, natural killer cells can be identified and/or isolated using typical mouse markers such as NK1.1, CD 122, LY49 Family (Ly49A, Ly49C, Ly49D, Ly49E, Ly49F, Ly49G, Ly49H, and Ly49I), or NKG2A/C/E.

Once the population of cells is a substantially pure population of natural killer cells, the g⁻NK cells are identified as those that do not express NCR (or FcRγ) protein. For example, the population of natural killer cells can be sorted by flow cytometry using an antibody specific for NCR protein. The cells that are labeled by the anti-NCR antibodies are discarded and the cells that are not labeled by the anti-FcRγ antibodies are retained as g⁻NK cells. Alternatively, the population of natural killer cells can be contacted with a solid substrate to which anti-NCR antibodies are bound. The cells that do not bind are the desired g⁻NK cells. In another embodiment, the population of natural killer cells can be contacted with magnetic beads to which anti-NCR antibodies are bound, after incubation the magnetic beads are removed from the cell population, leaving the g⁻NK cells as a substantially pure population of cells.

As illustrated herein, signals from labeled antibodies can be used for detection, identification and isolation of different cell types. A signal from an antibody specific for natural killer cells or a signal from an antibody specific for NCR (FcRγ) can be detected, for example, by using a label that is directly or indirectly attached to the antibody. Such an antibody with a directly attached label can be an antibody with a covalently attached reporter molecule.

As used herein, a "reporter molecule" is a molecule that provides an analytically detectable signal, allowing the detection of antigen-bound antibody. In some embodiments, detection is preferably at least relatively quantifiable, to allow determination of the amount of antigen (and/or cells expressing such an antigen) in the sample. Quantification of antigen (or cells expressing the antigen) may be calculated in absolute terms, or may be by comparison with a standard (or series of standards) containing a known normal level of antigen (and/or cells expressing such an antigen).

Many commonly used reporter molecules in this type of assay are either enzymes or fluorophores. For example, labels employed for flow cytometry detection and sorting of cells are often fluorescent labels or magnetic beads. In some embodiments, a second antibody can be used that binds to the anti-FcRγ antibody or antibody specific for natural killer cells. The reporter molecule can then be on the second antibody.

Fluorescent compounds, such as fluorescein or rhodamine, may be chemically coupled to antibodies without altering their binding capacity. When activated by illumination with light of a particular wavelength, the fluorophore-labeled antibody absorbs the light energy, inducing a state of excitability in the molecule, followed by emission of the light at a characteristic longer wavelength. The emission appears as a characteristic color visually detectable with a light microscope.

While fluorophores are often employed, other types of reporter molecules can also be employed including enzymes, magnetic beads, radioactive isotopes, enzymes and the like. Commonly used enzymes include horseradish peroxidase, glucose oxidase, beta-galactosidase and alkaline phosphatase, among others. The enzyme substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. In all cases, the enzyme-labeled antibody is added to the first antibody-antigen complex and allowed to bind to the complex, and then the excess reagent is washed away. A solution containing the appropriate substrate is then added to the tertiary complex of antibody-antigen-labeled antibody. The substrate reacts with the enzyme linked to the second antibody, giving a qualitative visual signal, which may be further quantified, usually spectrophotometrically, to give an evaluation of the amount of antigen that is present in the serum sample.

Compositions and Methods

Another aspect of the invention is a composition including g$^-$NK cells. Such a composition of g$^-$NK cells can include a pharmaceutically acceptable carrier or vehicle.

A pharmaceutically acceptable carrier or vehicle for such g$^-$NK cells is any non-toxic aqueous solution in which the g$^-$NK cells can be maintained, or remain viable, for a time sufficient to allow administration of live g$^-$NK cells. For example, the pharmaceutically acceptable carrier or vehicle can be a saline solution or buffered saline solution. The pharmaceutically acceptable carrier or vehicle can also include various bio materials that may increase the efficiency of g$^-$NK cells. Cell vehicles and carriers can, for example, include polysaccharides such as methylcellulose (M. C. Tate, D. A. Shear, S. W. Hoffman, D. G. Stein, M. C. LaPlaca, *Biomaterials* 22, 1113, 2001, which is incorporated herein by reference in its entirety), chitosan (Suh J K F, Matthew H W T. *Biomaterials,* 21, 2589, 2000; Lahiji A, Sohrabi A, Hungerford D S, et al., *J Biomed Mater Res,* 51, 586, 2000, each of which is incorporated herein by reference in its entirety), N-isopropylacrylamide copolymer P(NIPAM-co-AA) (Y. H. Bae, B. Vernon, C. K. Han, S. W. Kim, *J. Control. Release* 53, 249, 1998; H. Gappa, M. Baudys, J. J. Koh, S. W. Kim, Y. H. Bae, *Tissue Eng.* 7, 35, 2001, each of which is incorporated herein by reference in its entirety), as well as Poly(oxyethylene)/poly(D,L-lactic acid-co-glycolic acid) (B. Jeong, K. M. Lee, A. Gutowska, Y. H. An, Biomacromolecules 3, 865, 2002, which is incorporated herein by reference in its entirety), P(PF-co-EG) (Suggs L J, Mikos A G. *Cell Trans,* 8, 345, 1999, which is incorporated herein by reference in its entirety), PEO/PEG (Mann B K, Gobin A S, Tsai A T, Schmedlen R H, West J L., *Biomaterials,* 22, 3045, 2001; Bryant S J, Anseth K S. *Biomaterials,* 22, 619, 2001, each of which is incorporated by reference in its entirety), PVA (Chih-Ta Lee, Po-Han Kung and Yu-Der Lee, *Carbohydrate Polymers,* 61, 348, 2005, which is incorporated herein by reference in its entirety), collagen (Lee C R, Grodzinsky A J, Spector M., *Biomaterials* 22, 3145, 2001, which is incorporated herein by reference in its entirety), alginate (Bouhadir K H, Lee K Y, Alsberg E, Damm K L, Anderson K W, Mooney D J. *Biotech Prog* 17, 945, 2001; Smidsrd O, Skjak-Braek G., *Trends Biotech,* 8, 71, 1990, each of which is incorporated herein by reference in its entirety), etc. and they are used as a cell carrier for cellular treatment in the field of tissue engineering.

In some embodiments, the g$^-$NK cells can be present in the composition in an effective amount. An effective amount of activated g$^-$NK cells can vary depending on the patient, as well as the type, severity and extent of disease. Thus, a physician can determine what an effective amount is after considering the health of the subject, the extent and severity of disease, and other variables.

In certain embodiments of the invention, a "therapeutically effective amount" is the amount of a composition of the invention that reduces the severity, the duration and/or the symptoms associated with cancer, viral infection, microbial infection, or septic shock in an animal. In other embodiments, effective amount for cytotoxicity is defined as amount of g$^-$NK cell that is able to inhibit or reduce the growth of cancer, viral and microbial cells. In some embodiments, an effective amount of g$^-$NK cells is about $10^6$ to about $10^{12}$ cells, or about $10^8$ to about $10^{11}$ cells, or about $10^9$ to about $10^{10}$ cells. Such an amount can be administered to a cancer patient.

The composition can include increased percentages of g$^-$NK cells relative to natural populations of natural killer cells. For example, the composition can include 20%, 30%, 40%, 50%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or substantially 100% g$^-$NK cells.

In some embodiments, the g$^-$NK cells are administered to a subject soon after isolation. In other embodiments, the g$^-$NK cells are stored or expanded by growth in culture prior to administration.

The g$^-$NK cells can be can be administered to a subject by any convenient route including parenteral routes such as subcutaneous, intramuscular, intravenous, and/or epidural routes of administration.

In some embodiments, the g$^-$NK cells can be preserved at ultra low temperature before the administration to a patient. The g$^-$NK cells can also be preserved at ultra low temperature after isolation from a mammalian subject. For example, lymphocytes or another source of g$^-$NK cells can be isolated, stored at ultra low temperature and then processed to yield isolated g$^-$NK cells. Alternatively, the lymphocytes or another source of g$^-$NK cells can be isolated, processed to yield g$^-$NK cells and then stored at ultra-low temperature.

A typical method for the preservation at ultra low temperature in small scale is described, for example, in U.S. Pat. No. 6,0168,991. For small-scale, cells can be preserved at ultra low temperature by low density suspension (e.g., at a concentration of about $200 \times 10^6$/ml) in 5% human albumin serum (HAS) which is previously cooled. An equivalent amount of 20% DMSO can be added into the HAS solution. Aliquots of the mixture can be placed into vials and frozen overnight inside an ultra low temperature chamber at about −80° C.

The g$^-$NK cells can be employed in methods for treating cancer, viral infections, bacterial infections, and other disease states. The g$^-$NK cells can be administered to a subject to treat any disease or disorder responsive to cytokines and/or the release of natural killer cell cytoplasmic granules. For example, the disease or disorder can be responsive to cytokines such as gamma interferon (IFN-γ), tumor necrosis factor alpha (TNF-α), and/or GM-CSF.

Diseases that the compositions and methods described herein can treat include microbial infection such as a viral infection, yeast infection, fungal infection, protozoan infection and/or bacterial infection.

By a "viral infection" is meant an infection caused by the presence of a virus in the body. Viral infections include chronic or persistent viral infections, which are viral infections that are able to infect a host and reproduce within the cells of a host over a prolonged period of time-usually weeks, months or years, before proving fatal. Viruses giving rise to chronic infections that which may be treated in accordance with the present invention include, for example, the human papilloma viruses (HPV), Herpes simplex, and other herpes viruses, the viruses of hepatitis B and C as well as other hepatitis viruses, human immunodeficiency virus, and the measles virus, all of which can produce important clinical diseases. Prolonged infection may ultimately lead to the induction of disease which may be, e.g., in the case of hepatitis C virus liver cancer, fatal to the patient. Other chronic viral infections which may be treated in accordance with the present invention include Epstein Barr virus (EBV), as well as other viruses such as those which may be associated with tumors.

Examples of viral infections which can be treated or prevented with the compositions and methods described herein include, but are limited to, viral infections caused by retroviruses (e.g., human T-cell lymphotrophic virus (HTLV) types I and II and human immunodeficiency virus (HIV)), herpes viruses (e.g., herpes simplex virus (HSV) types I and II, Epstein-Ban virus and cytomegalovirus), arenaviruses (e.g., lassa fever virus), paramyxoviruses (e.g., morbillivirus virus, human respiratory syncytial virus, and pneumovirus), adenoviruses, bunyaviruses (e.g., hantavirus), cornaviruses, filoviruses (e.g., Ebola virus), flaviviruses (e.g., hepatitis C virus (HCV), yellow fever virus, and Japanese encephalitis virus), hepadnaviruses (e.g., hepatitis B viruses (HBV)), orthomyoviruses (e.g., Sendai virus and influenza viruses A, B and C), papovaviruses (e.g., papillomaviruses), picornaviruses (e.g., rhinoviruses, enteroviruses and hepatitis A viruses), poxviruses, reoviruses (e.g., rotaviruses), togaviruses (e.g., rubella virus), and rhabdoviruses (e.g., rabies virus). The treatment and/or prevention of a viral infection includes, but is not limited to, alleviating one or more symptoms associated with said infection, the inhibition, reduction or suppression of viral replication, and/or the enhancement of the immune response.

In some embodiments of the invention, a "therapeutically effective amount" is an amount of a composition described herein that results in a reduction in viral titer or microbial titer by at least 2.5%, at least 5%, at least 10%, at least 15%, at least 25%, at least 35%, at least 45%, at least 50%, at least 75%, at least 85%, by at least 90%, at least 95%, or at least 99% in an animal administered a composition of the invention relative to the viral titer or microbial titer in an animal or group of animals (e.g., two, three, five, ten or more animals) not administered a composition of the invention.

Examples of types of cancer and proliferative disorders that can be treated with the compositions described herein include, but are not limited to, leukemia (e.g., myeloblastic, promyelocytic, myelomonocytic, monocytic, erythroleukemia, chronic myelocytic (granulocytic) leukemia, and chronic lymphocytic leukemia), lymphoma (e.g., Hodgkin's disease and non-Hodgkin's disease), fibrosarcoma, myxosarcoma, liposarcoma, chondrosarcoma, osteogenic sarcoma, angiosarcoma, endotheliosarcoma, Ewing's tumor, colon carcinoma, pancreatic cancer, breast cancer, ovarian cancer, prostate cancer, squamous cell carcinoma, basal cell carcinoma, adenocarcinoma, renal cell carcinoma, hepatoma, Wilm's tumor, cervical cancer, uterine cancer, testicular tumor, lung carcinoma, small cell lung carcinoma, bladder carcinoma, epithelial carcinoma, glioma, astrocytoma, oligodendroglioma, melanoma, neuroblastoma, retinoblastoma, dysplasia and hyperplasia. The treatment and/or prevention of cancer includes, but is not limited to, alleviating one or more symptoms associated with cancer, the inhibition or reduction of the progression of cancer, the promotion of the regression of cancer, and/or the promotion of the immune response.

In certain other embodiments, a "therapeutically effective amount" is the amount of a composition of the invention that results in a reduction of the growth or spread of cancer by at least 2.5%, at least 5%, at least 10%, at least 15%, at least 25%, at least 35%, at least 45%, at least 50%, at least 75%, at least 85%, by at least 90%, at least 95%, or at least 99% in a patient or an animal administered a composition described herein relative to the growth or spread of cancer in a patient (or an animal) or a group of patients (or animals) not administered a composition of the invention.

In some embodiments, the compositions are used in a method of treating a yeast or bacterial infection. For example, the compositions and methods described herein can treat infections relating to Streptococcus pyogenes, Streptococcus pneumoniae, Neisseria gonorrhoea, Neisseria meningitidis, Corynebacterium diphtheriae, Clostridium botulinum, Clostridium perfringens, Clostridium tetani, Haemophilus influenzae, Klebsiella pneumoniae, Klebsiella ozaenae, Klebsiella rhinoscleromotis, Staphylococcus aureus, Vibrio cholera, Escherichia coli, Pseudomonas aeruginosa, Campylobacter (Vibrio) fetus, Campylobacter jejuni, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponemapertenue, Treponema carateneum, Borrelia vincentii, Borrelia burgdorferi, Leptospira icterohemorrhagiae, Mycobacterium tuberculosis, Toxoplasma gondii, Pneumocystis carinii, Francisella tularensis, Brucella aborts, Brucella suis, Brucella melitensis, Mycoplasma spp., Rickettsiaprowazeki, Rickettsia tsutsugumushi, Chlamydia spp., Helicobacter pylori or combinations thereof.

The g⁻NK cells can be administered simultaneously with anti-microbial, anti-viral and other therapeutic agents.

For example, the g⁻NK cells can be administered simultaneously with antibodies specific for a selected cancer type. Alternatively, the g⁻NK cells can be administered at selected times that are distinct from the times when antibodies specific for a selected cancer type are administered. Antibodies specific for a selected cancer type include any antibody approved for treatment of cancer. Examples include trastuzumab (Herceptin) for breast cancer, rituximab (Rituxan) for lymphoma, and cetuximab (Erbitux) for head and neck squamous cell carcinoma.

The following non-limiting examples illustrate certain materials and methods used in developing the invention.

EXAMPLE 1

Materials and Methods

This Example describes some of the materials and methods used to develop aspects of the invention.
Human Subjects and Blood Samples.

PBMCs were isolated by Ficoll-Hypaque density gradient centrifugation of samples obtained from discarded, de-identified leukocyte reduction filters (American Red Cross), or blood donations from healthy volunteers with informed consent, approved by the Michigan State University Biomedical and Health Institutional Review Board.
Phenotypic Analysis of NK Cells.

Peripheral blood mononuclear cells (PBMCs) were stained for flow cytometric analysis using fluorochrome-conjugated antibodies as previously described by Kim et al. (*Proc Nall Acad Sci USA* 105(8):3053-3058 (2008)). Antibodies to detect the following proteins were from Beckman Coulter [CD56 (N901), NKG2A (Z199), NKp44 (Z231)], BD Biosciences [CD3ζ (UCHT1), CD16 (3G8), KIR2DL2/3 (CH-L), KIR3DL1 (DX9), NKp46 (9E2), NKp30 (p30-15), CD11a (G43-25B), CD11b (ICRF44), CD11c (B-ly6), NKG2D (1D11), CD161 (DX12), DNAM-1

(DX11), CD57 (NK-1), CD25 (M-A251), IFN-γ (B27), TNF-α (Mab11), CD107a (H4A3), Granzyme A (CB9), Granzyme B (GB11)], Biolegend [CD14 (HCD14), CD19 (HIB19), CD2 (RPA-2.10), 2B4 (C1.7), NTB-A (NT-7), CRACC (162.1), CD69 (FN50)], eBiosciences [KIR2DL1 (HP-MA4), Perforin (dG9)], and R&D [NKG2C (134591)]. For detection of signaling adaptors, cells were fixed and permeabilized, then stained with FcεRIγ subunit antibody (Millipore) that was conjugated with either Alexa-488 or Pacific blue, or mAbs against CD3ζ (6B10.2, Biolegend).

Cytokine Production and Degranulation Assays.

PBMCs were stimulated for 4-6 hours with plate-bound anti-CD16 (3G8), or tumor cells (K562 or 721.221) at a ratio of 10:1 (E:T). Antibody-dependent functional activity was determined by pre-labeling P815 target cells with rabbit anti-mouse lymphocyte polyclonal antibodies, or SCC4 squamous carcinoma cells with anti-EGFR mAb (Cetuximab). All cytokine assays were performed in the presence of Brefeldin A. For degranulation assays, PBMCs were stimulated in the presence of anti-CD107a and monensin for 4 hours, followed by surface and intracellular staining for flow cytometry.

Immunoblot Analysis.

Detection of FcRγ and CD3ζ in cell lysates was by immunoblot analysis using anti-FcεRIγ subunit or anti-CD3ζ primary antibodies followed by anti-rabbit or anti-mouse secondary antibody, respectively, with visualization on Li-cor's odyssey.

NK Cell Sorting and Limiting Dilutions.

PBMCs were sorted following surface receptor staining to exclude non-NK cells and enrich for enriched g⁻NK and conventional NK cells. The resulting samples were plated by limiting dilution in NK cloning medium (RPMI1640 supplemented with 5% pooled human AB serum, 10% fetal bovine serum, 1 μg/ml PHA, 100 U/ml IL-2, and 10 ng/ml Il-15) along with PHA-stimulated (1 μg/ml for 1 h) allogeneic PBMCs and RPMI 8866 cells that had been treated with mitomycin C for 2 hours at 37° C. Feeder cells were added at 25,000 per well every 10-14 days for up to 2 months.

mRNA Quantification.

Total RNA extracts were used to prepare cDNA for amplification by gene-specific primers in SYBR green PCR Mastermix (for enriched NK cells), or in the presence of gene-specific Taqman probes (for cultured NK cells) (Applied Biosystems). Amplification and detection was performed using an Applied Biosystems StepOnePlus Instrument and software. Relative quantities were calculated after normalization to GAPDH. The following primers were for SYBR green assays:

```
FcRγ sense,
                                           (SEQ ID NO: 5)
5'-CGGCCGATCTCCAGCCCAAGA-3'

FcRγ anti-sense,
                                           (SEQ ID NO: 6)
5'-GCATGCAGGCATATGTGATGCC-3';

GAPDH sense,
                                           (SEQ ID NO: 7)
5'-GGAAGGTGAAGGTCGG-3';
and GAPDH anti-sense,
                                           (SEQ ID NO: 8)
5'-GAAGATGGTGATGGGATTTC-3'.
```

Taqman gene expression assays for FcRγ (Hs00175408_m1), CD3ζ(Hs00609515_m1), and GAPDH (Hs03929097_g1) were from Applied Biosciences.

Statistics.

Statistical analyses were performed using the paired Student's t-test. Differences were considered statistically significant when $P<0.05$.

EXAMPLE 2

NK Cells Deficient for FcRγ Have Enhanced CD16-Dependent Responsiveness

This Example illustrates that there is a subset of natural killer cells in some humans, which are referred to herein as g⁻NK cells. Such g⁻NK cells have useful properties, including the ability to secrete higher levels of cytokines and chemokines than other natural killer cells.

Identification of FcRγ-deficient NK Cells.

Figure 1B:
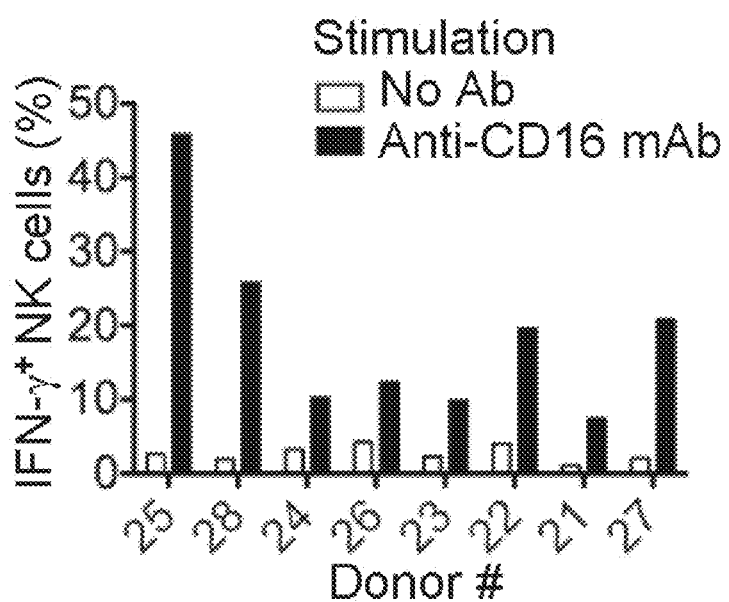

PBMCs from a large panel of donor samples obtained from leukocyte reduction filters were analyzed for IFN-γ production by NK cells following incubation with tumor cells or antibody-coated target cells. This analysis revealed that NK cells from many donors did not show a correlative response pattern; for instance, NK cells from donors #25 and #28 responded poorly to K562 tumor cells, but responded markedly well to antibody-coated P815 target cells (FIG. 1A). Donor NK cells that had responded well to antibody-coated target cells also responded robustly to immobilized anti-CD16 mAb (FIG. 1B), confirming the direct involvement of CD16. Thus, within certain donors, the responsiveness of NK cells to stimulation through CD16 vs. tumor recognition receptors was observed to be dramatically different.

Figure 1C:
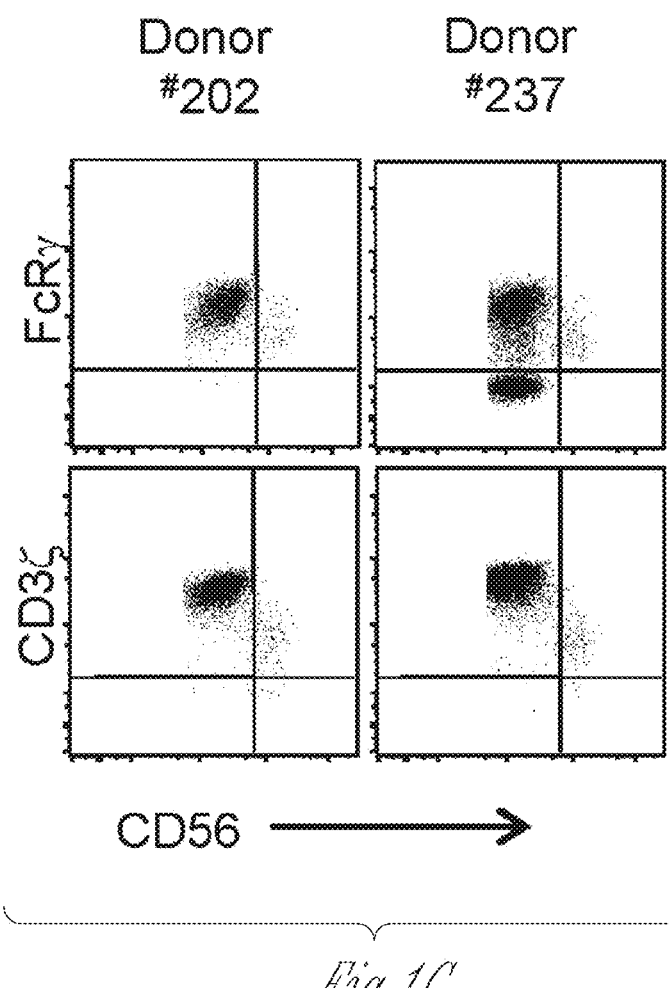
Figure 1D:
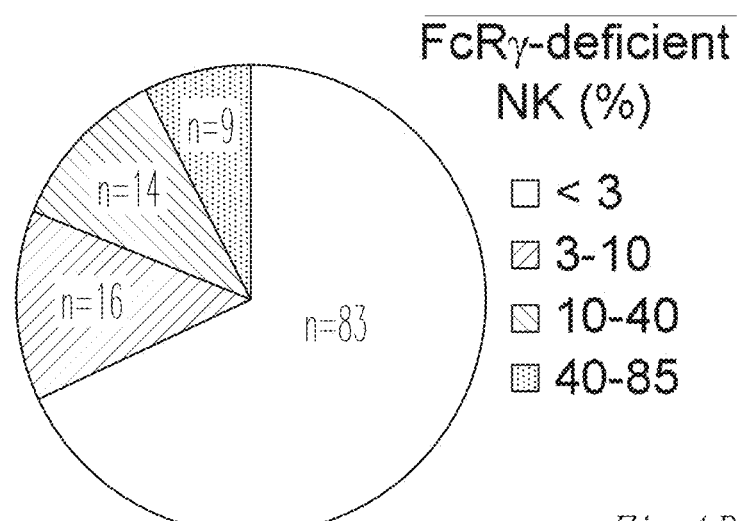
Figure 1E:
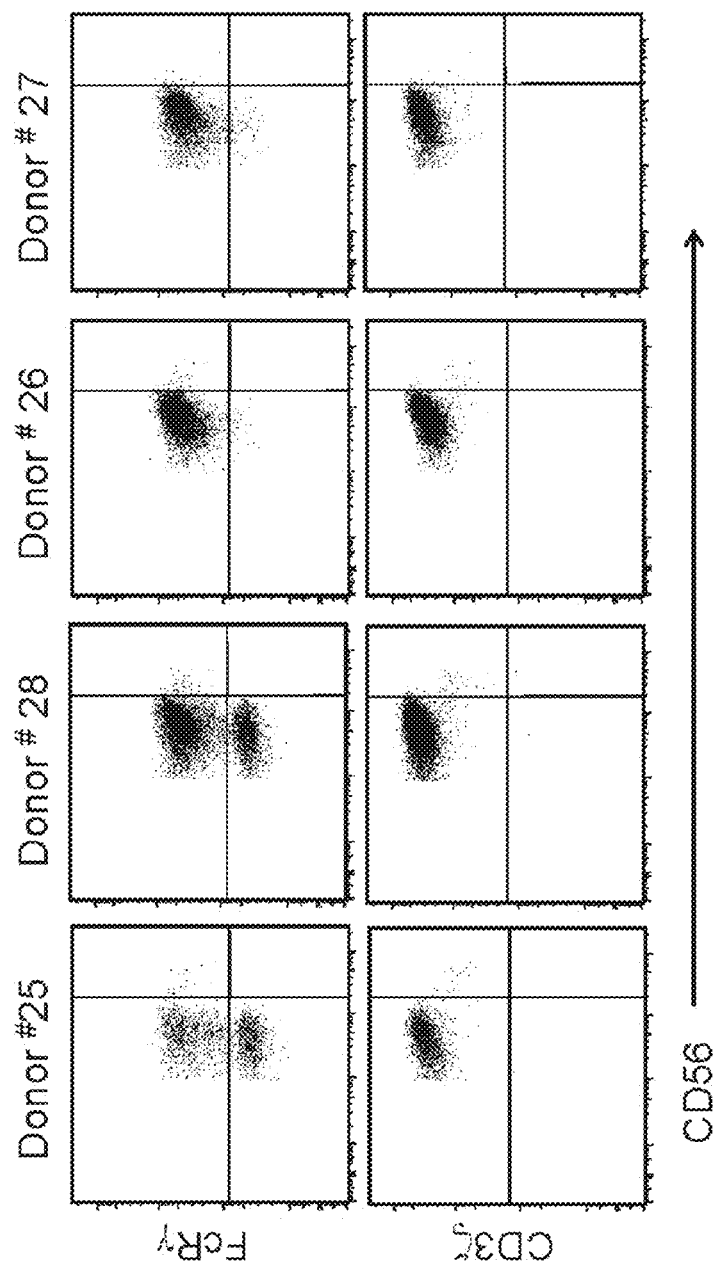

To explore potential mechanisms underlying the differential responsiveness, the expression of FcRγ and CD3ζ was examined. Both FcRγ and CD3ζ are associated with CD16 as well as the natural cytotoxicity receptors (NCRs) NKp46 and NKp30. Such NCRs are involved in recognition of K562 (Sivori et al. *Eur J Immunol* 29(5):1656-1666 (1999); Brandt et al., *J Exp Med* 206(7):1495-1503 (2009)). Flow cytometric analysis following intracellular staining showed that in the majority of the donors, essentially all NK cells expressed both FcRγ and CD3ζ (FIG. 1C, donor #202), consistent with current understanding expressed by most workers in the field (see, e.g., Lanier, *Nat Immunol* 9(5): 495-502 (2008)). However, some donors (e.g., donor #237), including those donors with high CD16 responsiveness and poor tumor reactivity such as donors #25 and #28, had a distinct subset of NK cells that was deficient for FcRγ, while all NK cells expressed high levels of CD3ζ (FIG. 1C and FIG. 1E). The FcRγ-deficient NK cells were restricted to the $CD56^{dim}$ population in all donors examined, and the $CD56^{bright}$ population expressed intermediate levels of both adaptor chains. The presence of FcRγ-deficient NK cells was initially observed during analyses of PBMCs isolated from de-identified leukocyte reduction filters, where 21 out of 80 samples contained readily detectable numbers of FcRγ-deficient NK cells, i.e., more than 3% of the $CD56^{dim}$ NK cells. To confirm that these FcRγ-deficient cells are present in freshly isolated samples, PBMCs were also analyzed from 42 recruited donors without any apparent illness. Among these healthy individuals, 18 had FcRγ-deficient NK cells that comprised more than 3% of their $CD56^{dim}$ NK cell pool. Together, appreciable numbers (at frequencies ranging from 3% to as much as 85% of the $CD56^{dim}$ NK cell pool) of FcRγ-deficient NK cells were present in about one-third (39 out of 122 donors) of the healthy individuals tested (FIG. 1D).

Figure 2A:
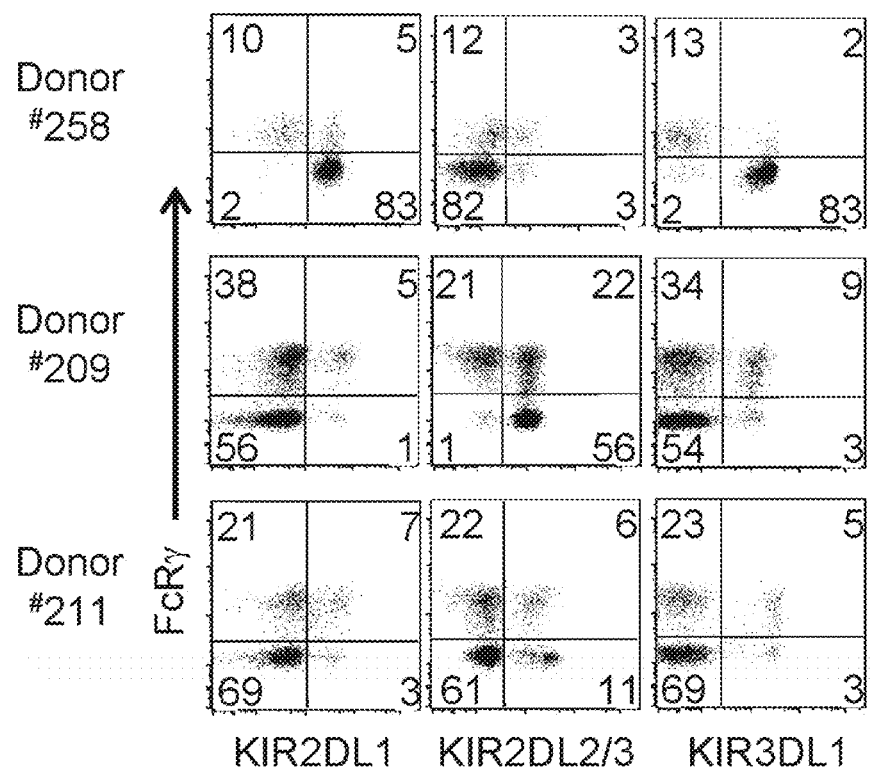
Figure 2B:
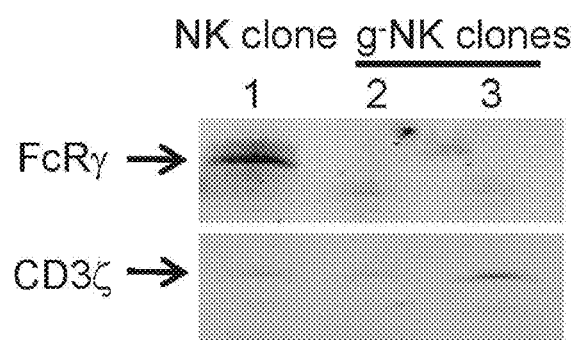
Figure 2C:
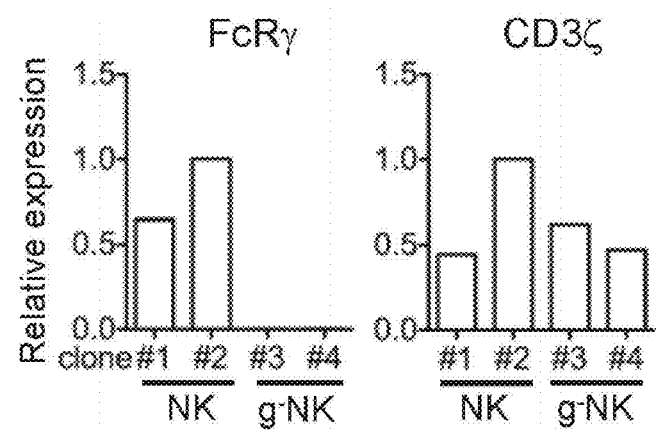
Figure 2D:
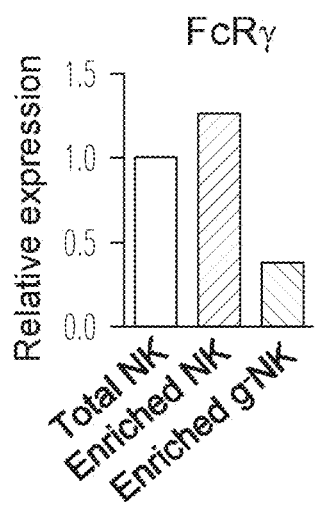
Figure 2E:
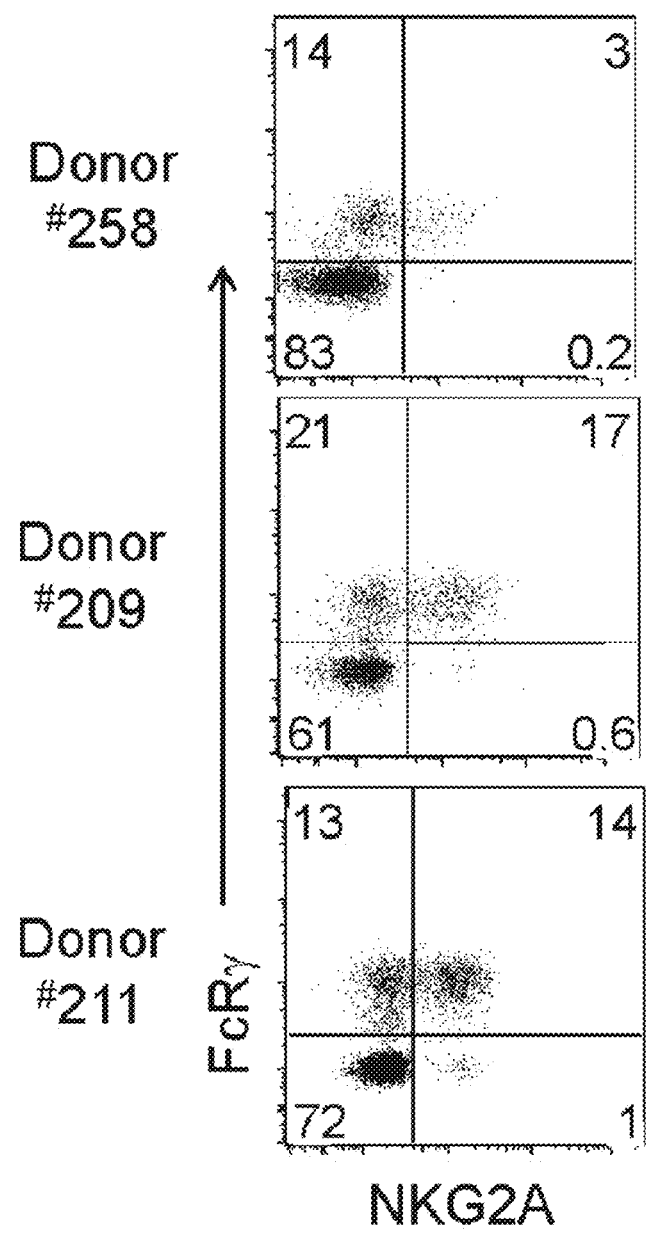
Figure 2A:
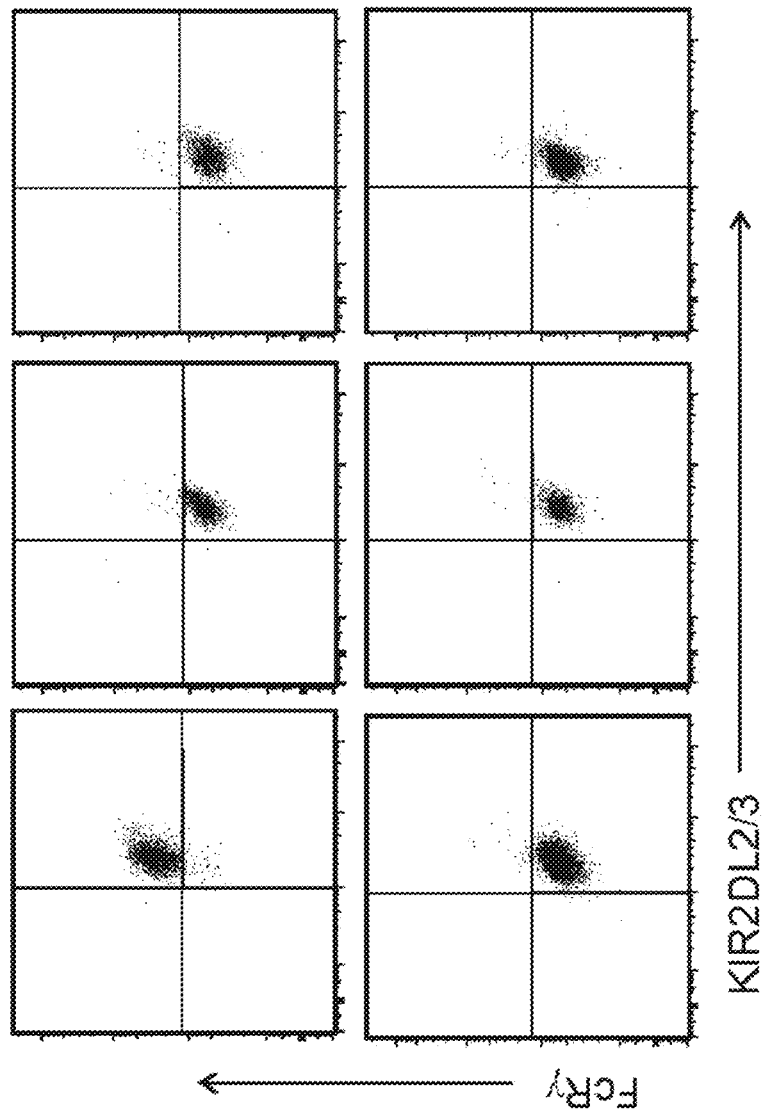

To examine the potential homogeneity of FcRγ-deficient NK cells and the subset similarities between different donors, the expression of killer cell immunoglobulin-like receptors (KIRs) and NKG2A was surveyed. Such KIRs and NKG2A are inhibitory receptors for MHC I and are expressed by partially overlapping subsets of NK cells (Parham, *Nat Rev Immunol* 5(3):201-214 (2005)). The FcRγ-deficient NK cells in some donors had highly skewed expression of KIR2DL1, KIR2DL2/3 and/or KIR3DL1, three well-characterized KIRs expressed primarily within the $CD56^{dim}$ NK cell population (id.). For instance, in donor #258, almost all (>95%) of the FcRγ-deficient NK cells expressed KIR2DL1 as well as KIR3DL1 but not KIR2DL2/3, whereas only small percentages of $CD56^{dim}$ NK cells expressing FcRγ (hereafter referred to as conventional NK cells) displayed these receptors (FIG. 2A). In other donors (e.g., donor #209), FcRγ-deficient NK cells predominantly expressed KIR2DL2/3, but not KIR2DL1 and KIR3DL1. Alternatively, in approximately half of the donors with FcRγ-deficient NK cells (e.g., donor #211), such predominant KIR expression was not observed, similar to conventional NK cells (FIG. 2A). Interestingly, the expression of NKG2A was under-represented on FcRγ-deficient NK cells in all donors (FIG. 2E). Together, while FcRγ-deficient NK cells are heterogeneous in some donors, they show near homogeneous expression of particular KIRs in others, indicating that FcRγ-deficient NK cells may be derived from expansion of particular NK subsets in certain donors.

To determine whether FcRγ-deficient NK cells express a low level of FcRγ, samples of FcRγ-deficient NK cells were obtained and enriched to about 70% purity by cell sorting based on expression of KIRs that correlated well with FcRγ-deficiency (e.g., KIR2DL2/3 in donor #209). To further increase the purity, the sorted cells (KIR2DL2/3$^+$ NK cells) were cultured under limiting dilution conditions. Analysis of the resulting cultures showed that many different FcRγ-deficient NK cell clones were homogeneous (>97%) for FcRγ-deficiency (FIG. 2F). Conventional NK cells (KIR2DL2/3$^-$) were also sorted and cultured in parallel. Immunoblot analysis showed that the FcRγ-deficient NK cell clones did not express any detectable levels of FcRγ, unlike conventional NK cell clones (FIG. 2B). In contrast, FcRγ-deficient NK cell clones expressed CD3ζ at levels comparable to those expressed by conventional NK cell clones. These data indicate that FcRγ-deficient NK cells (also referred to as $^\gamma$-NK or g$^-$NK cells) lack detectable FcRγ protein. Furthermore, the amount of mRNA for FcRγ, but not CD3ζ, was dramatically reduced in enriched g$^-$NK cell preparations from freshly isolated PBMCs (FIG. 2C). The reduction in FcRγ mRNA was also confirmed using $^\gamma$-NK cell clones (FIG. 2D). Thus, it is likely that the deficiency of FcRγ expression in g$^-$NK cells results from impaired transcription, rather than post-translational events. Together, these results reveal that substantial numbers of this novel subset of human NK cells, characterized by a deficiency in FcRγ mRNA and protein expression, are present in a significant proportion of the human population.

Distinct Phenotype of g$^-$NK Cells.

Figure 3A:
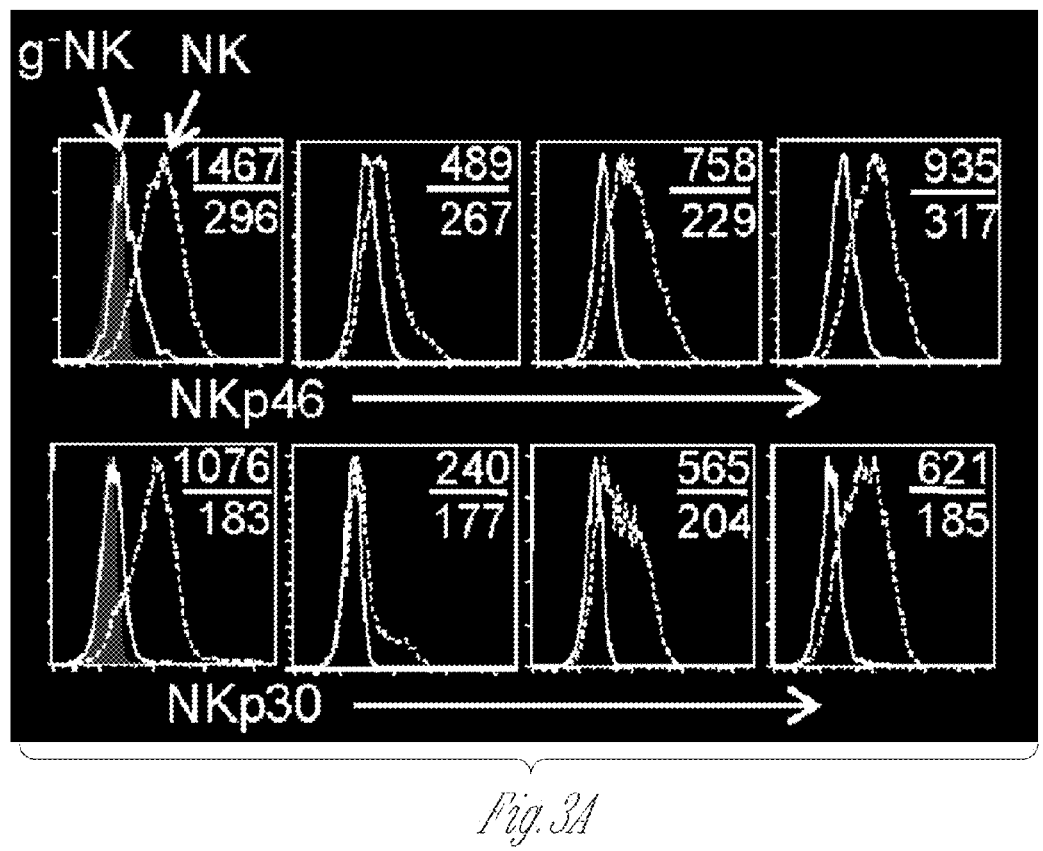
FIGS. 3A-G illustrate that FcRγ-deficient NK (g⁻NK) cells display a distinct expression profile of several cell surface receptors.

To determine whether deficiency of FcRγ may impact the expression of activation receptors with which it associates, the expression of NKp46 in g$^-$NK cells and conventional NK cells was compared. FIG. 3A shows that the expression of NKp46 was dramatically reduced in g$^-$NK cells compared to conventional NK cells in all donors examined (MFI: 914±110 for conventional NK vs. 250±21 for g$^-$NK cells; n=11). Furthermore, g$^-$NK cells displayed much lower expression of NKp30 in all donors (MFI: 631±89 vs. 186±4, n=11) (FIG. 3A). In a few donors, conventional NK cells expressed FcRγ but also displayed relatively low levels of NCRs (FIG. 3A). These data indicate that FcRγ is required for the expression of both NKp46 and NKp30.

Figure 3B:
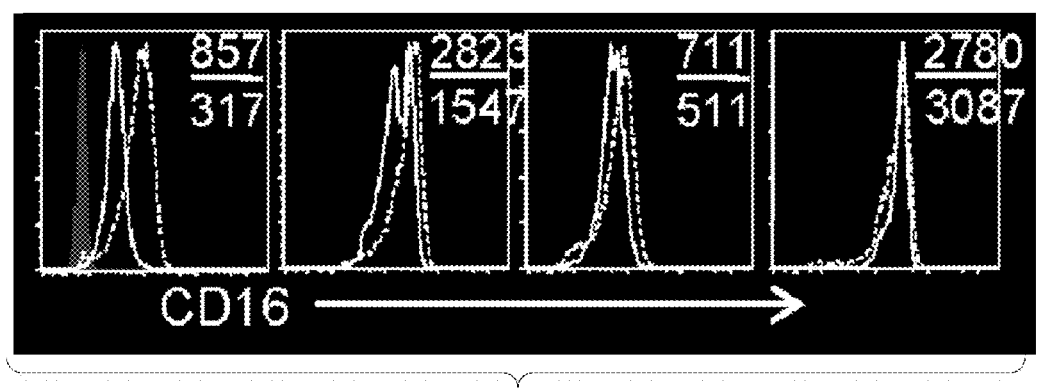

CD16 expression also reduced in g$^-$NK cells, but not so dramatically as FcRγ expression. In particular, the expression level of CD16 on g$^-$NK cells was approximately 60% of that on conventional NK cells (MFI: 1362±263 vs. 844±227, n=13), and there was variation between donors (FIG. 3B). These data suggest that FcRγ contributes to, but is not essential for CD16 expression.

KIR2DL4 is an activation KIR associated with FcRγ (Kikuchi-Maki et al., *J Immunol* 174(7):3859-3863 (2005)). While conventional NK cells showed detectable levels of KIR2DL4, after culture in IL-2, g$^-$NK cells did not show such upregulation (FIG. 3F), indicating the requirement of FcRγ for KIR2DL4 expression. Together, these data suggest that FcRγ-deficiency profoundly affects the cell surface expression of NKp46, NKp30 and KIR2DL4, but it has only a limited effect on CD16 expression.

Figure 3C:
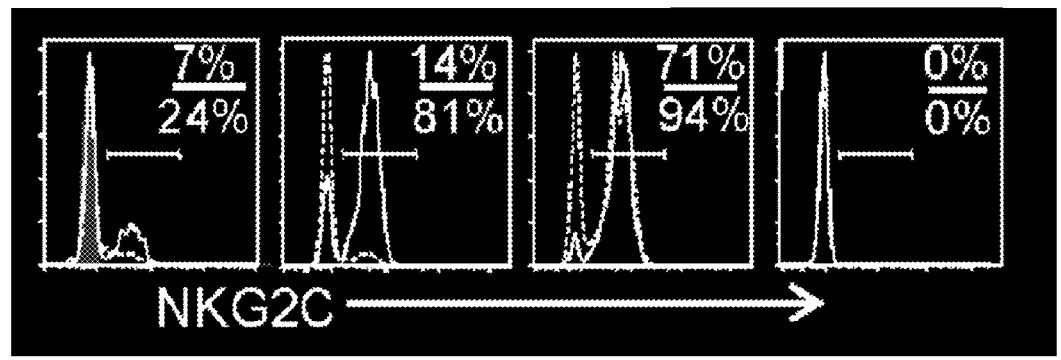
Figure 3D:
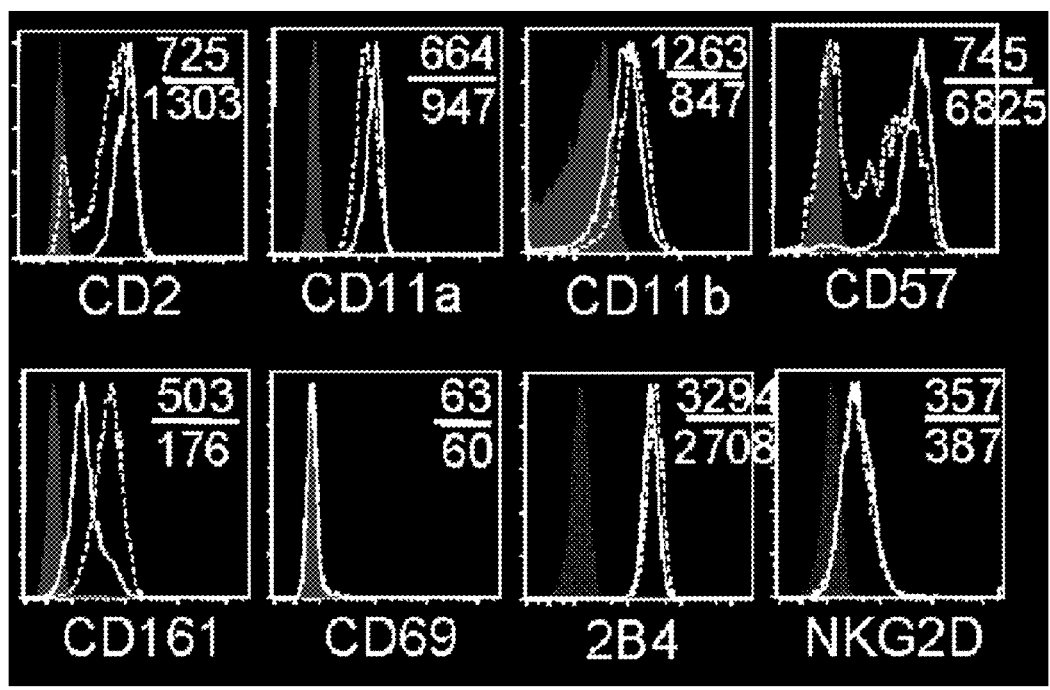
Figure 3E:
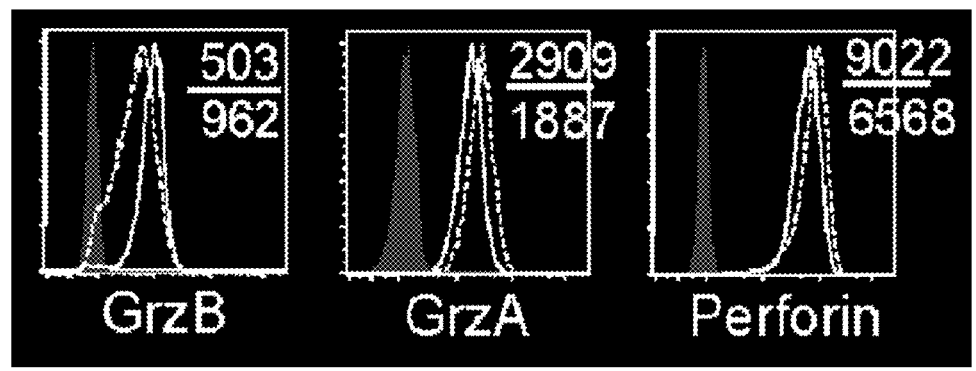
Figure 3F:
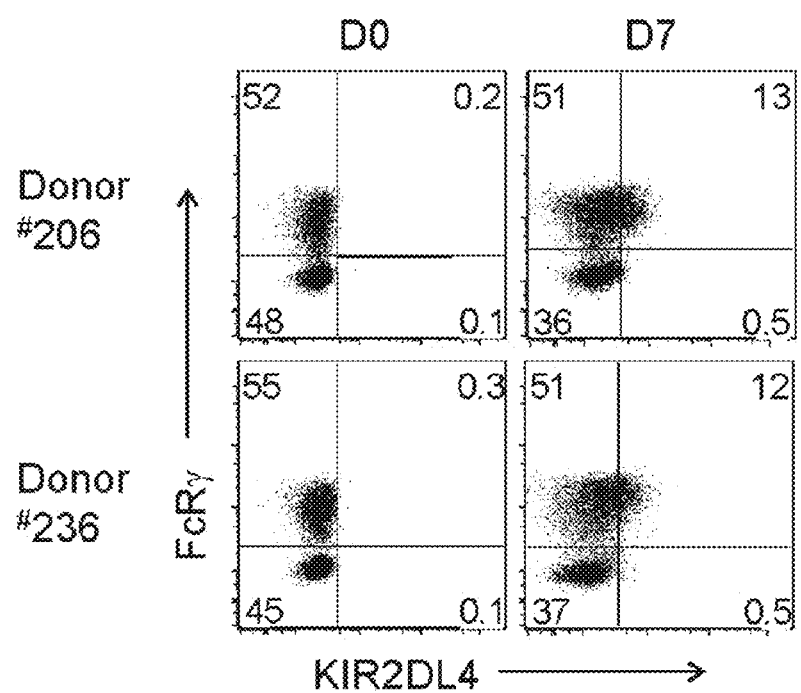
Figure 3G:
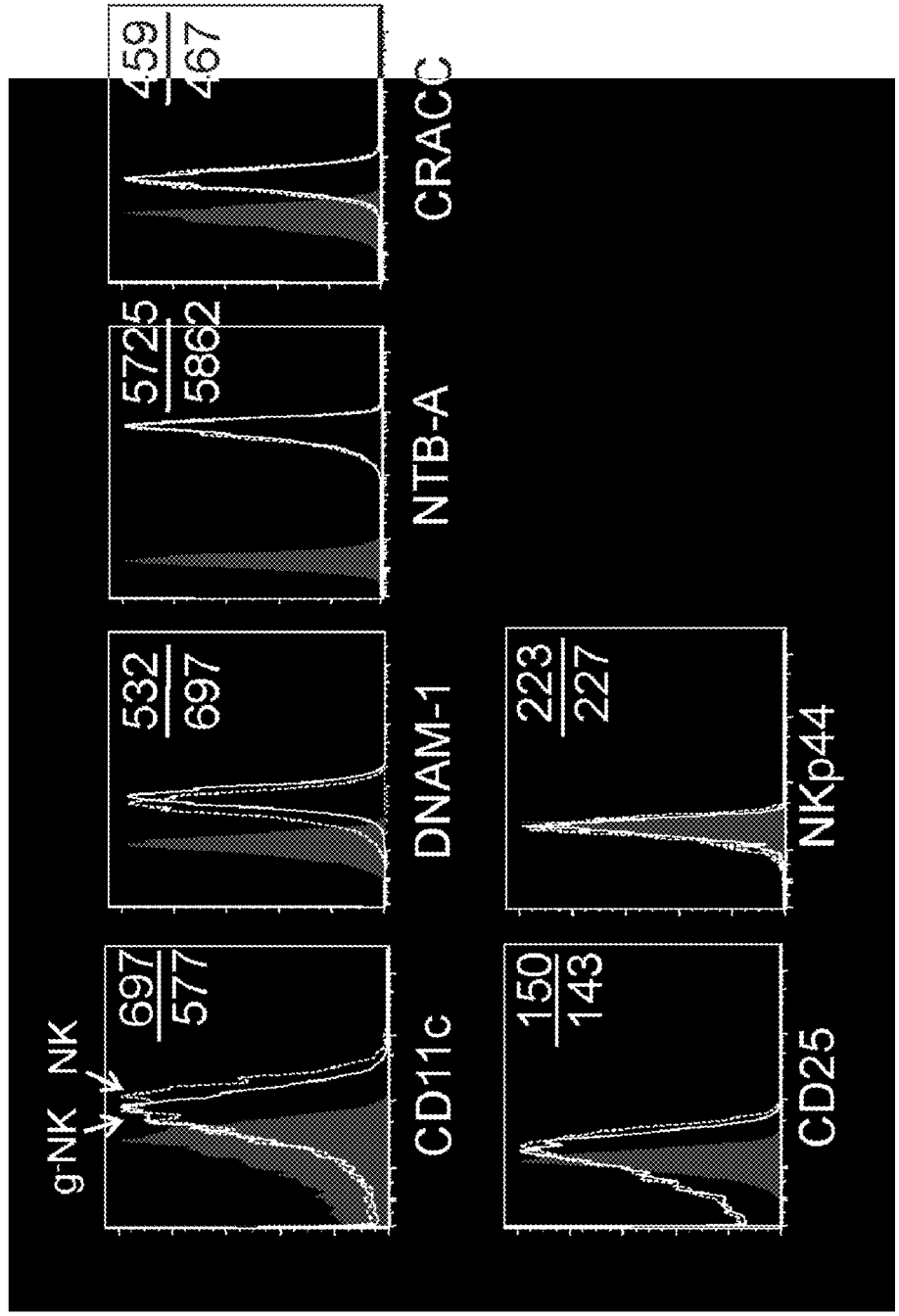

In addition to the FcRγ-associated receptors, g$^-$NK and conventional NK cells differ in expression levels of NKG2C, an activation receptor expressed by a subset of NK cells (Bryceson & Long, *Curr Opin Immunol* 20(3):344-352 (2008); Vivier et al. *Science* 331(6013):44-49 (2011)). Compared to conventional NK cells, g$^-$NK cells expressed this receptor more frequently in most of the donors, although g$^-$NK cells in a few donors expressed NKG2C at low-to-undetectable levels similar to conventional NK cells (FIG. 3C). Additionally, g$^-$NK cells expressed the adhesion receptors CD2 and CD11a at higher levels than conventional NK cells, whereas expression of CD11b and CD11c was slightly lower on g$^-$NK cells (FIGS. 3D and 3G). Further, g$^-$NK cells expressed higher levels of CD57, a marker present on mature NK cells (Lopez-Verges S, et al., *Blood* 116(19): 3865-3874 (2010); Bjorkstrom et al., *Blood* 116(19):3853-3864 (2010)). On the other hand, the expression of the inhibitory receptor CD161 was lower on g$^-$NK cells. The g$^-$NK cells did not express activation markers (CD69, CD25 and NKp44), similar to conventional NK cells (FIG. 3D and FIG. 3G). There were also no consistent differences between g$^-$NK and conventional NK cells for other activation receptors (2B4, NKG2D, DNAM-1, NTB-A and CRACC) (FIG. 3D and FIG. 3G). Finally, analysis of cytolytic effector molecules showed that granzyme B expression is slightly higher, while perforin and granzyme A expression are slightly lower in g$^-$NK cells compared to conventional NK cells (FIG. 3E). Thus, g$^-$NK and conventional NK cells differ in the expression of FcRγ-associated receptors, as well as that of several non-associated receptors and cytolytic effector molecules.

Functional Responsiveness of g$^-$NIK Cells.

Figure 4A:
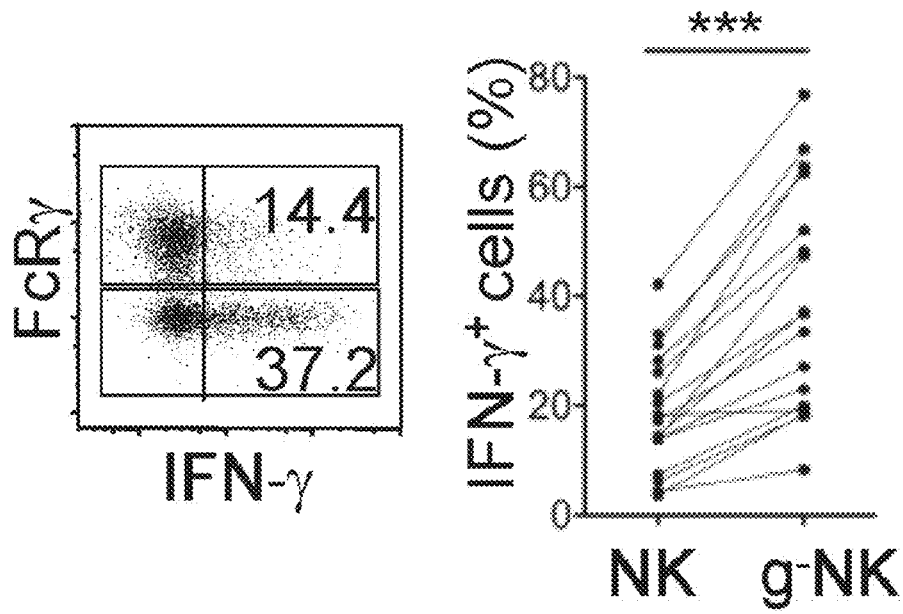
FIGS. 4A-I show that g⁻NK cells display enhanced ability to respond to stimulation through CD16 but poor anti-tumor activity.
Figure 4B:
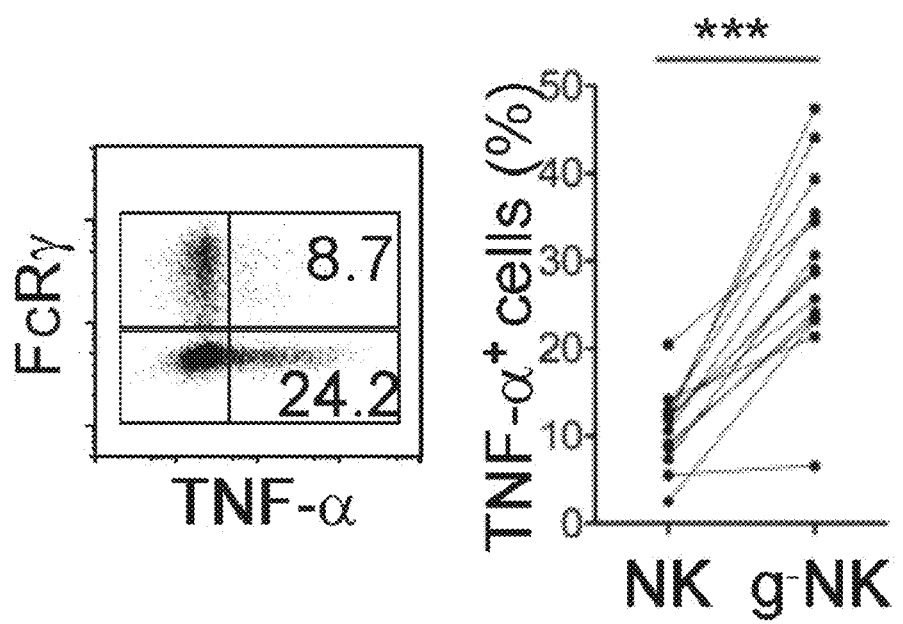
Figure 4C:
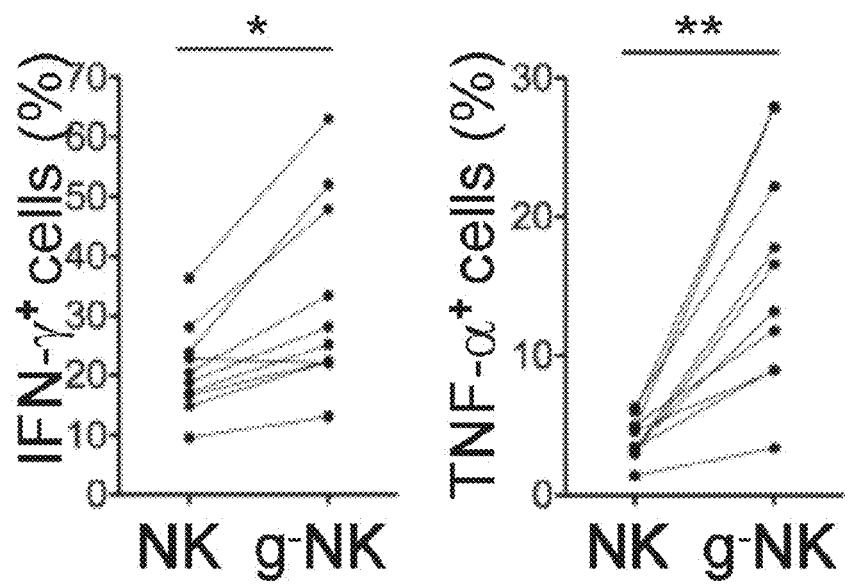
Figure 4D:
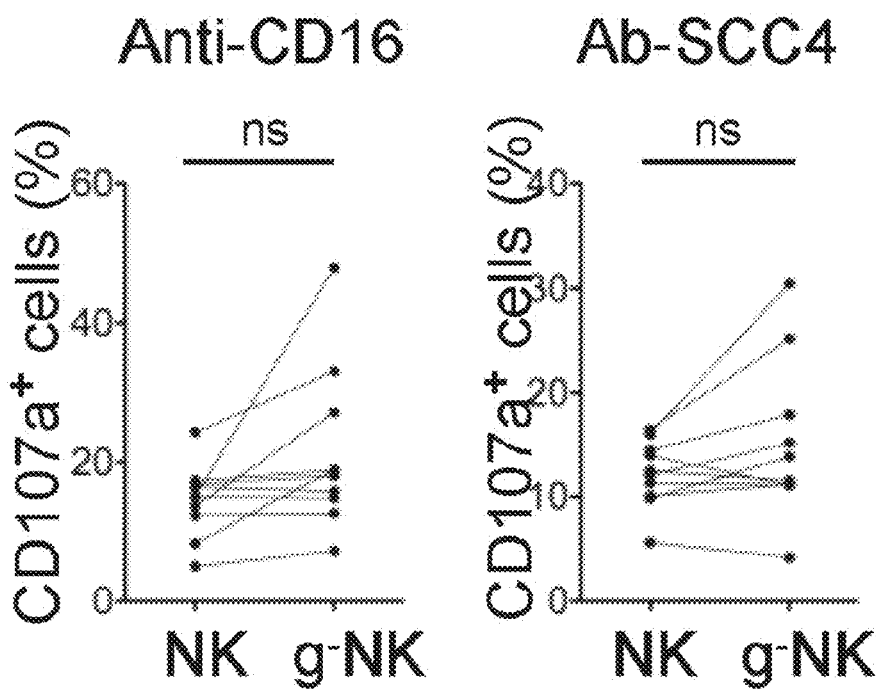
Figure 4E:
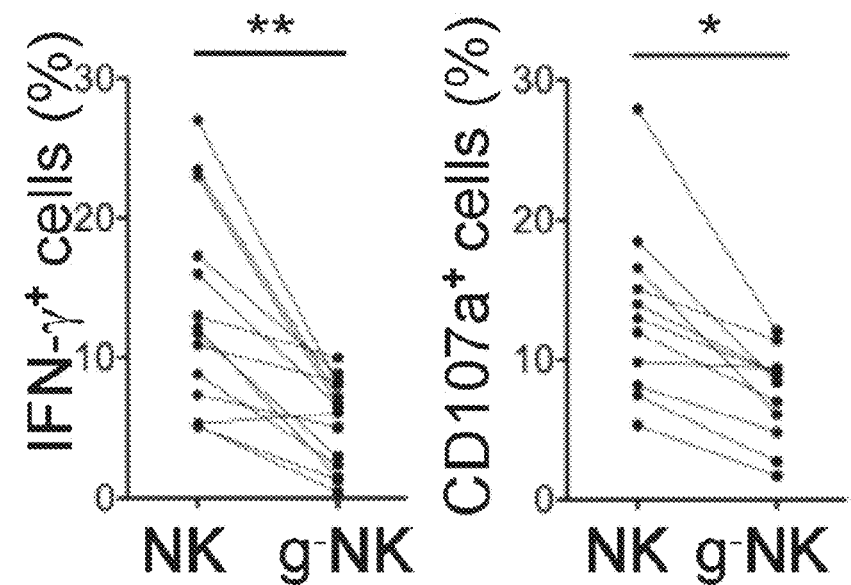
Figure 4F:
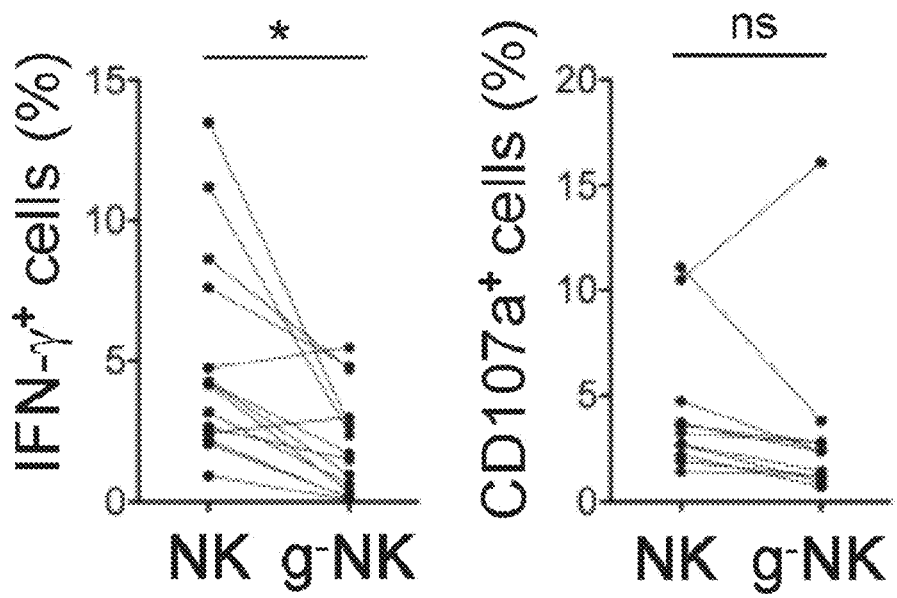
Figure 4G:
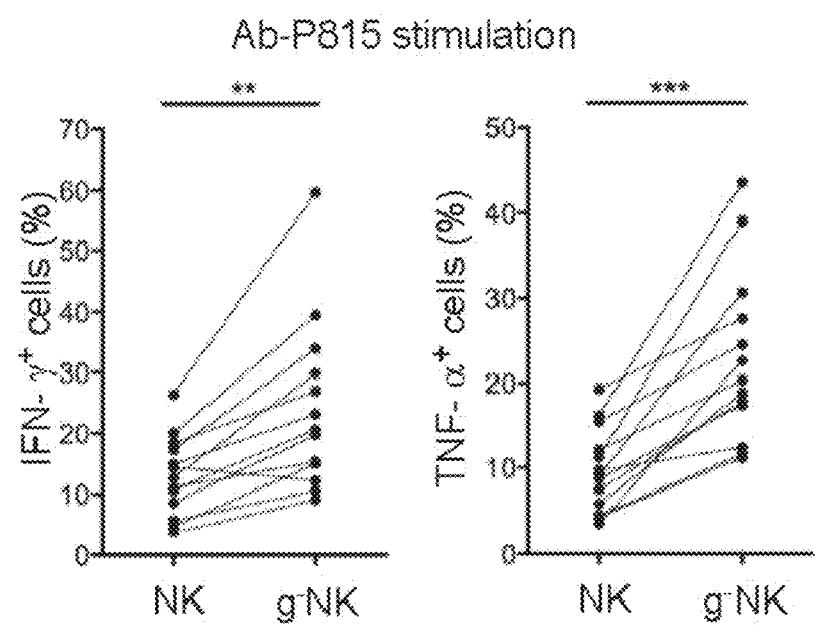
Figure 4H:
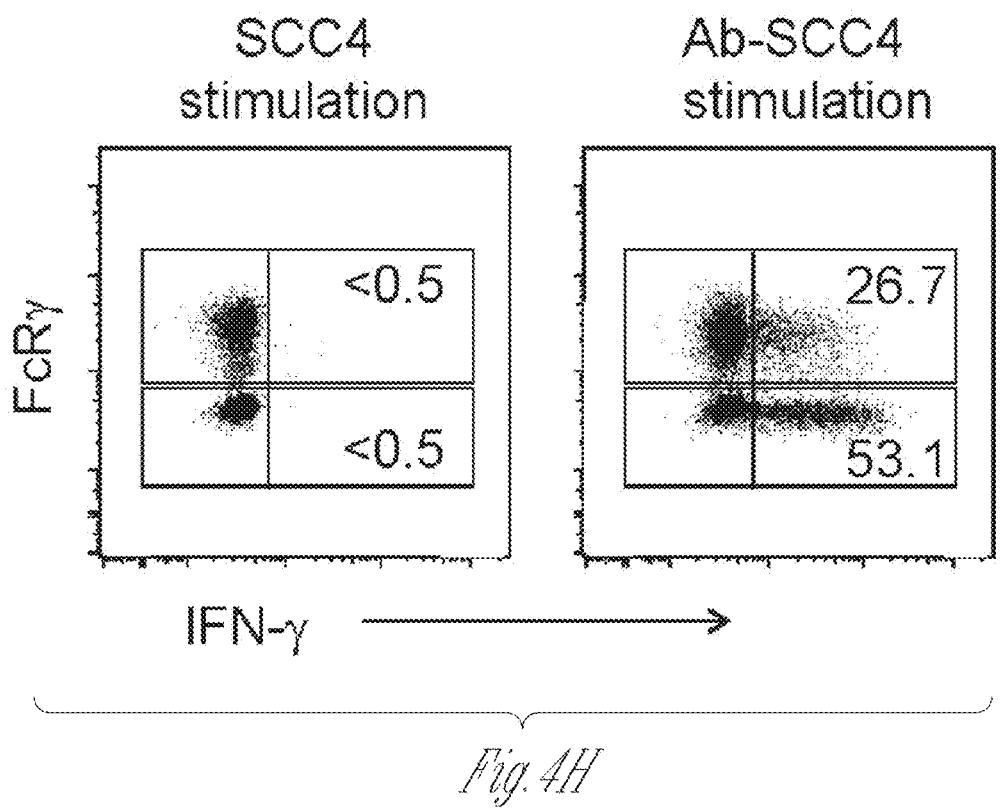
Figure 4I:
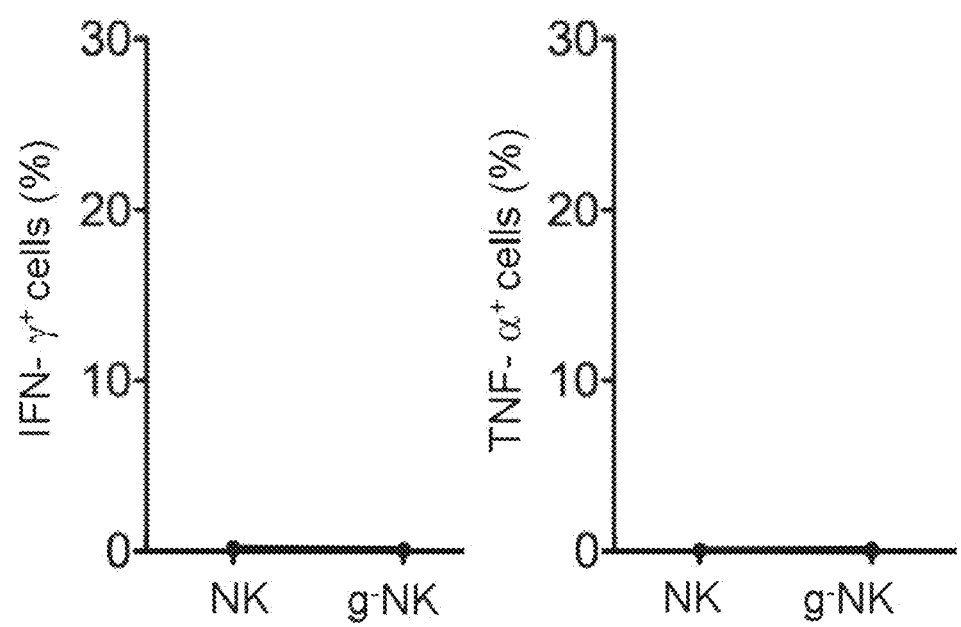

To evaluate the responsiveness of g$^-$NK cells to CD16 stimulation, NK cell cytokine production was examined following incubation with immobilized anti-CD16 mAb. Unexpectedly, g$^-$NK cells produced much greater amounts of IFN-γ compared to conventional NK cells (P<0.0001) (FIG. 4A), providing an explanation for the initial observations in donors #25 and #28 (FIGS. 1A and B). In addition to IFN-γ production, CD16 cross-linking resulted in significantly more TNF-α production by g$^-$NK cells (P<0.0001) (FIG. 4B). When stimulated by antibody-coated P815 cells, $^\gamma$-NK cells also produced these cytokines more abundantly (FIG. 4G). To test CD16 responsiveness in the context of human IgG Fc, PBMCs were stimulated with EGFR+human squamous cell carcinoma (SCC4) coated with humanized anti-EGFR mAb. Under these conditions, g−NK cells again produced higher amounts of both IFN-γ and TNF-α than conventional NK cells (FIG. 4C). In the absence of antibody, neither g−NK nor conventional NK cells yielded any detectable cytokine production (FIGS. 4H and 4I), indicating that this response was mediated through CD16 engagement. Together, these data indicate that g−NK cells respond more robustly to CD16 stimulation compared to conventional NK cells. The NK cell degranulation response was evaluated by measuring cell surface expression of CD107a as a surrogate marker following CD16 crosslinking, or exposure to antibody-coated SCC4 cells. Although CD107a expression trended higher in g−NK cells than in conventional NK cells, the difference was not statistically significant (FIG. 4D). The less dramatic difference in CD107a expression may be explained by a lower activation threshold, or lower transcriptional requirements for degranulation as compared to cytokine production (Fauriat et al., *Blood* 115(11):2167-2176 (2010)). Nonetheless, g−NK cells display a markedly enhanced ability to respond to stimulation through CD16, particularly for cytokine production.

To evaluate the functional activity of g−NK cells against tumor cells, NK cell cytokine production was examined following stimulation with K562 cells. Compared to conventional NK cells, g−NK cells expressed significantly less IFN-γ ($P<0.001$) (FIG. 4E). Additionally, g−NK cells had poorer degranulation responses than conventional NK cells ($P<0.01$) (FIG. 4E). Similar results were obtained with another tumor target, 721.221, although the degranulation response did not reach statistical significance (FIG. 4F). However, variation was observed between donors in response to these tumor targets, especially for 721.221, presumably reflecting complex NK-target cell interactions as well as genetic heterogeneity among donors. These data indicate that direct responsiveness of g−NK cells to tumor cells is generally poor, consistent with the impaired expression of both NKp46 and NKp30, and their importance for anti-tumor activity.

Long-term Stability of the γ−NK Population.

Figure 5A:
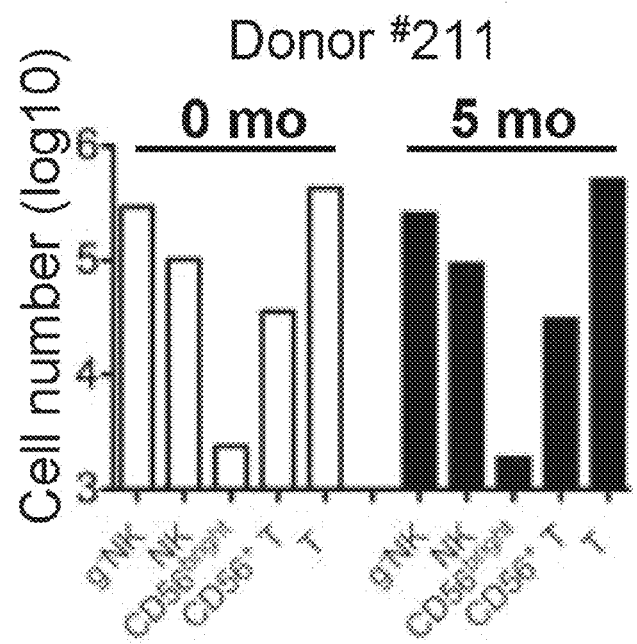
Figure 5B:
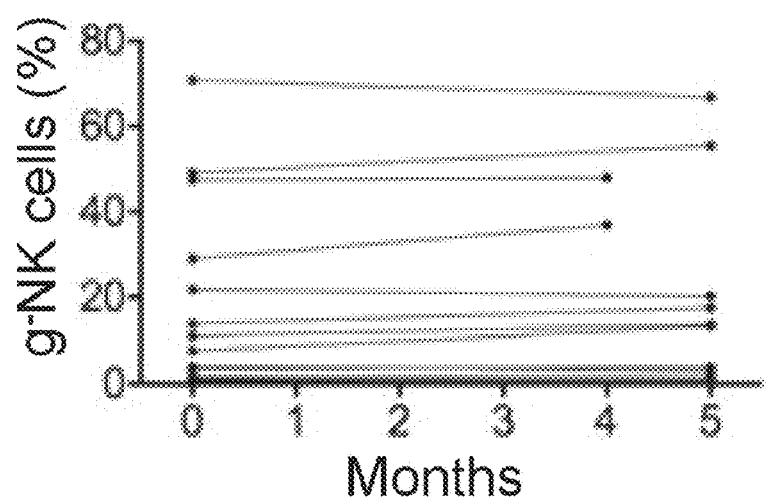
Figure 5C:
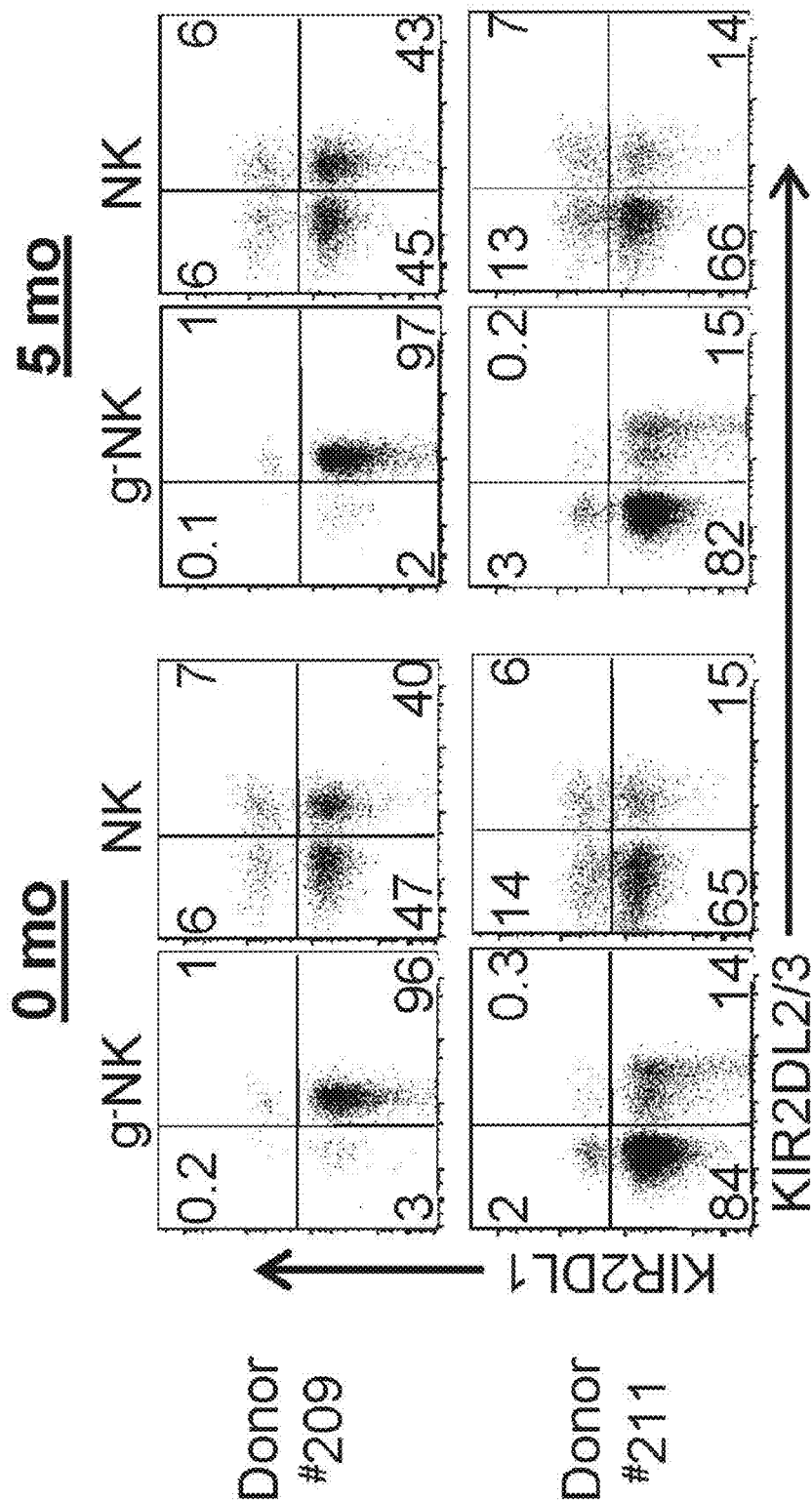
Figure 5E:
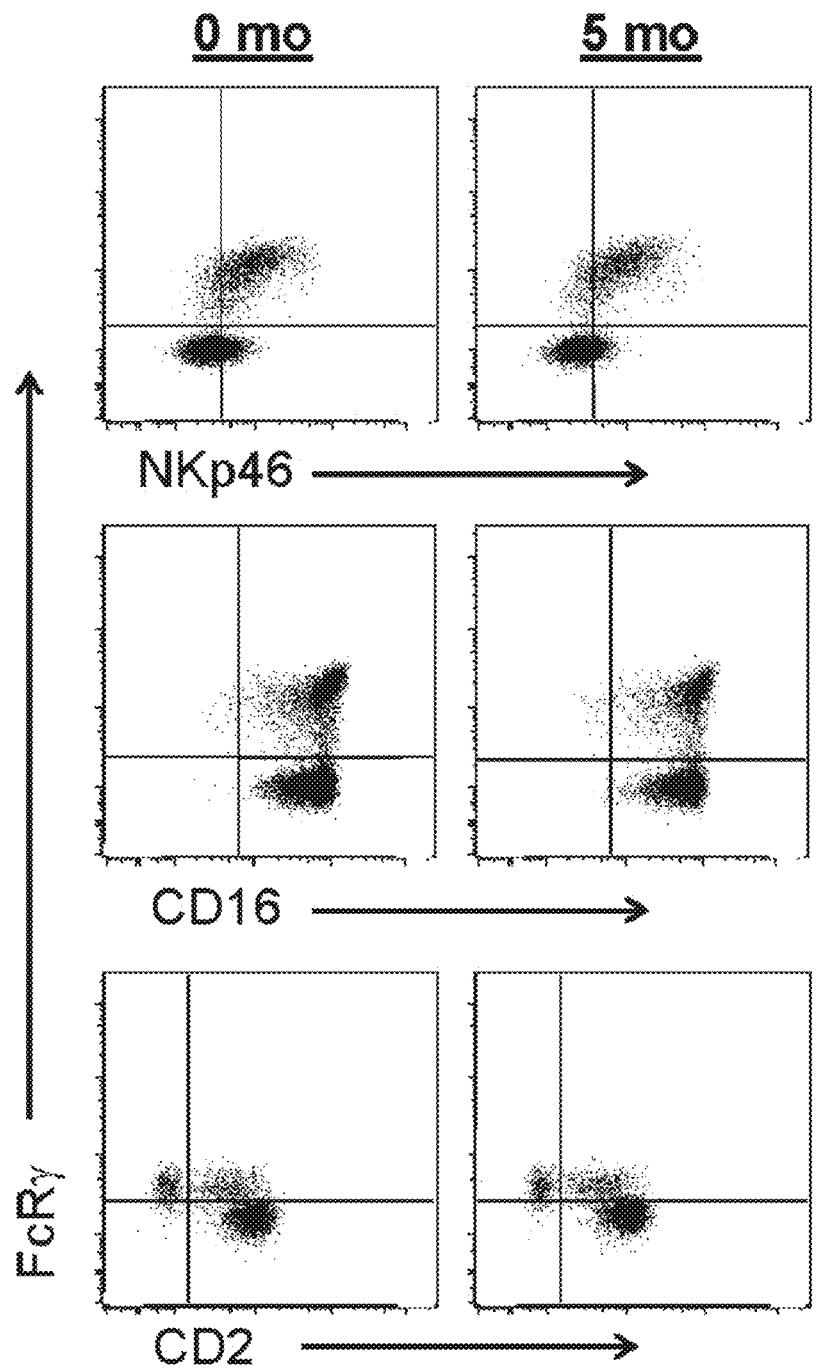

To investigate whether the g−NK subset is a transient or stable population, a longitudinal study was performed to evaluate the number and phenotype of g−NK cells over an extended period of time. Four to five months after the initial blood donation, additional samples were analyzed from several donors (n=10) that originally had readily detectable numbers (i.e., more than 3% of $CD56^{dim}$ NK cells) g−NK cells. For every donor examined, the number of g−NK cells was nearly identical during this time frame (FIG. 5A and FIG. 5D). The relative frequency of g−NK cells within the $CD56^{dim}$ NK cell pool was also stably maintained (FIG. 5B). To determine if the subset composition had altered, KIR expression profiles were examined. This analysis indicated that the subset composition with respect to KIR expression is also essentially stable. For instance, for donor #209, in which >95% of the g−NK cells were KIR2DL1−KIR2DL2/3+, a nearly identical pattern of KIR expression was observed 5 months later (FIG. 5C upper panels). In addition, the g−NK cells from donor #211 displayed such a similar expression pattern over 5 months where the g−NK cells did not frequently express KIR2DL1, KIR2DL2/3, or KIR3DL1 (FIG. 5C lower panels). Moreover, analysis of several activation receptors, including NKp46, CD16 and CD2, did not show any noticeable change (FIG. 5E). Similar longitudinal studies were performed on donors (n=7) that initially had no detectable γ−NK cells (i.e., less than 3% of $CD56^{dim}$ NK cells) and found that there was no appearance of g−NK cells (FIG. 5B). Taken together, these results suggest that in healthy individuals with g−NK cells, this population exists at nearly constant levels for at least 4-5 months and the subset composition and phenotype of g−NK cells are stable.

EXAMPLE 3

Antibody-Dependent Memory-like NK Cells Distinguished by FcRγDeficiency

Introduction

Natural killer cells are innate immune cells that contribute to host defense against viral infection and malignancy through rapid production of cytokines and the release of cytotoxic granules (Hwang et al. 2012. Int. Immunol. 24:792-802). In particular, NK cells play a crucial role in the control of herpes virus infection, such as infection by human CMV (HCMV) (Biron et al. 1989. N. Engl. J. Med. 320: 1731-1735; Etzioni et al. 2005. J. Pediatr. 146:423-425; Kuijpers et al. 2008. Blood. 112: 914-915). Despite being categorized as innate immune cells with a relatively short lifespan (estimated at 10-20 d) (Ranson et al. 2003. Blood. 101:4887-4893; Jamieson et al. 2004. J. Immunol. 172:864-870), recent studies of mouse models demonstrate adaptive immune features of NK cells, such as recall responses to certain haptens and viral Ags lasting up to several months (O'Leary et al. 2006. Nat. Immunol. 7:507-516; Sun et al. 2009. Nature. 457:557-561; Paust et al. 2010. Nat. Immunol. 11:1127-1135). However, considering the fact that NK cells lack mechanisms for gene rearrangement to generate Ag-specific receptors, the molecular basis for specific target recognition is poorly understood, and it is unclear whether NK cells can mount memory responses to diverse pathogens (Hwang et al. 2012. Int. Immunol. 24:792-802; Cooper et al. 2010. Immunol. Rev. 235:297-305). Recently, it was found that about one third of healthy individuals have circulating FcRg-deficient NK (g−NK) cells that express CD3ζ normally, but are deficient for FcRγ (Hwang et al. 2012. Int. Immunol. 24:792-802), the two signaling adaptors associated with the FcR CD16 (Lanier. 2008. Nat. Immunol. 9:495-502). Provided herein is data which supports that g−NK cells represent a distinct type of memory cell that primarily uses pathogen-specific Abs instead of Ag-specific receptors for target recognition.

Materials and Methods

Human Subjects and Blood Samples

PBMCs from healthy donors were obtained with informed consent or from discarded, deidentified leukoreduction filters (American Red Cross), as approved by the Michigan State University Biomedical and Health Institutional Review Board.

Phenotypic and Functional Analysis of NK Cells

PBMCs were stained using Abs for flow cytometry, and $CD56^{dim}CD3^-CD14^-CD19^-$ cells were gated as previously described (Hwang et al. 2012. Int. Immunol. 24:792-802). Briefly, cells were stained with Abs for cell surface markers and then fixed in 2% formaldehyde. To distinguish g−NK cells, samples were treated with permeabilization buffer containing 0.1% saponin, followed by staining of intracellular proteins, including FcRγ (anti-FcεRI, γ subunit; Millipore) and CD3ζ (clone 6B10.2; eBioscience). MRC-5 lung fibroblasts or human foreskin fibroblasts were cultured in 96-well plates, infected (multiplicity of infection=1) with HCMV (Towne strain; or AD169) or HSV-1 for 2 hours, and then washed with PBS to remove unadsorbed virus. PBMCs were cultured for 1-5 days with HCMV infected cells or for 40 hours with HSV-1-infected cells in the presence of recombinant human IL-2 (10 U/ml). Six hours prior to analysis, 1 µl plasma or purified IgG (Nab Protein A Plus Purification Kit; Thermo Scientific) was added along with brefeldin A (for cytokine analysis) or anti-CD107a with monensin (for degranulation). To exclude dead cells, a LIVE/DEAD CellStain Kit (Invitrogen) was used.

ELISA

Serological status of donor plasma was determined using ELISA kits (MP Biomedicals), according to the manufacturer's instructions.

Statistics

The Wilcoxon matched pairs signed rank test was used for all assays with the exception of ELISAs, for which the $X^2$ test was used. Differences were considered significant when $p<0.05$ (GraphPad Prism).

Results and Discussion

Association between g$^-$NK Cells and HCMV Infection

To explore the origin of g$^-$NK cells, the phenotypic characteristics of conventional NK cells, which express FcRγ, were compared with g$^-$NK cells from healthy donors. Analysis of killer cell Ig-like receptors, which are expressed by subsets of NK cells (Parham et al. 2005. Nat Rev Immunol 5:201-214), showed that, in many donors, g$^-$NK cells predominantly expressed particular killer cell Ig-like receptors, suggesting that the g$^-$NK cell subset is an outcome of expansion.

Figure 6A:
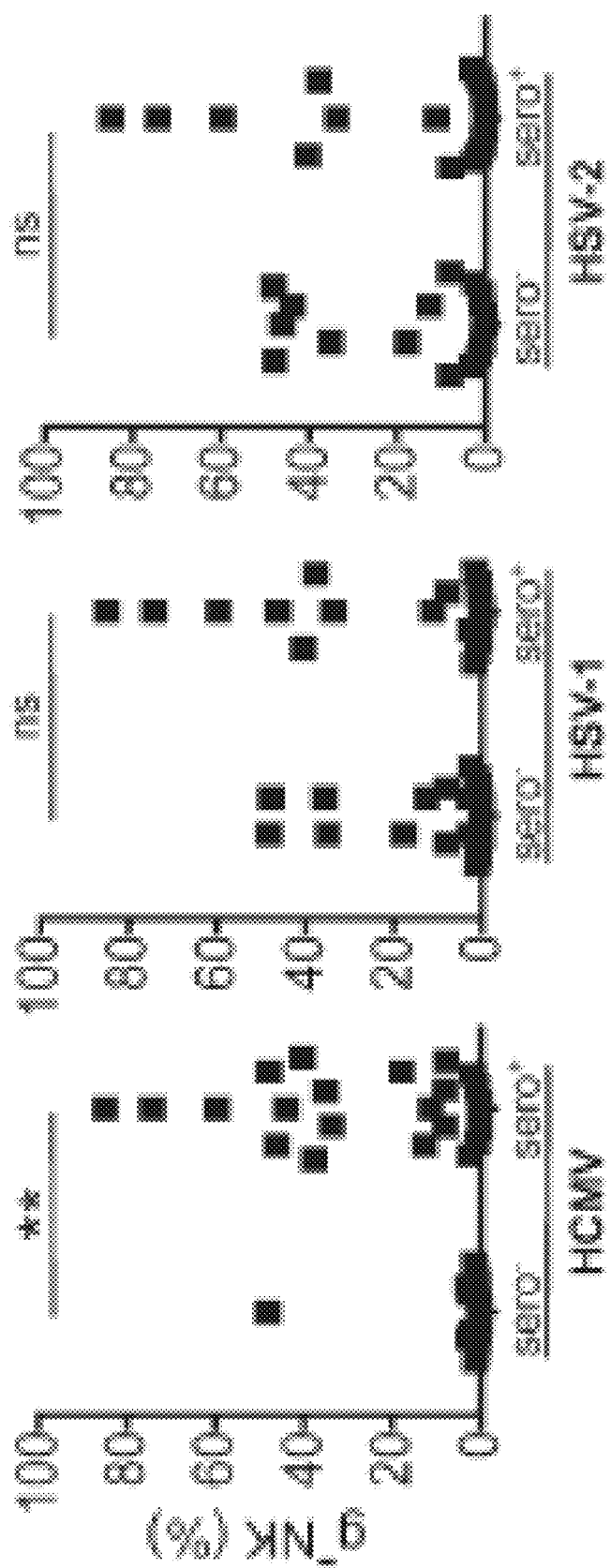
FIGS. 6A-B illustrate the association of g⁻NK cells with prior HCMV infection. (A) Frequencies of g⁻NK cells among the $CD56^{dim}CD3^-CD14^-CD19^-$population within individual donors grouped according to IgG serological status for HCMV, HSV-1, or HSV-2 (n=42). (B) Comparison of marker expression on conventional NK (s) and g⁻NK (d) cells within $CD56^{dim}CD3^-CD14^-CD19^-$population. Graphs show percentage of cells expressing indicated markers. *p<0.01, **p<0.0001. ns, Not significant.

Considering the expansion and presence of g$^-$NK cells in about one third of healthy donors (Hwang et al. 2012. Int. Immunol. 24:792-802), it was hypothesized that the presence of g$^-$NK cells are associated with prior infection by a common pathogen that does not cause illness in the presence of normal immune function. Previously, it was found that, compared with conventional NK cells, g$^-$NK cells display markedly lower levels of NKp30 and NKp46 (Hwang et al. 2012. Int. Immunol. 24:792-802), the natural cytotoxicity receptors associated with FcRγ(Moretta et al. 2006 Semin. Immunol. 18:151-158). Interestingly, a subset of NK cells with a similar NCR$^{lo}$ phenotype was found in HCMV-seropositive, but not in HCMV-seronegative, individuals (Guma et al. 2004. Blood. 104:3664-3671). To examine the possible association of g$^-$NK cells with HCMV, HCMV-specific Abs were tested in the plasma of 42 healthy donors, 17 of whom had g$^-$NK cells. HCMV seropositivity correlated strongly with the presence of g$^-$NK cells (p<0.0001); all donors with g$^-$NK cells, except for one, were seropositive for HCMV IgG (FIG. 6A). In contrast, seropositivity for HSV-1 or HSV-2, two common herpesviruses, did not correlate with the presence of g$^-$NK cells. Among the donors with g$^-$NK cells, only two were weakly positive for HCMV IgM (data not shown), suggesting that most of these seropositive donors did not have a recent HCMV infection. Analysis of the one HCMV-seronegative donor with g$^-$NK cells revealed a substantial number of memory T cells specific for the immunogenic HCMV tegument protein pp 65 (data not shown) (Lopez-Verges et al. 2011. PNAS USA 108:14725-14732), indicating that this donor had also been exposed to HCMV. Thus, the presence of g$^-$NK cells is strongly associated with previous exposure to HCMV.

Figure 6B:
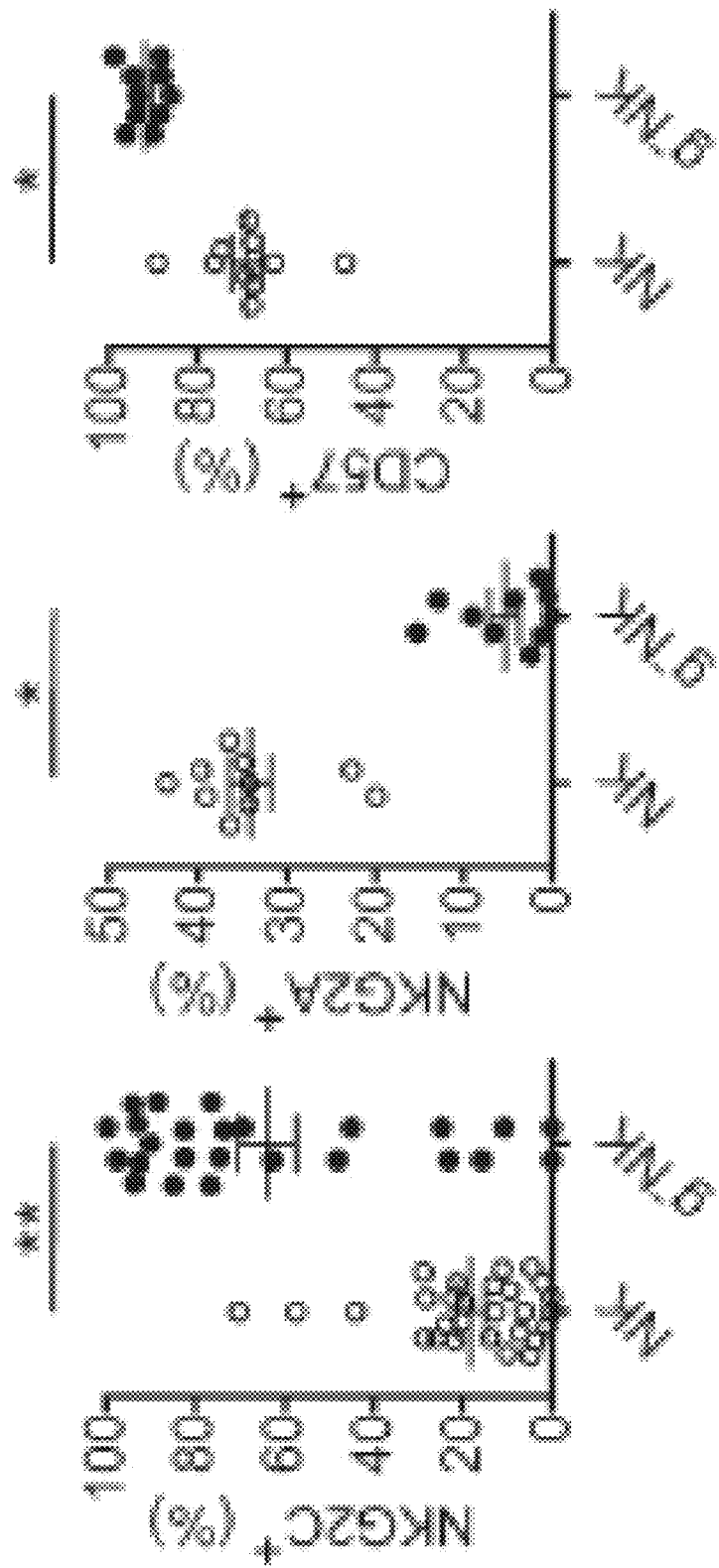

Unlike conventional NK cells, g$^-$NK cells showed predominant expression of NKG2C in many, but not all, donors (FIG. 6B). Notably, previous studies showed that HCMV-seropositive donors tend to have elevated numbers of NKG2C$^+$NK cells, which express high levels of CD57 and infrequent NKG2A (Guma et al. 2004. Blood. 104:3664-3671; Lopez-Verges et al. 2011. PNAS USA 108:14725-14732; Beziat et al. 2012. Eur. J. Immunol. 42:447-457). In line with this, g$^-$NK cells also expressed high CD57 and low NKG2A levels, regardless of NKG2C expression.

Figure 7C:
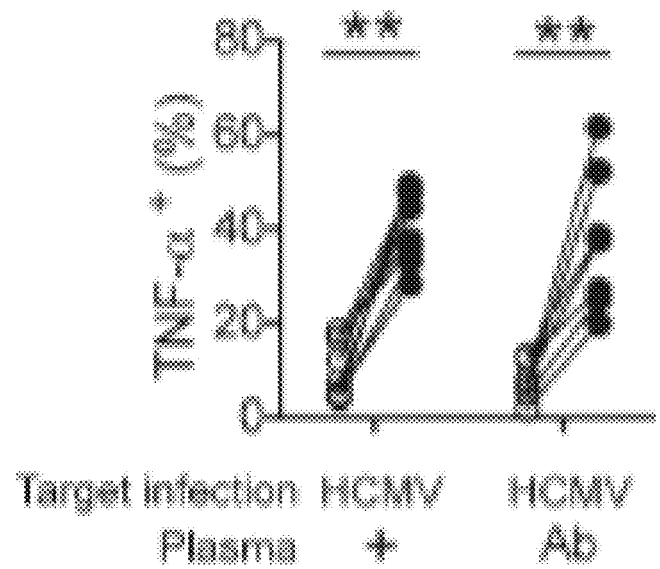

Requirement of Abs for Superior Responsiveness of g$^-$NK Cells to HCMV-infected Cells Given the association with HCMV infection, it was next determined whether g$^-$NK cells respond better than conventional NK cells to HCMV-infected cells. NK cell responsiveness was evaluated by examining intracellular IFN-γ after incubation of PBMCs with lung fibroblasts (MRC-5) that were either mock infected or infected with the Towne strain of HCMV (Cha et al. 1996. J. Virol. 70:78-83). Although the overall production of IFN-γ by NK cells was slightly increased over background, g$^-$NK cells produced less IFN-γ than conventional NK cells (FIG. 7A). The lower responsiveness of g$^-$NK cells was also observed with a different strain of HCMV (AD169), as well as with different host cells. These data indicate that g$^-$NK cells do not respond well to direct stimulation by HCMV-infected target cells. As it was previously determined that g$^-$NK cells responded robustly to stimulation through mAb-mediated cross-linking of CD16 (Hwang et al. 2012. Int. Immunol. 24:793-802), it was examined whether the presence of naturally occurring Abs against HCMV would impact g$^-$NK cell responses. Using flow cytometry, the presence was first confirmed, albeit at different concentrations, of Abs that bound to HCMV-infected cells in the plasma of seropositive donors (data not shown). Addition of autologous plasma led to the dramatic production of IFN-γ by g$^-$NK cells at levels significantly (p<0.01) higher than by conventional NK cells (FIG. 7B). Although there was notable variation, presumably reflecting variations in Ab concentrations and subclasses between donors, the g$^-$NK cells responded more robustly than did conventional NK cells from all donors tested. The enhancing effects of plasma were dependent on the presence of infected cells, because plasma with mock-infected cells did not induce such responses. Addition of Abs purified from autologous plasma also led to similarly high production of IFN-γ by g$^-$NK cells (FIG. 7B). These data indicate that plasma from all seropositive donors tested contained Abs specific for viral Ags expressed on the surface of infected cells that triggered cytokine production through CD16. The higher responses of g$^-$NK cells were also observed with the AD169 strain, as well as with different host cells in the presence of plasma. This robust responsiveness of g$^-$NK cells was observed consistently over a wide range of plasma concentrations and at different time points (data not shown). Furthermore, g$^-$NK cells produced significantly (p<0.01) higher levels of TNF-α compared with conventional NK cells in the presence of plasma or purified Ab (FIG. 7C).

Figure 7D:
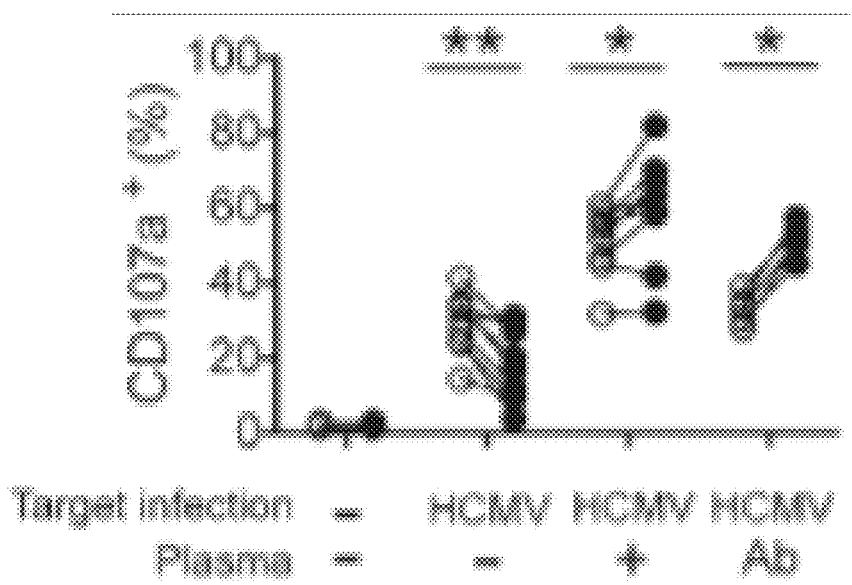

To assess the cytolytic potential of NK cells, the expression of CD107a, a degranulation marker, was examined following incubation with HCMV-infected target cells. In the absence of Ab, the degranulation response of g$^-$NK cells was significantly (p<0.01) lower than conventional NK cells (FIG. 7D). Compatible with the data, NKG2C$^+$NK cells in HCMV seropositive donors were previously shown to respond poorly to HCMV-infected cells (Magi et al. 2011. Blood. 117:848-856; Peterson et al. 2010. Hum. Immunol. 71: 29-35). In contrast, in the presence of plasma or purified Ab, g$^-$NK cells showed higher levels of CD107a (p<0.05) compared with conventional NK cells (FIG. 7D). Therefore, direct recognition is unlikely to be the primary mechanism for g$^-$NK cell reactivity against HCMV infected cells, and the enhanced cytokine and degranulation responses of g$^-$NK cells to HCMV-infected targets are Ab dependent. Taken together, the association with prior HCMV infection and enhanced Ab-dependent functional responsiveness of g⁻NK cells reveal distinct adaptive immune features that may lead to enhanced recall responses during reactivation or reinfection by HCMV.

Figure 8A:
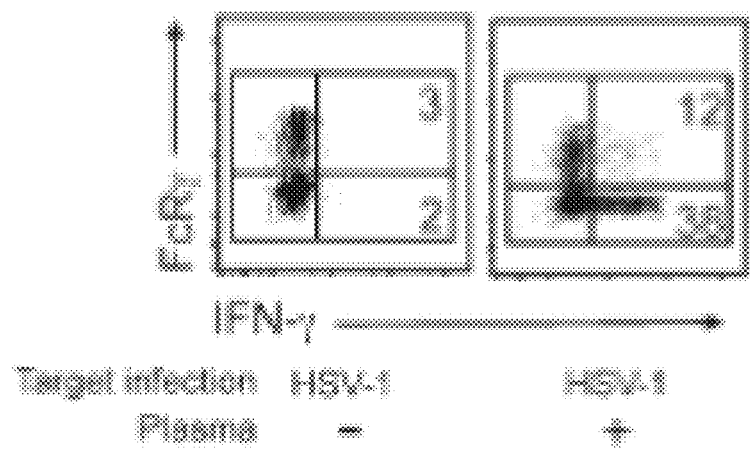
FIGS. 8A-C illustrate enhanced effector responses of g⁻NK cells to HSV-1-infected target cells in the presence of virus-specific Abs. (A) Dot plots from one representative sample depict relative percentages of IFN-γ⁺conventional NK and g⁻NK cells in the presence of autologous plasma after culture with HSV-1-infected MRC-5 cells. (B) Relative frequencies of IFN-γ⁺conventional NK (○) and g⁻NK (●) cells from anti-HSV-1⁺(n=6) or anti-HSV-1⁻donors (n=4) cultured with HSV-1-infected MRC-5 cells in the presence or absence of autologous plasma. Circles connected by a line designate the same donor sample. (C) IFN-γ production by g⁻NK and conventional NK cells from a representative HSV-1-seronegative donor in the presence of purified allogenic IgG following co-culture with HSV-1- or HCMV-infected target cells. The antiviral specificities of the plasma sources for purified IgG are indicated. All co-cultures were performed for 40 hours. *p<0.05.
Figure 8B:
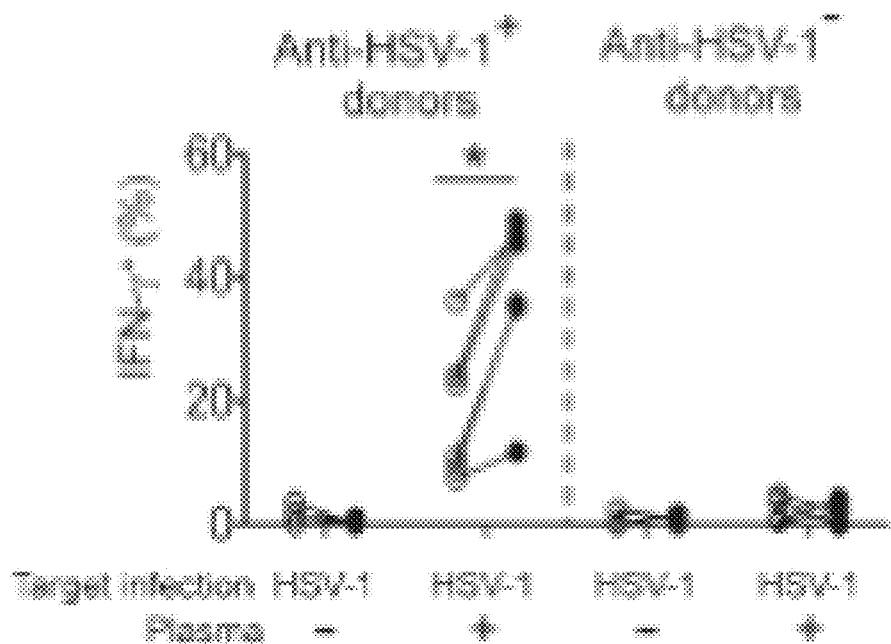

Enhanced Effector Responses of g⁻NK Cells to HSV-1-infected Cells in the Presence of Virus-specific Abs Given the augmented responsiveness in the presence of HCMV-specific Abs, it is thought that g⁻NK cells could also respond robustly to other pathogens when pathogen-specific Abs are available. To test this possibility, PBMCs from HSV-1-seropositive donors were co-cultured with HSV-1-infected cells in the presence or absence of autologous plasma. Similar to the HCMV-infection setting, IFN-γ production by g⁻NK cells was significantly higher ($p<0.05$) than from conventional NK cells in the presence of seropositive plasma (FIG. 8A, 8B). This plasma effect was Ab specific, because the addition of autologous plasma lacking HSV-1-specific Abs did not elicit such responses from HSV-1-naive g⁻NK cells (FIG. 8B). These data indicate that the plasma from HSV-1-seropositive donors contained Abs specific for HSV-1-derived Ag(s) on infected cells, and g⁻NK cells respond to HSV-1-infected target cells more robustly than do conventional NK cells in an HSV-1-specific Ab-dependent manner.

Figure 8C:
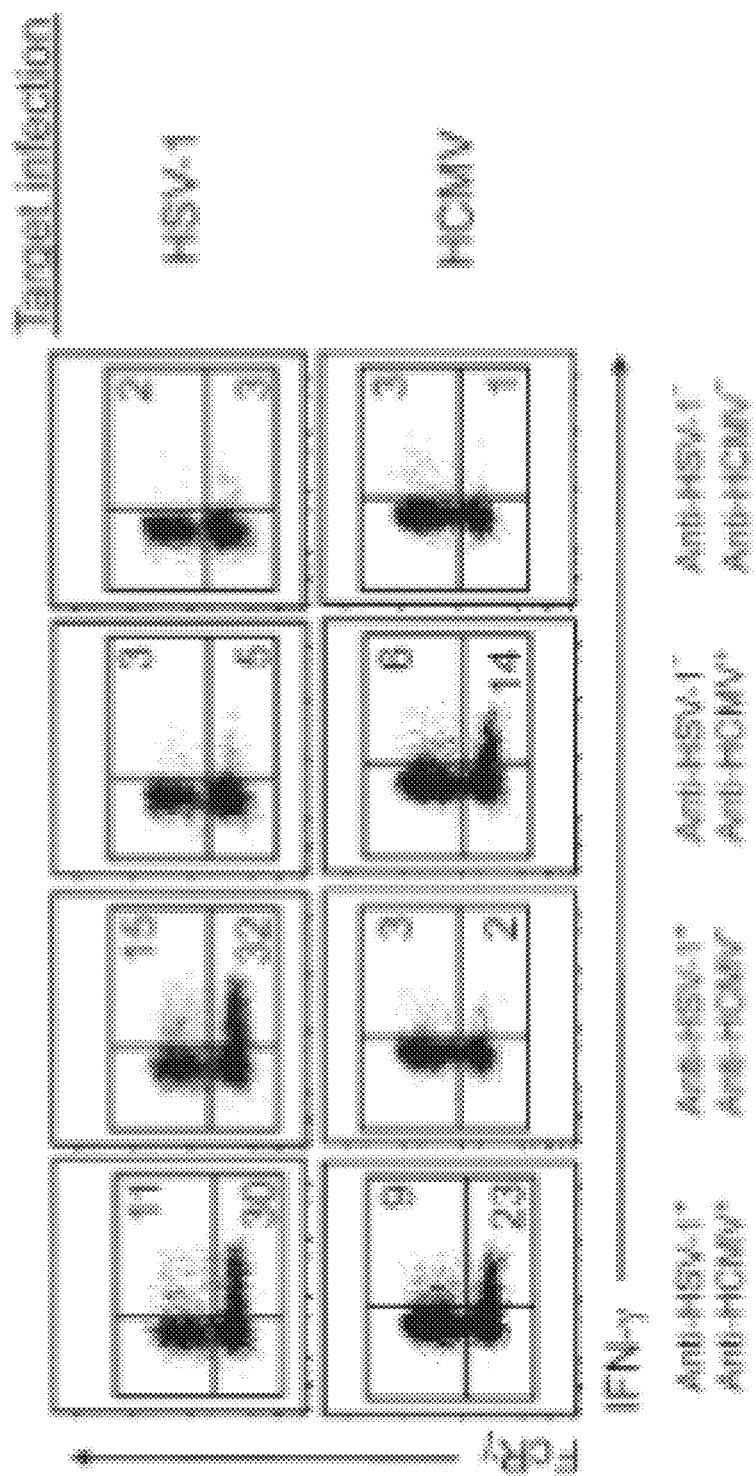

To examine whether g⁻NK cells from HSV-1-naive donors could respond to HSV-1-infected cells, Abs were purified from non-autologous plasma and tested for the ability to enhance cytokine production. The addition of Abs purified from HSV-1-seropositive donors led to greatly enhanced IFN-γ production by g⁻NK cells over conventional NK cells from HSV-1-naive donors co-cultured with HSV-1-infected cells (FIG. 8C). In contrast, Abs lacking HSV-1 reactivity did not yield such responses. In parallel experiments, the addition of non-autologous HCMV-specific Abs led to enhanced responses from g⁻NK cells cultured on HCMV-infected cells as expected. These data indicate that g⁻NK cells, regardless of prior exposure, can mount more potent functional responses to virus-infected cells than can conventional NK cells if virus specific Abs are provided. Thus, g⁻NK cells have enhanced potential to mediate Ab-dependent cross-protection against a broad spectrum of viral infections.

Long-term Persistence of g⁻NK Cells

Figure 9A:
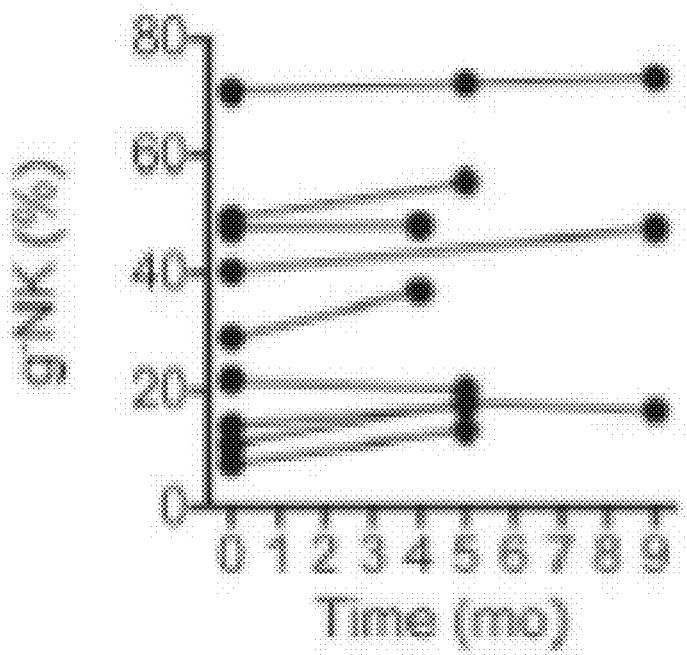
FIGS. 9A-D show that g⁻NK cells persist long-term at nearly constant levels. (A) Percentages of g⁻NK cells among total NK cells collected at the initial time point and 4, 5, or 9 months later from healthy donors (n=9). (B) Absolute number of indicated subsets among $1 \times 10^6$ lymphocytes collected at the initial time point ($T_1$) and 4 or 5 months later ($T_2$). Data are mean±SEM (n=7). (C) Expression analysis of Bcl-2 in conventional NK and g⁻NK cells from one representative donor. Shaded graph represents control staining (left panel). Mean fluorescence intensity of Bcl-2 expression (n=11) in conventional NK (○) and g⁻NK (●) cells (right panel). Circles connected by a line indicate the same donor sample. (D) Marker expression (mean fluorescence intensity) on conventional NK and g⁻NK cells. *p<0.01, **p<0.001.
Figure 9B:
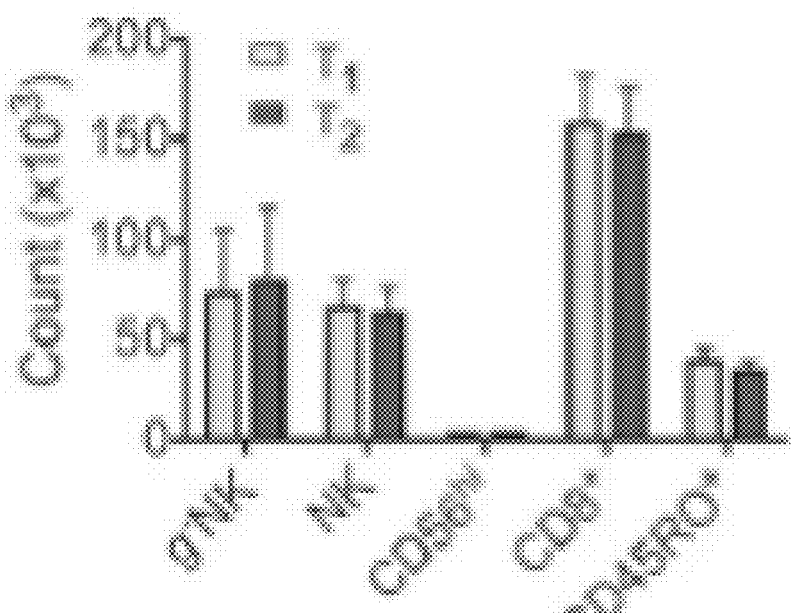
Figure 9C:
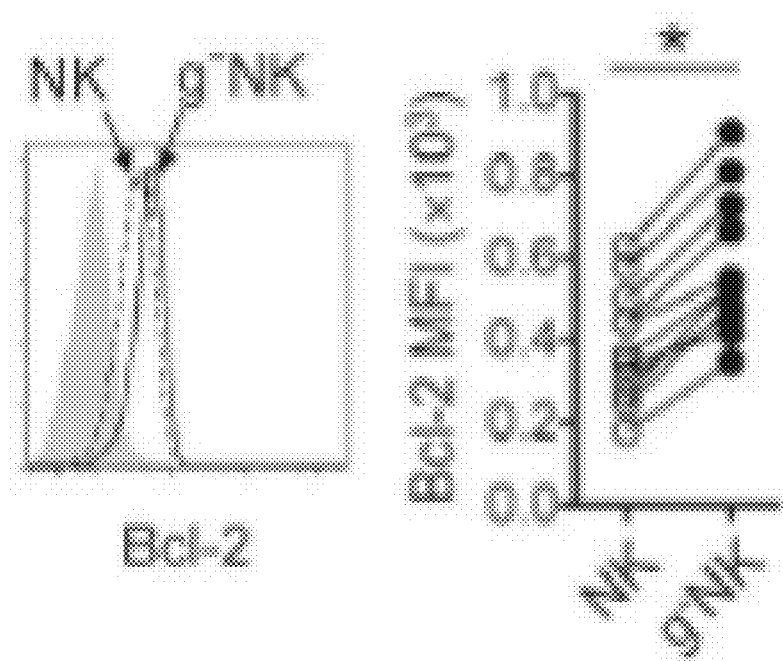
Figure 9D:
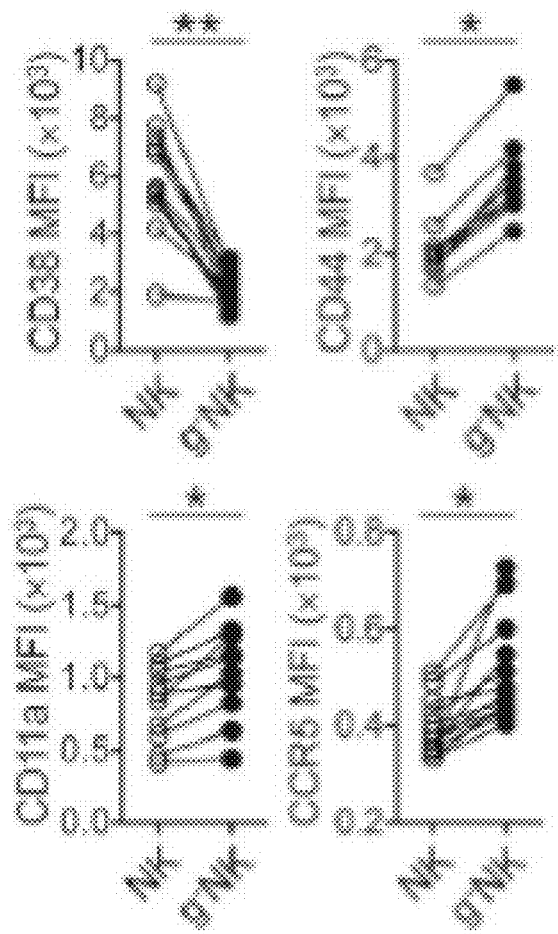
Figure 10:
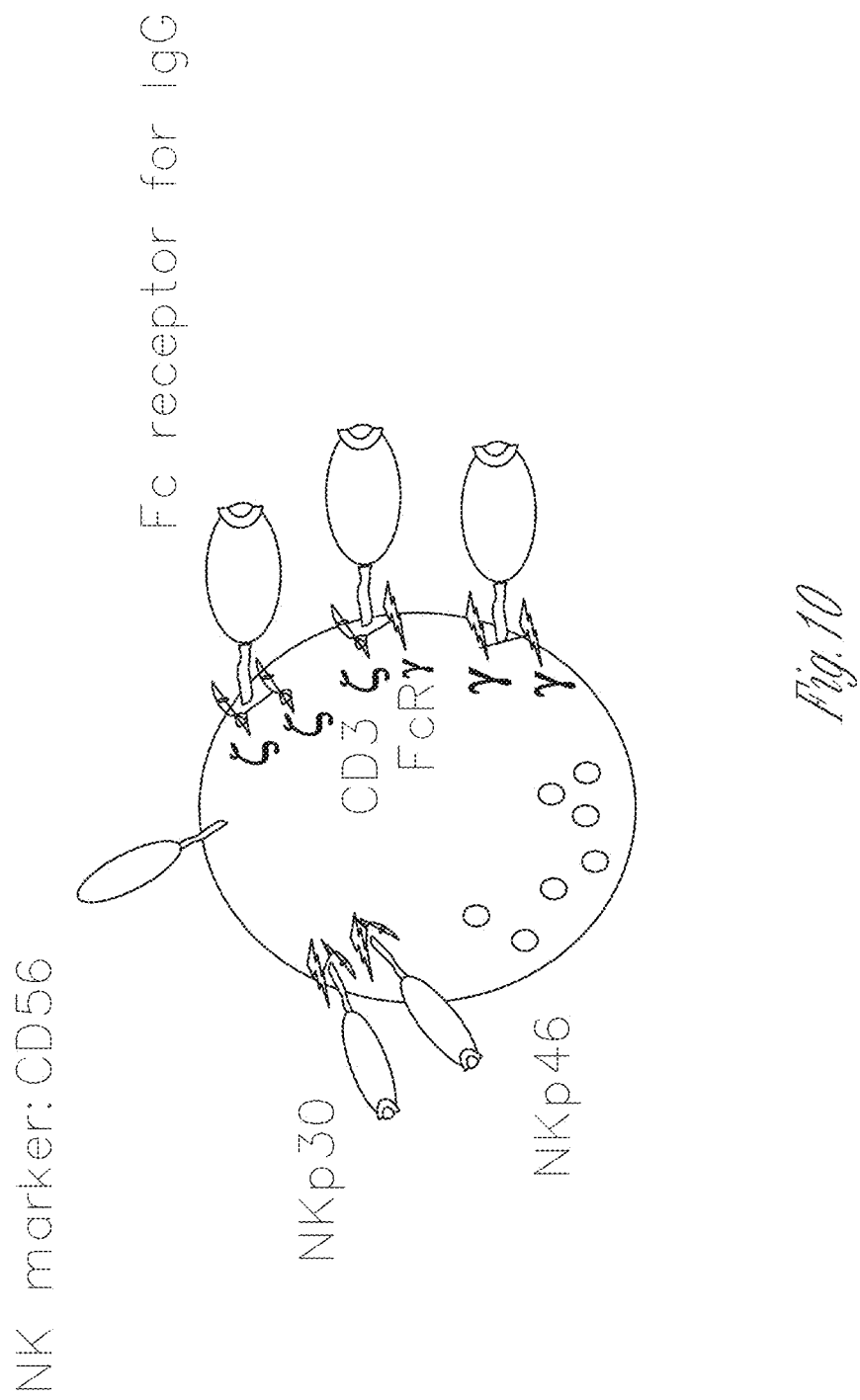
FIG. 10 is a schematic representation of human NK cells and some of the proteins expressed on the surface of human NK cells for their identification as such.
Figure 11:
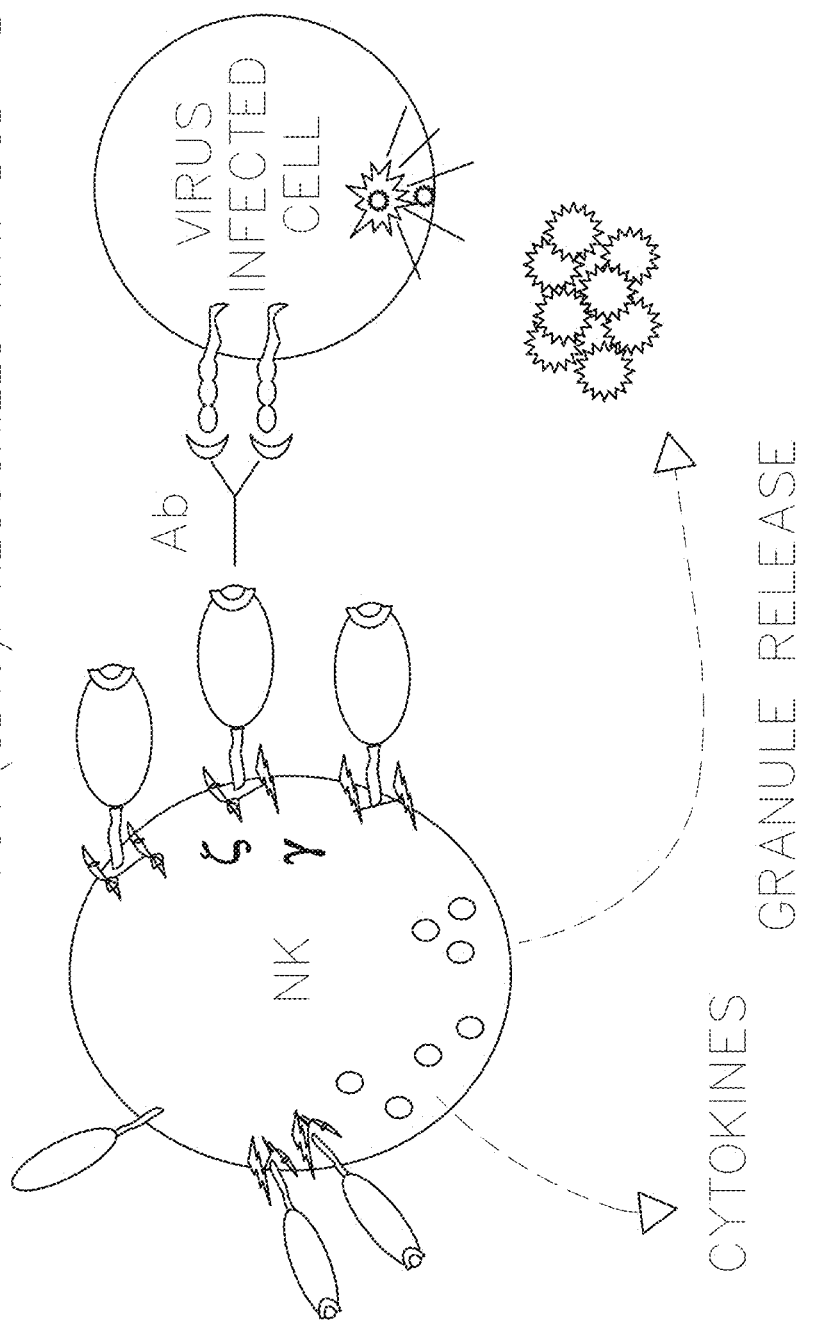
FIG. 11 depicts the antibody-mediated responses of NK cells following engagement of the antibody receptor, CD16, with antibody molecules bound to antigens expressed on a virus-infected target cell. The NK cell effector responses include cytokine production and cytolytic granule release.
Figure 12B:
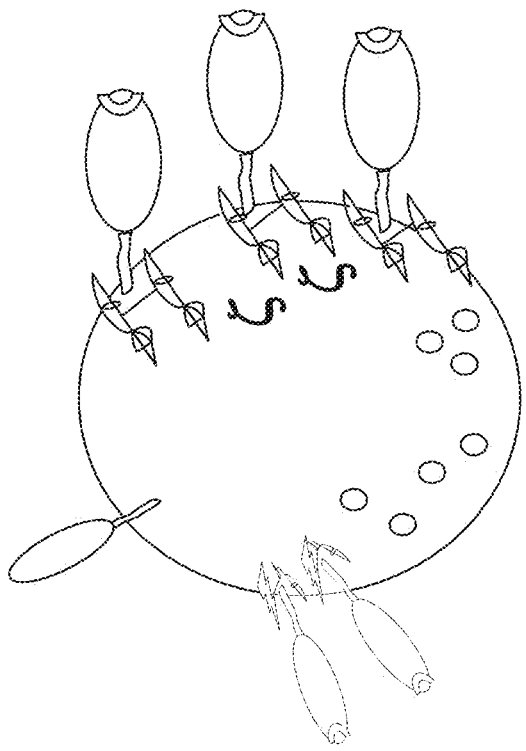
FIGS. 12A-B depict conventional NK (FcRγ-sufficient) and FcRγ-deficient (g⁻) NK cells to illustrate the lack of FcRγ expression and the low levels of NKp46 and NKp30 on g⁻NK cells.
Figure 12A:
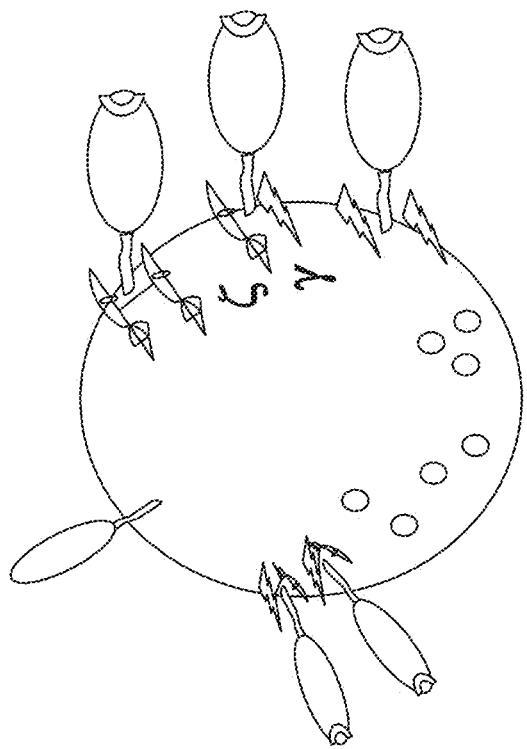
Figure 13:
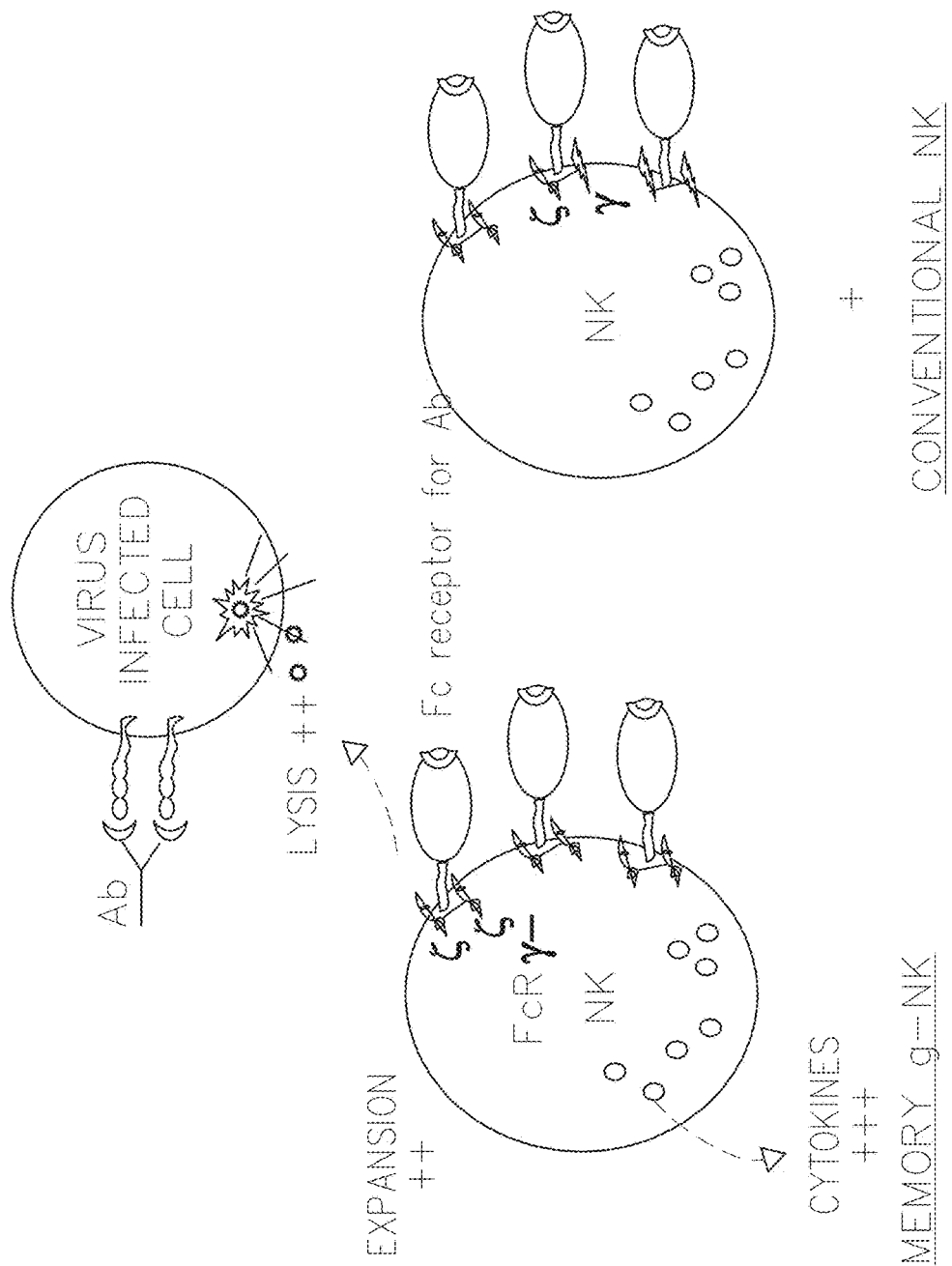
FIG. 13 depicts various responses of memory g⁻NK and conventional NK cells upon their encounter of virus-infected cells during re-infection or chronic infection, or encounter of tumor cells during tumor antigen-specific antibody therapy for cancer treatment.

It was next sought to determine whether g⁻NK cells are a transient or stable population. Longitudinal studies showed that the relative frequencies of g⁻NK cells within the NK cell pool, as well as their absolute numbers, were nearly constant for 4-9 mo after original assessments (FIG. 9A, 4B). The subset composition of g⁻NK cells was also stable, and there was no discernible change in functional responsiveness at these time points (data not shown). For donors that initially had no detectable g⁻NK cells (n=7), there was no appearance of g⁻NK cells during this period (data not shown). With respect to abundance, certain donors maintained large numbers of g⁻NK cells, in some cases exceeding the number of recirculating memory CD8⁺CD45RO⁺ T cells (FIG. 9B). These results indicate that the size of the g⁻NK cell pool is maintained long-term with no indication of decline, a feature of memory-type cells. Because the anti-apoptotic protein Bcl-2 has a role in NK cell survival (Ranson et al. 2003. Blood. 4887-4893; Cooper et al. 2002. Blood. 100:3633-3638) and is also elevated in memory CD8⁺ T cells (Grayson et al. 2000. J. Immunol. 164:3950-3954), expression of this protein was analyzed. In all donors (n=11), g⁻NK cells expressed significantly higher levels ($p<0.01$) of Bcl-2 than did conventional NK cells (FIG. 9C). Analysis of the activation marker CD38, together with the previous data showing no detectable expression of activation markers CD69 and CD25, indicated that g⁻NK cells were not in an activated state (FIG. 9D). Finally, several markers that have been associated with memory T cells (Sallusto et al. 1999. Nature. 401:708-712) were analyzed. Although g⁻NK cells did not express CD45RO, CCR7, or CD127, the levels of CD44, CD11a, and CCR5 were higher on g⁻NK cells compared with conventional NK cells (FIG. 9D, data not shown), reminiscent of the differences between naive and memory T cells (Sallusto et al. 1999. Nature. 401:708-712). Together, g⁻NK cells appear to be long lived quiescent memory-type cells.

Collectively, this study reveals memory features of g⁻NK cells distinct from other memory cells. Unlike classical memory cells that use gene-rearranged Ag-specific receptors, g⁻NK cells use the germ line-encoded FcR that recognizes Abs bound to target cells. Moreover, g⁻NK cells are unlikely related to Ag-specific memory NK cells described in mouse models (O'Leary et al. 2006. Nat. Immunol. 7:507-516; Sun et al. 2009. Nature. 457:557-561; Paust et al. 2010. Nat. Immunol. 11:1127-1135), because FcRγdeficiency abrogates CD16 expression on murine NK cells (Takai et al. 1994. Cell. 76:519-529), and these memory-type NK cells disappear with a constant rate of decay (Schlub et al. 2011. J. Immunol. 187:1385-1392). The responses of g⁻NK cells are not restricted to a specific pathogen, because Ag specificity is conferred through Ag-specific Abs. Given the persistence and enhanced capabilities, g⁻NK cells are poised to impact the host immune response to diverse pathogens over the long-term, particularly during later stages of primary infection, reinfection, or chronic infection if pathogen-specific Abs are available. Thus, g⁻NK cells represent a new class of memory cells that does not depend on Ag-specific receptors, for which FcRγdeficiency itself provides a molecular signature. Finally, g⁻NK cells may have important implications for Ab-based therapies for infectious diseases and cancer in which the enhanced responsiveness of g⁻NK cells to Abbound targets could significantly impact therapeutic efficacy.

BIBLIOGRAPHY

1. Lanier L L (2008) *Nat Immunol* 9(5):495-502.
2. Bryceson Y T & Long E O (2008) *Curr Opin Immunol* 20(3):344-352.
3. Orange J S (2008) *Nat Rev Immunol* 8(9):713-725.
4. Caligiuri M A (2008) *Blood* 112(3):461-469.
5. Vivier E, et al. (2011) *Science* 331(6013):44-49.
6. Sivori S, et al. (1999) *Eur J Immunol* 29(5):1656-1666.
7. Bottino C, Moretta L, & Moretta A (2006) *Curr Top Microbiol Immunol* 298:175-182.
8. Brandt C S, et al. (2009) *J Exp Med* 206(7):1495-1503.
9. Campbell K S & Purdy A K (2011) *Immunology* 132(3):315-325.
10. Vivier E, et al. (1991) *J Immunol* 147(12):4263-4270.
11. Pende D, et al. (1999) *J Exp Med* 190(10):1505-1516.
12. Lanier L L, Yu G, & Phillips J H (1989) *Nature* 342(6251):803-805.
13. De Maria A, et al. (2003) *Eur J Immunol* 33(9):2410-2418.
14. Mavilio D, et al. (2003) *Proc Natl Acad Sci USA* 100(25):15011-15016.
15. Fauriat C, et al. (2007) *Blood* 109(1):323-330.
16. Narni-Mancinelli E, et al. (2011) *Proc Natl Acad Sci USA* 108(45):18324-18329.
17. Kim S, et al. (2005) *Nature* 436(7051):709-713.

18. Yokoyama W M & Kim S (2006) *Immunity* 24(3):249-257.
19. Anfossi N, et al. (2006) *Immunity* 25(2):331-342.
20. Yawata M, et al. (2006) *J Exp Med* 203(3):633-645.
21. Yu J, et al. (2007) *J Immunol* 179(9):5977-5989.
22. Kim S, et al. (2008) *Proc Natl Acad Sci USA* 105(8): 3053-3058.
23. Parsons M S, Zipperlen K, Gallant M, & Grant M (2010) *J Leukoc Biol* 88(5):905-912.
24. Parham P (2005) *Nat Rev Immunol* 5(3):201-214.
25. Kikuchi-Maki A, Catina T L, & Campbell K S (2005) *J Immunol* 174(7):3859-3863.
26. Lopez-Verges S, et al. (2010) *Blood* 116(19):3865-3874.
27. Bjorkstrom N K, et al. (2010) *Blood* 116(19):3853-3864.
28. Fauriat C, Long E O, Ljunggren H G, & Bryceson Y T (2010) *Blood* 115(11):2167-2176.
29. Bida A T, et al. (2011) *Mol Immunol* 48(9-10):1149-1159.
30. Carter P J (2006) *Nat Rev Immunol* 6(5):343-357.
31. Kohrt H E, et al. (2011) *Blood* 117(8):2423-2432.

All patents and publications, as well as amino acid or nucleotide sequences represented by accession numbers, referenced or mentioned herein are indicative of the levels of skill of those skilled in the art to which the invention pertains, and each such referenced patent or publication as well as amino acid or nucleotide sequences represented by accession numbers, is hereby specifically incorporated by reference to the same extent as if it had been incorporated by reference in its entirety individually or set forth herein in its entirety. Applicants reserve the right to physically incorporate into this specification any and all materials and information from any such cited patents or publications or accession numbers.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a polypeptide" includes a plurality of such nucleic acids or polypeptides (for example, a solution of nucleic acids or polypeptides or a series of nucleic acid or polypeptide preparations), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed:

1. A method of treating a subject having cancer, comprising administering to the subject a composition comprising a cell population comprising an effective amount of natural killer cells that do not express substantial FcRγ (g⁻NK cells), and administering one or more therapeutic antibody that binds to the cancer cells to the subject separately or with the composition comprising g⁻NK cells, wherein the one or more therapeutic antibody binds to CD16 on the surface of the g⁻NK cells, to thereby treat the cancer in the subject.

2. The method of claim 1, wherein the g⁻NK cells in the composition comprising g⁻NK cells are isolated from the subject.

3. The method of claim 2, wherein the g⁻NK cells in the composition comprising g⁻NK cells isolated from the subject are cultured in a cell culture medium prior to administering the composition.

4. The method of claim 2, wherein IL-12, IL-15, IL-18, IL-2, and/or CCL5 is administered to the subject prior to isolating the g⁻NK cells.

5. The method of claim 1, further comprising identifying whether the subject has g⁻NK cells by identifying cells that do not express substantial FcRγ, but do express at least one marker for natural killer cells, prior to administering the composition.

6. The method of claim 5, wherein identifying whether the subject has g⁻NK cells comprises obtaining lymphocytes from the subject.

7. The method of claim 1, wherein the g⁻NK cells express KIR2DL2/3, or NKG2C, or a combination thereof.

8. The method of claim 1, wherein the cell population comprises at least 70% g⁻NK cells.

9. The method of claim 1, wherein the g⁻NK cells express low levels of NKp30 and NKp46, compared to conventional NK cells.

10. The method of claim 1, wherein the g⁻NK cells in the composition comprising g⁻NK cells are isolated from a donor.

11. The method of claim 10, wherein the g⁻NK cells in the composition comprising g⁻NK cells isolated from the donor are cultured in a cell culture medium prior to administering the composition.

12. The method of claim 10, wherein IL-12, IL-15, IL-18, IL-2, and/or CCL5 is administered to the donor prior to isolating the g⁻NK cells.

* * * * *